United States Patent
Galibert et al.

(10) Patent No.: US 7,267,960 B2
(45) Date of Patent: Sep. 11, 2007

(54) ANTAGONISTS AND AGONISTS OF LDCAM AND METHODS OF USE

(75) Inventors: Laurent J. Galibert, Seattle, WA (US); Wei Yan, Sammamish, WA (US)

(73) Assignee: Amgen Inc., Thousand Oaks, CA (US)

( * ) Notice: Subject to any disclaimer, the term of this patent is extended or adjusted under 35 U.S.C. 154(b) by 161 days.

(21) Appl. No.: 10/898,408

(22) Filed: Jul. 23, 2004

(65) Prior Publication Data

US 2005/0058642 A1    Mar. 17, 2005

Related U.S. Application Data

(60) Provisional application No. 60/490,027, filed on Jul. 25, 2003.

(51) Int. Cl.
  G01N 33/53   (2006.01)
  C07K 16/28   (2006.01)
  C07K 17/00   (2006.01)

(52) U.S. Cl. ................ 435/7.1; 530/388.24; 530/391.1

(58) Field of Classification Search ................ 435/7.1; 530/388.24, 391.1
See application file for complete search history.

(56) References Cited

U.S. PATENT DOCUMENTS

| | | | |
|---|---|---|---|
| 5,686,257 | A | 11/1997 | Kennedy et al. |
| 6,512,095 | B2 | 1/2003 | Baum |
| 6,642,360 | B2 | 11/2003 | Filvaroff et al. |
| 2002/0168712 | A1 | 11/2002 | Baum |
| 2002/0198147 | A1 | 12/2002 | Baker et al. |

FOREIGN PATENT DOCUMENTS

| | | |
|---|---|---|
| WO | WO97/13844 | 4/1997 |
| WO | WO99/28462 | 6/1999 |
| WO | WO99/57132 | 11/1999 |
| WO | WO00/29435 | 5/2000 |
| WO | WO00/32635 | 6/2000 |
| WO | WO00/32776 | 6/2000 |
| WO | WO01/00237 A1 | 1/2001 |
| WO | WO01/54477 A2 | 8/2001 |
| WO | WO02/26930 A2 | 4/2002 |

OTHER PUBLICATIONS

Attwood, T. "The bable of bioinformatics," *Science*, 290:47-49, 2000.

Biederer, et al., "SynCAM, a synaptic adhesion molecule that drives synapse assembly," *Science* 297:1525-1531, 2002.

Bost, K.L. and Pascual, D.W., "Antibodies against a peptide sequence within the HIV envelope protein crossreacts with human interleukin-2," *Immunol. Invest.*, 17(6-7):577-586, 1988.

Gomyo, H. et al., "A 2-Mb sequence-ready contig map and a novel immunoglobulin superfamily gene *IGSF4* in the LOH region of chromosome 11q23.2," *Genomics*, 62:139-146, 1999.

Greene, J.L. et al., "Covalent dimerization of CD28/CTLA-4 and oligomerization of CD80/CD86 regulate T cell costimulatory interactions," *J. Biol. Chem.*, 271(43):26762-26771, 1996.

Kennedy, et al., "A molecular analysis of NKT cells: identification of a class-1 restricted T cell-associated molecule (CRTAM)," *J Leuk. Bio.* 67:725-734, 2000.

Kuramochi et al., "*TSLC1* is a tumor-suppressor gene in human non-small-cell lung cancer," *Nat Genet* 27(4):427-30, 2001.

Linsley, P.S. et al., "Binding stoichiometry of the cytotoxic T lymphocyte-associated molecule-4 (CTLA-4)," *J. Biol. Chem.*, 270(25):15417-15424, 1995.

Masuda et al., "The tumor suppressor protein TSLC1 is involved in cell-cell adhesion," *J Biol Chem.* 277(34):31014-31019, 2002.

Metzler et al., "Solution structure of human CTLA-4 and delineation of a CD80/CD86 binding site conserved in CD28," *Nat. Struct. Biol.*, 4:527-531, 1997.

The Riken Genome Exploration Research Group Phase II Team and the Fantom Consortium; "Functional annotation of a full-length mouse cDNA collection," *Nature* 409:685-690, 2001.

Skolnick et al. "From genes to protein structure and function: novel applications of computational approaches in the genomic era," *Trends in Biotech.*, 18(1):34-39, 2000.

Strausberg, R., NCBI, Accession No. AA493561, Aug. 20, 1997.

Urase K., et al., Expression of RA175 mRNA, a new member of the immunoglobulin superfamily, in developing mouse brain, , *NeuroReport* 12(15):3217-3221, 2001.

Wakayama T., et al., "Cloning and Characterization of a Novel Mouse Immunoglobulin Superfamily Gene Expressed in Early Spermatogenic Cells," *Molecular Reproduction and Development* 60:158-164, 2001.

*Primary Examiner*—Maher M. Haddad
(74) *Attorney, Agent, or Firm*—James E. Klaniecki

(57) ABSTRACT

The invention pertains to agonists and antagonists of LDCAM and methods of treating disease and infection by administering one or more LDCAM antagonists or agonists. This abstract is provided for the sole purpose of enabling the reader to quickly ascertain the subject matter of the technical disclosure and is not intended to be used to interpret or limit the scope or meaning of the claims.

12 Claims, 17 Drawing Sheets

| Sequence Name(s) | Sequence Description | Human Accession # | Mouse Accession # |
| --- | --- | --- | --- |
| ACTN1 | Human non-muscle alpha-actinin mRNA, complete cds. | M95178 | AI195392 |
| ADFP | Adipose differentiation-related protein | BC005127 | M93275 |
| ANPEP | alanyl (membrane) aminopeptidase (aminopeptidase N, aminopeptidase M, microsomal aminopeptidase, CD13, p150) | NM_001150 | U77083 |
| BST1 | bone marrow stromal cell antigen 1 | NM_004334 | D31788 |
| CD63 | CD63 antigen (melanoma 1 antigen) | NM_001780 | D16432 |
| CD81 | CD81 antigen (target of antiproliferative antibody 1) | NM_004356 | X59047 |
| Clic4 | chloride intracellular channel 4 (mitochondrial) | AL577024 | AI845237 |
| CREG | Cellular Repressor of E1A-stimulated Genes CREG | AF084523 | AK010947 |
| CSRP1 | cysteine and glycine-rich protein 1 | NM_004078 | AI837225 |
| CXCL9 | Chemokine (C-X-C motif) ligand 9. Monokine induced by gamma interferon | NM_002416 | M34815 |
| CXCL16 | Chemokine (C-X-C motif) ligand 16 | AL531790 | AI019535 |
| DNASE1L3 | deoxyribonuclease I-like 3 | NM_004944 | AF047355 |
| DYSF | Dysferlin | AF075575 | NM_021469 |
| EPLIN | epithelial protein lost in neoplasm beta | NM_016357 | AI552619 |
| GADD45B | Growth arrest and DNA-damage-inducible protein GADD45beta | AF078077 | AV138783 |
| IGSF4 | immunoglobulin superfamily, member 4 | NM_014333 | AF061260 |
| ITGAE | integrin, alpha E, epithelial-associated | L25851 | NM_008399 |
| IL15 | interleukin 15 | NM_000585 | U14332 |
| LY75 | lymphocyte antigen 75 | NM_002349 | NM_013825 |
| MARCKS | myristoylated alanine-rich protein kinase C substrate | NM_002356 | M60474 |
| PIK3CB | Phosphatidylinositol 3-kinase catalytic subunit Beta isoform | AA805318 | AA111021 |
| PPAP2A | Homo sapiens mRNA for phosphatidic acid phosphatase 2a, complete cds. | AB000888 | D84376 |
| PSMB9 | proteasome (prosome, macropain) subunit, beta type, 9 | NM_002800 | D44456 |
|  | (large multifunctional protease 2) |  |  |
| RGS10 | regulator of G-protein signalling 10 | NM_002925 | AA123848 |
| SLC11A1 | solute carrier family 11 (proton-coupled divalent metal ion transporters), member 1 | L32185 | L13732 |
| TAP2 | transporter 2, ATP-binding cassette, sub-family B (MDR/TAP) | NM_000544 | U60091 |
| UBE2N | ubiquitin-conjugating enzyme E2N (UBC13 homolog, yeast) | NM_003348 | AW210080 |

*FIGURE 2*

Variable region VH (heavy chain)    SEQ ID NO:12

QVQLVQWGAG LLKPSETLSL TCAVYGGSFS GHYWSWIRQP PGKGLEWIGE
INHSGSTNYN PSLKSRVTMS VDTSKNQFSL RLNSVTAADT AVYYCARVSW
YFDLWGKGTL VTVSS

Variable region VL (light chain)    SEQ ID NO:13

PELTQDPAVS VALGQTVRIT CQGDSLRSYY ASWYQQKPGQ APVLVIYGKN NRPSG
SGSSSGNTAS LTITGAQAED EADYYCNSRD SSSTHRGVFG GGTKLTVLG

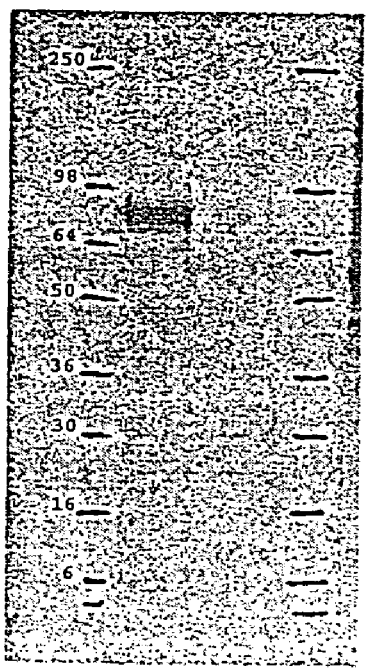 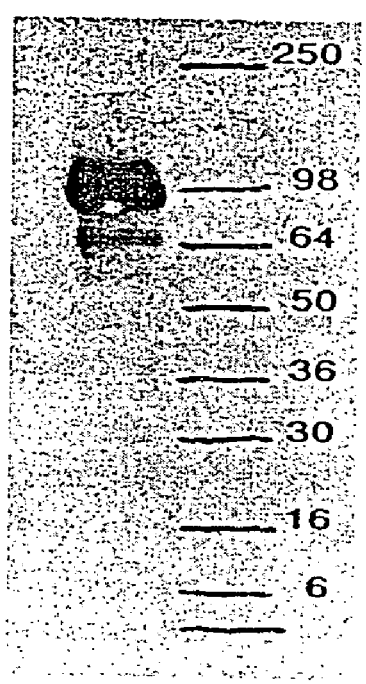
*FIGURE 13*

SEQUENCE LISTING

```
<160> NUMBER OF SEQ ID NOS: 13

<210> SEQ ID NO 1
<211> LENGTH: 1598
<212> TYPE: DNA
<213> ORGANISM: homo sapiens
<220> FEATURE:
<221> NAME/KEY: CDS
<222> LOCATION: (16)..(1341)

<400> SEQUENCE: 1
gcggccgcgc ccgac atg gcg agt gta gtg ctg ccg agc gga tcc cag tgt         51
                Met Ala Ser Val Val Leu Pro Ser Gly Ser Gln Cys
                1               5                   10 gcg gcg gca gcg gcg gcg gcg gcg cct ccc ggg ctc cgg ctc cgg ctt          99
Ala Ala Ala Ala Ala Ala Ala Ala Pro Pro Gly Leu Arg Leu Arg Leu
            15                  20                  25 ctg ctg ttg ctc ttc tcc gcc gcg gca ctg atc ccc aca ggt gat ggg         147
Leu Leu Leu Leu Phe Ser Ala Ala Ala Leu Ile Pro Thr Gly Asp Gly
        30                  35                  40 cag aat ctg ttt acg aaa gac gtg aca gtg atc gag gga gag gtt gcg         195
Gln Asn Leu Phe Thr Lys Asp Val Thr Val Ile Glu Gly Glu Val Ala
45                  50                  55                  60 acc atc agt tgc caa gtc aat aag agt gac gac tct gtg att cag cta         243
Thr Ile Ser Cys Gln Val Asn Lys Ser Asp Asp Ser Val Ile Gln Leu
                65                  70                  75 ctg aat ccc aac agg cag acc att tat ttc agg gac ttc agg cct ttg         291
Leu Asn Pro Asn Arg Gln Thr Ile Tyr Phe Arg Asp Phe Arg Pro Leu
            80                  85                  90 aag gac agc agg ttt cag ttg ctg aat ttt tct agc agt gaa ctc aaa         339
Lys Asp Ser Arg Phe Gln Leu Leu Asn Phe Ser Ser Ser Glu Leu Lys
        95                 100                 105 gta tca ttg aca aac gtc tca att tct gat gaa gga aga tac ttt tgc         387
Val Ser Leu Thr Asn Val Ser Ile Ser Asp Glu Gly Arg Tyr Phe Cys
    110                 115                 120 cag ctc tat acc gat ccc cca cag gaa agt tac acc acc atc aca gtc         435
Gln Leu Tyr Thr Asp Pro Pro Gln Glu Ser Tyr Thr Thr Ile Thr Val
125                 130                 135                 140 ctg gtc cca cca cgt aat ctg atg atc gat atc cag aaa gac act gcg         483
Leu Val Pro Pro Arg Asn Leu Met Ile Asp Ile Gln Lys Asp Thr Ala
                145                 150                 155 gtg gaa ggt gag gag att gaa gtc aac tgc act gct atg gcc agc aag         531
Val Glu Gly Glu Glu Ile Glu Val Asn Cys Thr Ala Met Ala Ser Lys
            160                 165                 170 cca gcc acg act atc agg tgg ttc aaa ggg aac aca gag cta aaa ggc         579
Pro Ala Thr Thr Ile Arg Trp Phe Lys Gly Asn Thr Glu Leu Lys Gly
        175                 180                 185 aaa tcg gag gtg gaa gag tgg tca gac atg tac act gtg acc agt cag         627
Lys Ser Glu Val Glu Glu Trp Ser Asp Met Tyr Thr Val Thr Ser Gln
```

| | | | | | | | | | | | | |
|---|---|---|---|---|---|---|---|---|---|---|---|---|
| Lys | Ser | Glu | Val | Glu | Trp | Ser | Asp | Met | Tyr | Thr | Val | Thr | Ser | Gln |
| | 190 | | | | 195 | | | | 200 | | | |

```
ctg atg ctg aag gtg cac aag gag gac gat ggg gtc cca gtg atc tgc     675
Leu Met Leu Lys Val His Lys Glu Asp Asp Gly Val Pro Val Ile Cys
205                 210                 215                 220 cag gtg gag cac cct gcg gtc act gga aac ctg cag acc cag cgg tat     723
Gln Val Glu His Pro Ala Val Thr Gly Asn Leu Gln Thr Gln Arg Tyr
                225                 230                 235 cta gaa gta cag tat aag cct caa gtg cac att cag atg act tat cct     771
Leu Glu Val Gln Tyr Lys Pro Gln Val His Ile Gln Met Thr Tyr Pro
            240                 245                 250 cta caa ggc tta acc cgg gaa ggg gac gcg ctt gag tta aca tgt gaa     819
Leu Gln Gly Leu Thr Arg Glu Gly Asp Ala Leu Glu Leu Thr Cys Glu
        255                 260                 265 gcc atc ggg aag ccc cag cct gtg atg gta act tgg gtg aga gtc gat     867
Ala Ile Gly Lys Pro Gln Pro Val Met Val Thr Trp Val Arg Val Asp
    270                 275                 280 gat gaa atg cct caa cac gcc gta ctg tct ggg ccc aac ctg ttc atc     915
Asp Glu Met Pro Gln His Ala Val Leu Ser Gly Pro Asn Leu Phe Ile
285                 290                 295                 300 aat aac cta aac aaa aca gat aat ggt aca tac cgc tgt gaa gct tca     963
Asn Asn Leu Asn Lys Thr Asp Asn Gly Thr Tyr Arg Cys Glu Ala Ser
                305                 310                 315 aac ata gtg ggg aaa gct cac tcg gat tat atg ctg tat gta tac gat    1011
Asn Ile Val Gly Lys Ala His Ser Asp Tyr Met Leu Tyr Val Tyr Asp
            320                 325                 330 ccc ccc aca act atc cct cct ccc aca aca acc acc acc acc acc       1059
Pro Pro Thr Thr Ile Pro Pro Pro Thr Thr Thr Thr Thr Thr Thr
        335                 340                 345 acc acc acc acc acc atc ctt acc atc atc aca gat tcc cga gca ggt   1107
Thr Thr Thr Thr Thr Ile Leu Thr Ile Ile Thr Asp Ser Arg Ala Gly
    350                 355                 360 gaa gaa ggc tcg atc agg gca gtg gat cat gcc gtg atc ggt ggc gtc   1155
Glu Glu Gly Ser Ile Arg Ala Val Asp His Ala Val Ile Gly Gly Val
365                 370                 375                 380 gtg gcg gtg gtg gtg ttc gcc atg ctg tgc ttg ctc atc att ctg ggg   1203
Val Ala Val Val Val Phe Ala Met Leu Cys Leu Leu Ile Ile Leu Gly
                385                 390                 395 cgc tat ttt gcc aga cat aaa ggt aca tac ttc act cat gaa gcc aaa   1251
Arg Tyr Phe Ala Arg His Lys Gly Thr Tyr Phe Thr His Glu Ala Lys
            400                 405                 410 gga gcc gat gac gca gca gac gca gac aca gct ata atc aat gca gaa   1299
Gly Ala Asp Asp Ala Ala Asp Ala Asp Thr Ala Ile Ile Asn Ala Glu
        415                 420                 425 gga gga cag aac aac tcc gaa gaa aag aaa gag tac ttc atc           1341
Gly Gly Gln Asn Asn Ser Glu Glu Lys Lys Glu Tyr Phe Ile
    430                 435                 440 tagatcagcc tttttgtttc aatgaggtgt ccaactggcc ctatttagat gataaagaga 1401 cagtgatatt ggaacttgcg agaaattcgt gtgttttttt atgaatgggt ggaaaggtgt 1461 gagactggga aggcttggga tttgctgtgt aaaaaaaaaa aaaaaatgtt ctttggaaag 1521 aaaaaagcgg ccgctttctt attctatttc aacattcagc ttaatcataa tcctaaaatc 1581 atacatgcta tttccat                                              1598
```

<210> SEQ ID NO 2
<211> LENGTH: 442
<212> TYPE: PRT
<213> ORGANISM: homo sapiens

<400> SEQUENCE: 2

```
Met Ala Ser Val Val Leu Pro Ser Gly Ser Gln Cys Ala Ala Ala Ala
 1               5                  10                  15

Ala Ala Ala Ala Pro Pro Gly Leu Arg Leu Arg Leu Leu Leu Leu Leu
                20                  25                  30

Phe Ser Ala Ala Ala Leu Ile Pro Thr Gly Asp Gly Gln Asn Leu Phe
            35                  40                  45

Thr Lys Asp Val Thr Val Ile Glu Gly Glu Val Ala Thr Ile Ser Cys
        50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Glu Leu Lys Val Ser Leu Thr
            100                 105                 110

Asn Val Ser Ile Ser Asp Glu Gly Arg Tyr Phe Cys Gln Leu Tyr Thr
            115                 120                 125

Asp Pro Pro Gln Glu Ser Tyr Thr Thr Ile Thr Val Leu Val Pro Pro
        130                 135                 140

Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335

Ile Pro Pro Pro Thr Thr Thr Thr Thr Thr Thr Thr Thr Thr
            340                 345                 350

Thr Ile Leu Thr Ile Ile Thr Asp Ser Arg Ala Gly Glu Glu Gly Ser
        355                 360                 365

Ile Arg Ala Val Asp His Ala Val Ile Gly Gly Val Val Ala Val Val
    370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415
```

```
Ala Ala Asp Ala Asp Thr Ala Ile Ile Asn Ala Glu Gly Gly Gln Asn
        420                 425                 430

Asn Ser Glu Glu Lys Lys Glu Tyr Phe Ile
        435                 440

<210> SEQ ID NO 3
<211> LENGTH: 1935
<212> TYPE: DNA
<213> ORGANISM: mus musculus
<220> FEATURE:
<221> NAME/KEY: CDS
<222> LOCATION: (2)..(1270)

<400> SEQUENCE: 3 g gcg gcg cct cca ggg ctc cgg ctc cgg ctc ctg ctg ttg ctc ctt tcg      49
  Ala Ala Pro Pro Gly Leu Arg Leu Arg Leu Leu Leu Leu Leu Leu Ser
  1               5                   10                  15 gcc gcg gca ctg atc ccc aca ggt gat gga cag aat ctg ttt act aaa       97
Ala Ala Ala Leu Ile Pro Thr Gly Asp Gly Gln Asn Leu Phe Thr Lys
            20                  25                  30 gac gtg aca gtg att gaa gga gaa gtg gca acc atc agc tgc cag gtc      145
Asp Val Thr Val Ile Glu Gly Glu Val Ala Thr Ile Ser Cys Gln Val
        35                  40                  45 aat aag agt gac gac tca gtg atc cag ctc ctg aac ccc aac agg cag      193
Asn Lys Ser Asp Asp Ser Val Ile Gln Leu Leu Asn Pro Asn Arg Gln
    50                  55                  60 acc att tac ttc agg gac ttc agg cct ttg aag gac agc agg ttt cag      241
Thr Ile Tyr Phe Arg Asp Phe Arg Pro Leu Lys Asp Ser Arg Phe Gln
65                  70                  75                  80 ctg ctg aat ttt tct agc agt gaa ctc aaa gtg tca ctg acg aat gtc      289
Leu Leu Asn Phe Ser Ser Ser Glu Leu Lys Val Ser Leu Thr Asn Val
                85                  90                  95 tca atc tcg gat gaa ggg aga tac ttc tgc cag ctc tac acg gac ccc      337
Ser Ile Ser Asp Glu Gly Arg Tyr Phe Cys Gln Leu Tyr Thr Asp Pro
            100                 105                 110 cca cag gag agt tac acc acc atc aca gtc ctg gtt cct cca cgt aac      385
Pro Gln Glu Ser Tyr Thr Thr Ile Thr Val Leu Val Pro Pro Arg Asn
        115                 120                 125 ttg atg atc gat atc cag aaa gac acg gca gtt gaa ggg gag gag att      433
Leu Met Ile Asp Ile Gln Lys Asp Thr Ala Val Glu Gly Glu Glu Ile
    130                 135                 140 gaa gtc aac tgt act gcc atg gcc agc aag cca gcg acg acc atc agg      481
Glu Val Asn Cys Thr Ala Met Ala Ser Lys Pro Ala Thr Thr Ile Arg
145                 150                 155                 160 tgg ttc aaa ggg aac aag gaa ctc aaa ggc aaa tca gag gtg gag gag      529
Trp Phe Lys Gly Asn Lys Glu Leu Lys Gly Lys Ser Glu Val Glu Glu
                165                 170                 175 tgg tcg gac atg tac act gtg acc agt cag ctg atg ctg aag gtg cac      577
Trp Ser Asp Met Tyr Thr Val Thr Ser Gln Leu Met Leu Lys Val His
            180                 185                 190 aag gag gac gac ggg gtc ccg gtg atc tgc cag gtg gag cac cct gcg      625
Lys Glu Asp Asp Gly Val Pro Val Ile Cys Gln Val Glu His Pro Ala
        195                 200                 205 gtc act gga aac ctg cag acc cag cgc tat cta gaa gtg cag tat aaa      673
Val Thr Gly Asn Leu Gln Thr Gln Arg Tyr Leu Glu Val Gln Tyr Lys
    210                 215                 220 ccg caa gtg cat atc cag atg act tac cct ctg caa ggc cta acc cgg      721
Pro Gln Val His Ile Gln Met Thr Tyr Pro Leu Gln Gly Leu Thr Arg
225                 230                 235                 240 gaa ggg gat gca ttt gag tta acg tgt gaa gcc atc ggg aag ccc cag      769
```

-continued

| | | | | | | | | | | | | | | | |
|---|---|---|---|---|---|---|---|---|---|---|---|---|---|---|---|
| Glu | Gly | Asp | Ala | Phe | Glu | Leu | Thr | Cys | Glu | Ala | Ile | Gly | Lys | Pro | Gln |
| | | | 245 | | | | 250 | | | | | 255 | | | |

| cct | gtg | atg | gta | act | tgg | gtg | aga | gtc | gat | gat | gaa | atg | cct | caa | cat | 817 |
|---|---|---|---|---|---|---|---|---|---|---|---|---|---|---|---|---|
| Pro | Val | Met | Val | Thr | Trp | Val | Arg | Val | Asp | Asp | Glu | Met | Pro | Gln | His | |
| | | | 260 | | | | | 265 | | | | 270 | | | | |

| gcc | gta | ctg | tct | ggg | cca | aac | ctg | ttc | atc | aat | aac | cta | aac | aaa | aca | 865 |
|---|---|---|---|---|---|---|---|---|---|---|---|---|---|---|---|---|
| Ala | Val | Leu | Ser | Gly | Pro | Asn | Leu | Phe | Ile | Asn | Asn | Leu | Asn | Lys | Thr | |
| | | | 275 | | | | | 280 | | | | 285 | | | | |

| gat | aac | ggt | act | tac | cgc | tgt | gag | gct | tcc | aac | ata | gtg | gga | aag | gct | 913 |
|---|---|---|---|---|---|---|---|---|---|---|---|---|---|---|---|---|
| Asp | Asn | Gly | Thr | Tyr | Arg | Cys | Glu | Ala | Ser | Asn | Ile | Val | Gly | Lys | Ala | |
| | | 290 | | | | | 295 | | | | 300 | | | | | |

| cat | tcg | gac | tat | atg | ctg | tat | gta | tac | gat | ccc | ccc | aca | act | atc | cct | 961 |
|---|---|---|---|---|---|---|---|---|---|---|---|---|---|---|---|---|
| His | Ser | Asp | Tyr | Met | Leu | Tyr | Val | Tyr | Asp | Pro | Pro | Thr | Thr | Ile | Pro | |
| 305 | | | | | 310 | | | | | 315 | | | | | 320 | |

| cct | ccc | aca | aca | acc | acc | act | acc | acc | acc | acc | acc | acc | atc | | | 1009 |
|---|---|---|---|---|---|---|---|---|---|---|---|---|---|---|---|---|
| Pro | Pro | Thr | Thr | Thr | Thr | Thr | Thr | Thr | Thr | Thr | Thr | Thr | Ile | | | |
| | | | | 325 | | | | | 330 | | | | | 335 | | |

| ctt | acc | atc | atc | aca | gat | tct | cga | gca | ggt | gaa | gag | ggg | acc | att | ggg | 1057 |
|---|---|---|---|---|---|---|---|---|---|---|---|---|---|---|---|---|
| Leu | Thr | Ile | Ile | Thr | Asp | Ser | Arg | Ala | Gly | Glu | Glu | Gly | Thr | Ile | Gly | |
| | | | 340 | | | | | 345 | | | | 350 | | | | |

| gca | gtg | gac | cac | gca | gtg | att | ggt | ggc | gtc | gta | gcc | gtg | gtg | gtg | ttt | 1105 |
|---|---|---|---|---|---|---|---|---|---|---|---|---|---|---|---|---|
| Ala | Val | Asp | His | Ala | Val | Ile | Gly | Gly | Val | Val | Ala | Val | Val | Val | Phe | |
| | | | 355 | | | | | 360 | | | | | 365 | | | |

| gcc | atg | cta | tgc | ttg | ctc | atc | att | ctg | ggc | cgc | tat | ttt | gcc | aga | cat | 1153 |
|---|---|---|---|---|---|---|---|---|---|---|---|---|---|---|---|---|
| Ala | Met | Leu | Cys | Leu | Leu | Ile | Ile | Leu | Gly | Arg | Tyr | Phe | Ala | Arg | His | |
| | | 370 | | | | | 375 | | | | | 380 | | | | |

| aaa | ggt | aca | tac | ttc | act | cat | gaa | gcc | aaa | gga | gcc | gat | gac | gca | gca | 1201 |
|---|---|---|---|---|---|---|---|---|---|---|---|---|---|---|---|---|
| Lys | Gly | Thr | Tyr | Phe | Thr | His | Glu | Ala | Lys | Gly | Ala | Asp | Asp | Ala | Ala | |
| 385 | | | | | 390 | | | | | 395 | | | | | 400 | |

| gac | gca | gac | aca | gct | ata | atc | aat | gca | gaa | gga | gga | cag | aac | aac | tcc | 1249 |
|---|---|---|---|---|---|---|---|---|---|---|---|---|---|---|---|---|
| Asp | Ala | Asp | Thr | Ala | Ile | Ile | Asn | Ala | Glu | Gly | Gly | Gln | Asn | Asn | Ser | |
| | | | | 405 | | | | | 410 | | | | | 415 | | |

| gaa | gaa | aag | aaa | gag | tac | ttc | atctagatca | gccttttgt | tccaatgagg | 1300 |
|---|---|---|---|---|---|---|---|---|---|---|
| Glu | Glu | Lys | Lys | Glu | Tyr | Phe | | | | |
| | | | 420 | | | | | | | | tgtccaactg gcctgtttag atgataaaga gacagtgata ctggaacttt cgagaagctc    1360 gtgtggtttt tgttttgtt ttgttttttt atgagtgggt ggagagatgc gagactggga    1420 aggcttggga tttgcaatgt acaaacaaaa acaaagaatg ttctttgaaa gtacactctg    1480 ctgtttgaca cctctttta atctggtttt aatttgcttt gggttttggg ttttttggt    1540 ttttgtttt tttcatttat atttcttcct accaagtcaa acttgggtac ttggatttgg    1600 tttcggtaga ttgcagaaaa ttctgtgcct tgttttcat tcgtttgttg tgtttcttcc    1660 ctcttgccca tttattttc ccaaaatcaa atttgttttt ttccccctcc caaacctccc    1720 attttttgga attgacctgc tggaattcct aagactttct ccctgttgcc agtttctttt    1780 atttgtgtta acggtgactg ctttctgttc caaattcagt ttcataaaag gaaaaccagc    1840 acaatttaga tttcatagtt cagaatttag tgtctccatg atgcatcctt ctctgttgtt    1900 gtaaagattt gggtgaagaa aaaaaaaaaa aaaa    1935

<210> SEQ ID NO 4
<211> LENGTH: 423
<212> TYPE: PRT
<213> ORGANISM: mus musculus

<400> SEQUENCE: 4

| | | | | | | | | | | | | | | | |
|---|---|---|---|---|---|---|---|---|---|---|---|---|---|---|---|
| Ala | Ala | Pro | Pro | Gly | Leu | Arg | Leu | Arg | Leu | Leu | Leu | Leu | Leu | Leu | Ser |
| 1 | | | | 5 | | | | | 10 | | | | | 15 | |

```
Ala Ala Ala Leu Ile Pro Thr Gly Asp Gly Gln Asn Leu Phe Thr Lys
             20                  25                  30

Asp Val Thr Val Ile Glu Gly Glu Val Ala Thr Ile Ser Cys Gln Val
             35                  40                  45

Asn Lys Ser Asp Asp Ser Val Ile Gln Leu Leu Asn Pro Asn Arg Gln
 50                  55                  60

Thr Ile Tyr Phe Arg Asp Phe Arg Pro Leu Lys Asp Ser Arg Phe Gln
65                   70                  75                  80

Leu Leu Asn Phe Ser Ser Glu Leu Lys Val Ser Leu Thr Asn Val
                 85                  90                  95

Ser Ile Ser Asp Glu Gly Arg Tyr Phe Cys Gln Leu Tyr Thr Asp Pro
                100                 105                 110

Pro Gln Glu Ser Tyr Thr Thr Ile Thr Val Leu Val Pro Pro Arg Asn
                115                 120                 125

Leu Met Ile Asp Ile Gln Lys Asp Thr Ala Val Glu Gly Glu Glu Ile
                130                 135                 140

Glu Val Asn Cys Thr Ala Met Ala Ser Lys Pro Ala Thr Thr Ile Arg
145                 150                 155                 160

Trp Phe Lys Gly Asn Lys Glu Leu Lys Gly Lys Ser Glu Val Glu Glu
                165                 170                 175

Trp Ser Asp Met Tyr Thr Val Thr Ser Gln Leu Met Leu Lys Val His
                180                 185                 190

Lys Glu Asp Asp Gly Val Pro Val Ile Cys Gln Val Glu His Pro Ala
                195                 200                 205

Val Thr Gly Asn Leu Gln Thr Gln Arg Tyr Leu Glu Val Gln Tyr Lys
                210                 215                 220

Pro Gln Val His Ile Gln Met Thr Tyr Pro Leu Gln Gly Leu Thr Arg
225                 230                 235                 240

Glu Gly Asp Ala Phe Glu Leu Thr Cys Glu Ala Ile Gly Lys Pro Gln
                245                 250                 255

Pro Val Met Val Thr Trp Val Arg Val Asp Asp Glu Met Pro Gln His
                260                 265                 270

Ala Val Leu Ser Gly Pro Asn Leu Phe Ile Asn Asn Leu Asn Lys Thr
                275                 280                 285

Asp Asn Gly Thr Tyr Arg Cys Glu Ala Ser Asn Ile Val Gly Lys Ala
                290                 295                 300

His Ser Asp Tyr Met Leu Tyr Val Tyr Asp Pro Pro Thr Thr Ile Pro
305                 310                 315                 320

Pro Pro Thr Thr Thr Thr Thr Thr Thr Thr Thr Thr Thr Thr Thr Ile
                325                 330                 335

Leu Thr Ile Ile Thr Asp Ser Arg Ala Gly Glu Gly Thr Ile Gly
                340                 345                 350

Ala Val Asp His Ala Val Ile Gly Gly Val Val Ala Val Val Val Phe
                355                 360                 365

Ala Met Leu Cys Leu Leu Ile Ile Leu Gly Arg Tyr Phe Ala Arg His
370                 375                 380

Lys Gly Thr Tyr Phe Thr His Glu Ala Lys Gly Ala Asp Asp Ala Ala
385                 390                 395                 400

Asp Ala Asp Thr Ala Ile Ile Asn Ala Glu Gly Gly Gln Asn Asn Ser
                405                 410                 415

Glu Glu Lys Lys Glu Tyr Phe
                420
```

-continued

<210> SEQ ID NO 5
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 5
tatgtcgaca tggcgagtgt agtgctgcc                                       29

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 6
atatagatct atgatccact gccctgatcg                                      30

<210> SEQ ID NO 7
<211> LENGTH: 1820
<212> TYPE: DNA
<213> ORGANISM: homo sapiens
<220> FEATURE:
<221> NAME/KEY: CDS
<222> LOCATION: (157)..(1452)

<400> SEQUENCE: 7
aagcttggca cgaggcggtc cccacctcgg ccccgggctc cgaagcggct cggggcgcc      60 ctttcggtca acatcgtagt ccaccccctc cccatcccca gccccgggg attcaggctc    120 gccagcgccc agccagggag ccggccggga agcgcg atg ggg gcc cca gcc gcc    174
                                       Met Gly Ala Pro Ala Ala
                                         1               5 tcg ctc ctg ctc ctg ctc ctg ttc gcc tgc tgc tgg gcg ccc ggc         222
Ser Leu Leu Leu Leu Leu Leu Phe Ala Cys Cys Trp Ala Pro Gly
         10                  15                  20 ggg gcc aac ctc tcc cag gac ggc tac tgg cag gag cag gat ttg gag    270
Gly Ala Asn Leu Ser Gln Asp Gly Tyr Trp Gln Glu Gln Asp Leu Glu
             25                  30                  35 ctg gga act ctg gct cca ctc gac gag gcc atc agc tcc aca gtc tgg    318
Leu Gly Thr Leu Ala Pro Leu Asp Glu Ala Ile Ser Ser Thr Val Trp
     40                  45                  50 agc agc cct gac atg ctg gcc agt caa gac agc cag ccc tgg aca tct    366
Ser Ser Pro Asp Met Leu Ala Ser Gln Asp Ser Gln Pro Trp Thr Ser
55                  60                  65                  70 gat gaa aca gtg gtg gct ggt ggc acc gtg gtg ctc aag tgc caa gtg    414
Asp Glu Thr Val Val Ala Gly Gly Thr Val Val Leu Lys Cys Gln Val
                 75                  80                  85 aaa gat cac gag gac tca tcc ctg caa tgg tct aac cct gct cag cag    462
Lys Asp His Glu Asp Ser Ser Leu Gln Trp Ser Asn Pro Ala Gln Gln
             90                  95                 100 act ctc tac ttt ggg gag aag aga gcc ctt cga gat aat cga att cag    510
Thr Leu Tyr Phe Gly Glu Lys Arg Ala Leu Arg Asp Asn Arg Ile Gln
        105                 110                 115 ctg gtt acc tct acg ccc cac gag ctc agc atc agc atc agc aat gtg    558
Leu Val Thr Ser Thr Pro His Glu Leu Ser Ile Ser Ile Ser Asn Val
    120                 125                 130 gcc ctg gca gac gag ggc gag tac acc tgc tca atc ttc act atg cct    606
Ala Leu Ala Asp Glu Gly Glu Tyr Thr Cys Ser Ile Phe Thr Met Pro
135                 140                 145                 150

-continued

| | |
|---|---|
| gtg cga act gcc aag tcc ctc gtc act gtg cta gga att cca cag aag<br>Val Arg Thr Ala Lys Ser Leu Val Thr Val Leu Gly Ile Pro Gln Lys<br>                155                    160                  165 | 654 |
| ccc atc atc act ggt tat aaa tct tca tta cgg gaa aaa gac aca gcc<br>Pro Ile Ile Thr Gly Tyr Lys Ser Ser Leu Arg Glu Lys Asp Thr Ala<br>                170                    175                  180 | 702 |
| acc cta aac tgt cag tct tct ggg agc aag cct gca gcc cgg ctc acc<br>Thr Leu Asn Cys Gln Ser Ser Gly Ser Lys Pro Ala Ala Arg Leu Thr<br>            185                    190                  195 | 750 |
| tgg aga aag ggt gac caa gaa ctc cac gga gaa cca acc cgc ata cag<br>Trp Arg Lys Gly Asp Gln Glu Leu His Gly Glu Pro Thr Arg Ile Gln<br>        200                    205                  210 | 798 |
| gaa gat ccc aat ggt aaa acc ttc act gtc agc agc tcg gtg aca ttc<br>Glu Asp Pro Asn Gly Lys Thr Phe Thr Val Ser Ser Ser Val Thr Phe<br>215                    220                  225              230 | 846 |
| cag gtt acc cgg gag gat gat ggg gcg agc atc gtg tgc tct gtg aac<br>Gln Val Thr Arg Glu Asp Asp Gly Ala Ser Ile Val Cys Ser Val Asn<br>                    235                    240                  245 | 894 |
| cat gaa tct cta aag gga gct gac aga tcc acc tct caa cgc att gaa<br>His Glu Ser Leu Lys Gly Ala Asp Arg Ser Thr Ser Gln Arg Ile Glu<br>            250                    255                  260 | 942 |
| gtt tta tac aca cca act gcg atg att agg cca gac cct ccc cat cct<br>Val Leu Tyr Thr Pro Thr Ala Met Ile Arg Pro Asp Pro Pro His Pro<br>        265                    270                  275 | 990 |
| cgt gag ggc cag aag ctg ttg cta cac tgt gag ggt cgc ggc aat cca<br>Arg Glu Gly Gln Lys Leu Leu Leu His Cys Glu Gly Arg Gly Asn Pro<br>        280                    285                  290 | 1038 |
| gtc ccc cag cag tac cta tgg gag aag gag ggc agt gtg cca ccc ctg<br>Val Pro Gln Gln Tyr Leu Trp Glu Lys Glu Gly Ser Val Pro Pro Leu<br>295                    300                  305              310 | 1086 |
| aag atg acc cag gag agt gcc ctg atc ttc cct ttc ctc aac aag agt<br>Lys Met Thr Gln Glu Ser Ala Leu Ile Phe Pro Phe Leu Asn Lys Ser<br>                315                    320                  325 | 1134 |
| gac agt ggc acc tac ggc tgc aca gcc acc agc aac atg ggc agc tac<br>Asp Ser Gly Thr Tyr Gly Cys Thr Ala Thr Ser Asn Met Gly Ser Tyr<br>            330                    335                  340 | 1182 |
| aag gcc tac tac acc ctc aat gtt aat gac ccc agt ccg gtg ccc tcc<br>Lys Ala Tyr Tyr Thr Leu Asn Val Asn Asp Pro Ser Pro Val Pro Ser<br>        345                    350                  355 | 1230 |
| tcc tcc agc acc tac cac gcc atc atc ggt ggg atc gtg gct ttc att<br>Ser Ser Ser Thr Tyr His Ala Ile Ile Gly Gly Ile Val Ala Phe Ile<br>        360                    365                  370 | 1278 |
| gtc ttc ctg ctg ctc atc atg ctc atc ttc ctt ggc cac tac ttg atc<br>Val Phe Leu Leu Leu Ile Met Leu Ile Phe Leu Gly His Tyr Leu Ile<br>375                    380                  385              390 | 1326 |
| cgg cac aaa gga acc tac ctg aca cat gag gca aaa ggc tcc gac gat<br>Arg His Lys Gly Thr Tyr Leu Thr His Glu Ala Lys Gly Ser Asp Asp<br>                395                    400                  405 | 1374 |
| gct cca gac gcg gac acg gcc atc atc aat gca gaa ggc ggg cag tca<br>Ala Pro Asp Ala Asp Thr Ala Ile Ile Asn Ala Glu Gly Gly Gln Ser<br>            410                    415                  420 | 1422 |
| gga ggg gac gac aag aag gaa tat ttc atc tagaggcgcc tgcccacttc<br>Gly Gly Asp Asp Lys Lys Glu Tyr Phe Ile<br>        425                    430 | 1472 |
| ctgcgccccc cagggccct gtggggactg ctggggccgt caccaacccg gacttgtaca | 1532 |
| gagcaaccgc agggccgccc ctcccgcttg ctccccagcc cacccacccc cctgtacaga | 1592 |
| atgtctgctt tggtgcggt tttgtactcg gtttggaatg gggagggagg agggcggggg | 1652 |
| gaggggaggg ttgccctcag cccttttccgt ggcttctctg catttggggtt attattattt | 1712 |

```
ttgtaacaat cccaaatcaa atctgtctcc aggctggaga ggcaggagcc ctggggtgag    1772
aaaagcaaaa aacaaacaaa aaaaaaaaaa aaaaattcct gcggccgc                1820
```

<210> SEQ ID NO 8
<211> LENGTH: 432
<212> TYPE: PRT
<213> ORGANISM: homo sapiens
<400> SEQUENCE: 8

```
Met Gly Ala Pro Ala Ala Ser Leu Leu Leu Leu Leu Leu Leu Phe Ala
1               5                   10                  15

Cys Cys Trp Ala Pro Gly Gly Ala Asn Leu Ser Gln Asp Gly Tyr Trp
            20                  25                  30

Gln Glu Gln Asp Leu Glu Leu Gly Thr Leu Ala Pro Leu Asp Glu Ala
        35                  40                  45

Ile Ser Ser Thr Val Trp Ser Ser Pro Asp Met Leu Ala Ser Gln Asp
    50                  55                  60

Ser Gln Pro Trp Thr Ser Asp Glu Thr Val Val Ala Gly Gly Thr Val
65                  70                  75                  80

Val Leu Lys Cys Gln Val Lys Asp His Glu Asp Ser Ser Leu Gln Trp
                85                  90                  95

Ser Asn Pro Ala Gln Gln Thr Leu Tyr Phe Gly Glu Lys Arg Ala Leu
            100                 105                 110

Arg Asp Asn Arg Ile Gln Leu Val Thr Ser Thr Pro His Glu Leu Ser
        115                 120                 125

Ile Ser Ile Ser Asn Val Ala Leu Ala Asp Glu Gly Glu Tyr Thr Cys
    130                 135                 140

Ser Ile Phe Thr Met Pro Val Arg Thr Ala Lys Ser Leu Val Thr Val
145                 150                 155                 160

Leu Gly Ile Pro Gln Lys Pro Ile Ile Thr Gly Tyr Lys Ser Ser Leu
                165                 170                 175

Arg Glu Lys Asp Thr Ala Thr Leu Asn Cys Gln Ser Ser Gly Ser Lys
            180                 185                 190

Pro Ala Ala Arg Leu Thr Trp Arg Lys Gly Asp Gln Glu Leu His Gly
        195                 200                 205

Glu Pro Thr Arg Ile Gln Glu Asp Pro Asn Gly Lys Thr Phe Thr Val
    210                 215                 220

Ser Ser Ser Val Thr Phe Gln Val Thr Arg Glu Asp Asp Gly Ala Ser
225                 230                 235                 240

Ile Val Cys Ser Val Asn His Glu Ser Leu Lys Gly Ala Asp Arg Ser
                245                 250                 255

Thr Ser Gln Arg Ile Glu Val Leu Tyr Thr Pro Thr Ala Met Ile Arg
            260                 265                 270

Pro Asp Pro Pro His Pro Arg Glu Gly Gln Lys Leu Leu Leu His Cys
        275                 280                 285

Glu Gly Arg Gly Asn Pro Val Pro Gln Gln Tyr Leu Trp Glu Lys Glu
    290                 295                 300

Gly Ser Val Pro Pro Leu Lys Met Thr Gln Glu Ser Ala Leu Ile Phe
305                 310                 315                 320

Pro Phe Leu Asn Lys Ser Asp Ser Gly Thr Tyr Gly Cys Thr Ala Thr
                325                 330                 335

Ser Asn Met Gly Ser Tyr Lys Ala Tyr Tyr Thr Leu Asn Val Asn Asp
            340                 345                 350
```

```
Pro Ser Pro Val Pro Ser Ser Ser Thr Tyr His Ala Ile Ile Gly
        355                 360                 365

Gly Ile Val Ala Phe Ile Val Phe Leu Leu Ile Met Leu Ile Phe
        370                 375                 380

Leu Gly His Tyr Leu Ile Arg His Lys Gly Thr Tyr Leu Thr His Glu
385                 390                 395                 400

Ala Lys Gly Ser Asp Asp Ala Pro Asp Ala Asp Thr Ala Ile Ile Asn
                405                 410                 415

Ala Glu Gly Gly Gln Ser Gly Gly Asp Asp Lys Lys Glu Tyr Phe Ile
                420                 425                 430

<210> SEQ ID NO 9
<211> LENGTH: 1718
<212> TYPE: DNA
<213> ORGANISM: homo sapiens
<220> FEATURE:
<221> NAME/KEY: CDS
<222> LOCATION: (157)..(1350)

<400> SEQUENCE: 9
aagcttggca cgaggcggtc cccacctcgg ccccgggctc cgaagcggct cggggggcgcc     60 ctttcggtca acatcgtagt ccaccccctc cccatcccca gccccggggg attcaggctc    120
gccagcgccc agccagggag ccggccggga agcgcg atg ggg gcc cca gcc gcc      174
                                        Met Gly Ala Pro Ala Ala
                                          1               5 tcg ctc ctg ctc ctg ctc ctg ttc gcc tgc tgc tgg gcg ccc ggc          222
Ser Leu Leu Leu Leu Leu Leu Leu Phe Ala Cys Cys Trp Ala Pro Gly
            10                  15                  20 ggg gcc aac ctc tcc cag gac gac agc cag ccc tgg aca tct gat gaa      270
Gly Ala Asn Leu Ser Gln Asp Asp Ser Gln Pro Trp Thr Ser Asp Glu
        25                  30                  35 aca gtg gtg gct ggt ggc acc gtg gtg ctc aag tgc caa gtg aaa gat      318
Thr Val Val Ala Gly Gly Thr Val Val Leu Lys Cys Gln Val Lys Asp
    40                  45                  50 cac gag gac tca tcc ctg caa tgg tct aac cct gct cag cag act ctc      366
His Glu Asp Ser Ser Leu Gln Trp Ser Asn Pro Ala Gln Gln Thr Leu
55                  60                  65                  70 tac ttt ggg gag aag aga gcc ctt cga gat aat cga att cag ctg gtt      414
Tyr Phe Gly Glu Lys Arg Ala Leu Arg Asp Asn Arg Ile Gln Leu Val
                75                  80                  85 acc tct acg ccc cac gag ctc agc atc agc atc agc aat gtg gcc ctg      462
Thr Ser Thr Pro His Glu Leu Ser Ile Ser Ile Ser Asn Val Ala Leu
            90                  95                 100 gca gac gag ggc gag tac acc tgc tca atc ttc act atg cct gtg cga      510
Ala Asp Glu Gly Glu Tyr Thr Cys Ser Ile Phe Thr Met Pro Val Arg
        105                 110                 115 act gcc aag tcc ctc gtc act gtg cta gga att cca cag aag ccc atc      558
Thr Ala Lys Ser Leu Val Thr Val Leu Gly Ile Pro Gln Lys Pro Ile
    120                 125                 130 atc act ggt tat aaa tct tca tta cgg gaa aaa gac aca gcc acc cta      606
Ile Thr Gly Tyr Lys Ser Ser Leu Arg Glu Lys Asp Thr Ala Thr Leu
135                 140                 145                 150 aac tgt cag tct tct ggg agc aag cct gca gcc cgg ctc acc tgg aga      654
Asn Cys Gln Ser Ser Gly Ser Lys Pro Ala Ala Arg Leu Thr Trp Arg
                155                 160                 165 aag ggt gac caa gaa ctc cac gga gaa cca acc cgc ata cag gaa gat      702
Lys Gly Asp Gln Glu Leu His Gly Glu Pro Thr Arg Ile Gln Glu Asp
            170                 175                 180 ccc aat ggt aaa acc ttc act gtc agc agc tcg gtg aca ttc cag gtt      750
```

```
                                                         -continued

Pro Asn Gly Lys Thr Phe Thr Val Ser Ser Ser Val Thr Phe Gln Val
        185                 190                 195 acc cgg gag gat gat ggg gcg agc atc gtg tgc tct gtg aac cat gaa       798
Thr Arg Glu Asp Asp Gly Ala Ser Ile Val Cys Ser Val Asn His Glu
    200                 205                 210 tct cta aag gga gct gac aga tcc acc tct caa cgc att gaa gtt tta       846
Ser Leu Lys Gly Ala Asp Arg Ser Thr Ser Gln Arg Ile Glu Val Leu
215                 220                 225                 230 tac aca cca act gcg atg att agg cca gac cct ccc cat cct cgt gag       894
Tyr Thr Pro Thr Ala Met Ile Arg Pro Asp Pro Pro His Pro Arg Glu
                235                 240                 245 ggc cag aag ctg ttg cta cac tgt gag ggt cgc ggc aat cca gtc ccc       942
Gly Gln Lys Leu Leu Leu His Cys Glu Gly Arg Gly Asn Pro Val Pro
            250                 255                 260 cag cag tac cta tgg gag aag gag ggc agt gtg cca ccc ctg aag atg       990
Gln Gln Tyr Leu Trp Glu Lys Glu Gly Ser Val Pro Pro Leu Lys Met
        265                 270                 275 acc cag gag agt gcc ctg atc ttc cct ttc ctc aac aag agt gac agt      1038
Thr Gln Glu Ser Ala Leu Ile Phe Pro Phe Leu Asn Lys Ser Asp Ser
    280                 285                 290 ggc acc tac ggc tgc aca gcc acc agc aac atg ggc agc tac aag gcc      1086
Gly Thr Tyr Gly Cys Thr Ala Thr Ser Asn Met Gly Ser Tyr Lys Ala
295                 300                 305                 310 tac tac acc ctc aat gtt aat gac ccc agt ccg gtg ccc tcc tcc tcc      1134
Tyr Tyr Thr Leu Asn Val Asn Asp Pro Ser Pro Val Pro Ser Ser Ser
                315                 320                 325 agc acc tac cac gcc atc atc ggt ggg atc gtg gct ttc att gtc ttc      1182
Ser Thr Tyr His Ala Ile Ile Gly Gly Ile Val Ala Phe Ile Val Phe
            330                 335                 340 ctg ctg ctc atc atg ctc atc ttc ctt ggc cac tac ttg atc cgg cac      1230
Leu Leu Leu Ile Met Leu Ile Phe Leu Gly His Tyr Leu Ile Arg His
        345                 350                 355 aaa gga acc tac ctg aca cat gag gca aaa ggc tcc gac gat gct cca      1278
Lys Gly Thr Tyr Leu Thr His Glu Ala Lys Gly Ser Asp Asp Ala Pro
    360                 365                 370 gac gcg gac acg gcc atc atc aat gca gaa ggc ggg cag tca gga ggg      1326
Asp Ala Asp Thr Ala Ile Ile Asn Ala Glu Gly Gly Gln Ser Gly Gly
375                 380                 385                 390 gac gac aag aag gaa tat ttc atc tagaggcgcc tgcccacttc ctgcgccccc     1380
Asp Asp Lys Lys Glu Tyr Phe Ile
                395 cagggccct gtggggactg ctggggccgt caccaacccg gacttgtaca gagcaaccgc     1440
agggccgccc ctcccgcttg ctccccagcc cacccacccc cctgtacaga atgtctgctt   1500
tgggtgcggt tttgtactcg gtttggaatg gggaggagg agggcggggg gaggggaggg    1560
ttgccctcag cccttttccgt ggcttctctg catttgggtt attattattt ttgtaacaat  1620
cccaaatcaa atctgtctcc aggctggaga ggcaggagcc ctggggtgag aaaagcaaaa   1680
aacaaacaaa aaaaaaaaaa aaaattcct gcggccgc                            1718

<210> SEQ ID NO 10
<211> LENGTH: 398
<212> TYPE: PRT
<213> ORGANISM: homo sapiens

<400> SEQUENCE: 10

Met Gly Ala Pro Ala Ala Ser Leu Leu Leu Leu Leu Leu Leu Phe Ala
1               5                   10                  15

Cys Cys Trp Ala Pro Gly Gly Ala Asn Leu Ser Gln Asp Asp Ser Gln
```

```
                      20                  25                  30
Pro Trp Thr Ser Asp Glu Thr Val Ala Gly Gly Thr Val Val Leu
             35                  40                  45
Lys Cys Gln Val Lys Asp His Glu Asp Ser Ser Leu Gln Trp Ser Asn
 50                  55                  60
Pro Ala Gln Gln Thr Leu Tyr Phe Gly Glu Lys Arg Ala Leu Arg Asp
 65                  70                  75                  80
Asn Arg Ile Gln Leu Val Thr Ser Thr Pro His Glu Leu Ser Ile Ser
                 85                  90                  95
Ile Ser Asn Val Ala Leu Ala Asp Glu Gly Glu Tyr Thr Cys Ser Ile
                100                 105                 110
Phe Thr Met Pro Val Arg Thr Ala Lys Ser Leu Val Thr Val Leu Gly
                115                 120                 125
Ile Pro Gln Lys Pro Ile Ile Thr Gly Tyr Lys Ser Ser Leu Arg Glu
                130                 135                 140
Lys Asp Thr Ala Thr Leu Asn Cys Gln Ser Ser Gly Ser Lys Pro Ala
145                 150                 155                 160
Ala Arg Leu Thr Trp Arg Lys Gly Asp Gln Glu Leu His Gly Glu Pro
                165                 170                 175
Thr Arg Ile Gln Glu Asp Pro Asn Gly Lys Thr Phe Thr Val Ser Ser
                180                 185                 190
Ser Val Thr Phe Gln Val Thr Arg Glu Asp Asp Gly Ala Ser Ile Val
                195                 200                 205
Cys Ser Val Asn His Glu Ser Leu Lys Gly Ala Asp Arg Ser Thr Ser
210                 215                 220
Gln Arg Ile Glu Val Leu Tyr Thr Pro Thr Ala Met Ile Arg Pro Asp
225                 230                 235                 240
Pro Pro His Pro Arg Glu Gly Gln Lys Leu Leu Leu His Cys Glu Gly
                245                 250                 255
Arg Gly Asn Pro Val Pro Gln Gln Tyr Leu Trp Glu Lys Glu Gly Ser
                260                 265                 270
Val Pro Pro Leu Lys Met Thr Gln Glu Ser Ala Leu Ile Phe Pro Phe
                275                 280                 285
Leu Asn Lys Ser Asp Ser Gly Thr Tyr Gly Cys Thr Ala Thr Ser Asn
290                 295                 300
Met Gly Ser Tyr Lys Ala Tyr Tyr Thr Leu Asn Val Asn Asp Pro Ser
305                 310                 315                 320
Pro Val Pro Ser Ser Ser Thr Tyr His Ala Ile Ile Gly Gly Ile
                325                 330                 335
Val Ala Phe Ile Val Phe Leu Leu Leu Ile Met Leu Ile Phe Leu Gly
                340                 345                 350
His Tyr Leu Ile Arg His Lys Gly Thr Tyr Leu Thr His Glu Ala Lys
                355                 360                 365
Gly Ser Asp Asp Ala Pro Asp Ala Asp Thr Ala Ile Ile Asn Ala Glu
                370                 375                 380
Gly Gly Gln Ser Gly Gly Asp Lys Lys Glu Tyr Phe Ile
385                 390                 395

<210> SEQ ID NO 11
<211> LENGTH: 393
<212> TYPE: PRT
<213> ORGANISM: homo sapiens

<400> SEQUENCE: 11
```

```
Met Trp Trp Arg Val Leu Ser Leu Leu Ala Trp Phe Pro Leu Gln Glu
1               5                   10                  15

Ala Ser Leu Thr Asn His Thr Glu Thr Ile Thr Val Glu Glu Gly Gln
            20                  25                  30

Thr Leu Thr Leu Lys Cys Val Thr Ser Leu Arg Lys Asn Ser Ser Leu
            35                  40                  45

Gln Trp Leu Thr Pro Ser Gly Phe Thr Ile Phe Leu Asn Glu Tyr Pro
50                      55                  60

Ala Leu Lys Asn Ser Lys Tyr Gln Leu Leu His His Ser Ala Asn Gln
65                  70                  75                  80

Leu Ser Ile Thr Val Pro Asn Val Thr Leu Gln Asp Glu Gly Val Tyr
                85                  90                  95

Lys Cys Leu His Tyr Ser Asp Ser Val Ser Thr Lys Glu Val Lys Val
                100                 105                 110

Ile Val Leu Ala Thr Pro Phe Lys Pro Ile Leu Glu Ala Ser Val Ile
                115                 120                 125

Arg Lys Gln Asn Gly Glu Glu His Val Val Leu Met Cys Ser Thr Met
            130                 135                 140

Arg Ser Lys Pro Pro Gln Ile Thr Trp Leu Leu Gly Asn Ser Met Met
145                 150                 155                 160

Glu Val Ser Gly Gly Thr Leu His Glu Phe Glu Thr Asp Gly Lys Lys
                165                 170                 175

Cys Asn Thr Thr Ser Thr Leu Ile Ile Leu Ser Tyr Gly Lys Asn Ser
                180                 185                 190

Thr Val Asp Cys Ile Ile Arg His Arg Gly Leu Gln Gly Arg Lys Leu
            195                 200                 205

Val Ala Pro Phe Arg Phe Glu Asp Leu Val Thr Asp Glu Glu Thr Ala
210                 215                 220

Ser Asp Ala Leu Glu Arg Asn Ser Leu Ser Thr Gln Asp Pro Gln Gln
225                 230                 235                 240

Pro Thr Ser Thr Val Ser Val Thr Glu Asp Ser Ser Thr Ser Glu Ile
                245                 250                 255

Asp Lys Glu Glu Lys Glu Gln Thr Thr Gln Asp Pro Asp Leu Thr Thr
            260                 265                 270

Glu Ala Asn Pro Gln Tyr Leu Gly Leu Ala Arg Lys Lys Ser Gly Ile
            275                 280                 285

Leu Leu Leu Thr Leu Val Ser Phe Leu Ile Phe Ile Leu Phe Ile Ile
            290                 295                 300

Val Gln Leu Phe Ile Met Lys Leu Arg Lys Ala His Val Ile Trp Lys
305                 310                 315                 320

Arg Glu Asn Glu Val Ser Glu His Thr Leu Glu Ser Tyr Arg Ser Arg
                325                 330                 335

Ser Asn Asn Glu Glu Thr Ser Ser Glu Glu Lys Asn Gly Gln Ser Ser
                340                 345                 350

Leu Pro Met Arg Cys Met Asn Tyr Ile Thr Lys Leu Tyr Ser Glu Ala
            355                 360                 365

Lys Thr Lys Arg Lys Glu Asn Val Gln His Ser Lys Leu Glu Glu Lys
            370                 375                 380

His Ile Gln Val Pro Glu Ser Ile Val
385                 390

<210> SEQ ID NO 12
<211> LENGTH: 115
<212> TYPE: PRT
```

-continued

```
<213> ORGANISM: homo sapiens

<400> SEQUENCE: 12

Gln Val Gln Leu Val Gln Trp Gly Ala Gly Leu Leu Lys Pro Ser Glu
1               5                   10                  15

Thr Leu Ser Leu Thr Cys Ala Val Tyr Gly Gly Ser Phe Ser Gly His
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Arg Leu Asn Ser Val Thr Ala Ala Asp Thr Ala Val Tyr Tyr Cys Ala
                85                  90                  95

Arg Val Ser Trp Tyr Phe Asp Leu Trp Gly Lys Gly Thr Leu Val Thr
            100                 105                 110

Val Ser Ser
        115

<210> SEQ ID NO 13
<211> LENGTH: 104
<212> TYPE: PRT
<213> ORGANISM: homo sapiens

<400> SEQUENCE: 13

Pro Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ser Gly Ser Ser Ser Gly Asn Thr Ala
    50                  55                  60

Ser Leu Thr Ile Thr Gly Ala Gln Ala Glu Asp Glu Ala Asp Tyr Tyr
65                  70                  75                  80

Cys Asn Ser Arg Asp Ser Ser Ser Thr His Arg Gly Val Phe Gly Gly
                85                  90                  95

Gly Thr Lys Leu Thr Val Leu Gly
            100
```

US 7,267,960 B2

ANTAGONISTS AND AGONISTS OF LDCAM AND METHODS OF USE

CROSS REFERENCE TO RELATED APPLICATIONS

This application claims the benefit under 35 U.S.C. §119 of U.S. Provisional Application Ser. No. 60/490,027, filed Jul. 25, 2003.

BACKGROUND

1. Field of the Invention

Embodiments of the invention generally pertain to agonists and antagonists of LDCAM, as well as methods of treating disease by administering one or more LDCAM antagonists or agonists.

2. Description of Related Art

LDCAM is a homophilic cell adhesion molecule that has been shown to modulate T-cell function by interacting with one or more T-cell surface molecules thereby causing alteration of cellular signaling. LDCAM was shown to self-associate to form a homodimer and bind to B7L-1. LDCAM was also shown to generate increases in natural killer cell populations. U.S. patent application Ser. No. 09/778,187, filed Feb. 6, 2001, describes LDCAM and is incorporated herein by reference in its entirety.

LDCAM is also referred to in the art as Igsf4, TSLC1, SynCAM and Nectin-Like-2 and has been characterized as a member of the Nectin-like family of immunoglobulin-like cell surface receptors and as having three C2 Ig-like domains. The cytoplasmic tail of Nectin-like receptors has a band-4.1 protein binding site and a PDZ-protein binding site. LDCAM has been identified as a tumor suppressor gene deleted in non-small cell lung carcinoma and having homology to NCAM (Gomyo et al. Genomics 62:139-146 (1999) and Kuramochi et al. Nat Genet 27(4):427-30 (2001) Masuda et al. J Biol Chem. 277(34):31014-9 (2002)).

As described herein, it has been discovered that LDCAM binds to CRTAM. CRTAM has been described as a member of a family of cell surface markers initially designated as a class I-restricted T cell-associated molecule (CRTAM) as a result of its restricted expression pattern in T cells (U.S. Pat. No. 5,686,257). cDNA library subtraction techniques showed that mRNA transcripts were expressed by activated mouse alphabetaTCR+ CD4-CD8-(double-negative) T cells, a subset of natural killer T (NKT) cells. Human CRTAM has also been identified, and shares the same expression pattern as the mouse molecule. LPTN and CRTAM exhibit the same expression pattern in T cells, suggesting the existence of a gene expression program common to class I-MHC-restricted T cells (Kennedy, et al., *J Leuk Bio* 67, 725 (2000)).

SUMMARY OF THE INVENTION

Embodiments of the present invention provide antagonists and agonists of LDCAM. In one embodiment, LDCAM agonists and LDCAM antagonists bind to LDCAM. In alternative embodiments, LDCAM agonists and LDCAM antagonists may bind to one of LDCAM's binding partners, which includes, but is not limited to, LDCAM, CRTAM and B7L-1. LDCAM agonists and antagonists include soluble LDCAM polypeptides, as well as biologically active fragments and variants thereof, fusion proteins, derivatives, and the like. LDCAM agonists and antagonists also include all forms of antibodies, peptibodies and intrabodies directed against LDCAM or its binding partners.

Aspects of the present invention are drawn to the discovery of a new subset of human dendritic cells (BDCA3+) that are the human counterpart of mouse CD8α+ dendritic cells. This subset of dendritic cells represent a unique immuno-regulating antigen presenting cells in that they are responsible for antigen cross-presentation, cross-priming and also cross-tolerance.

One particular embodiment comprises an antibody having the sequence provided in FIG. 6. The LDCAM-specific scfv may take the form of various embodiments, as described in more detail below, which includes a scfv-Fc fusion protein.

Another binding partner of LDCAM has been discovered. LDCAM binds to CRTAM, which is expressed at high levels on activated T-cells, NK cells and NK-T cells. Therefore, embodiments of the invention include agonists and antagonists of the interaction or binding of LDCAM and CRTAM.

Additional embodiments are described in detail below.

BRIEF DESCRIPTION OF THE FIGURES

FIG. 2 is a table of genes shared between mouse CD8α+ dendritic cells and human BDCA3+ dendritic cells.

FIG. 6 is the amino acid sequence for the variable regions of the heavy and light chains for the 1F12 scfv (anti-LDCAM scfv).

FIGS. 9B, 9D, 9F and 9H show that CD8+ T-cells were were anergized by LDCAM to activation by anti-CD3 mAb, conA, PHA and conA + IL-2, respectively. These studies show that LDCAM is interacting with a molecule expressed on the surface of activated T-cells in a contact-dependent nature that prevents or dampens the activation of T-cells by a variety of stimuli. Theses studies show that LDCAM is a regulatory agent in inflammatory pathways.

FIGS. 13A and 13B are a gel from an immunoprecipitation. FIG. 13A is the band immunoprecipitated by LDCAM-Fc from activated CTL. FIG. 13B is the band immunoprecipitated by 1F12 scfv-Fc from the bone marrow-derived DC. Similar results were obtained with splenic CD8+ DC. The band from FIG. 13A was excised and analyzed by mass spectrometry, which confirm that CRTAM is the cognate of LDCAM

FIG. 15 represents a FACS assay illustrating that EL4 cells transduced with a lentivirus vector to express LDCAM (FIG. 15A) or Necl1 (FIG. 15B) on their cell surface. The transduced cells were exposed to soluble recombinant human CRTAM-Fc.

DETAILED DESCRIPTION OF THE INVENTION

1. Definitions

Figure 1:
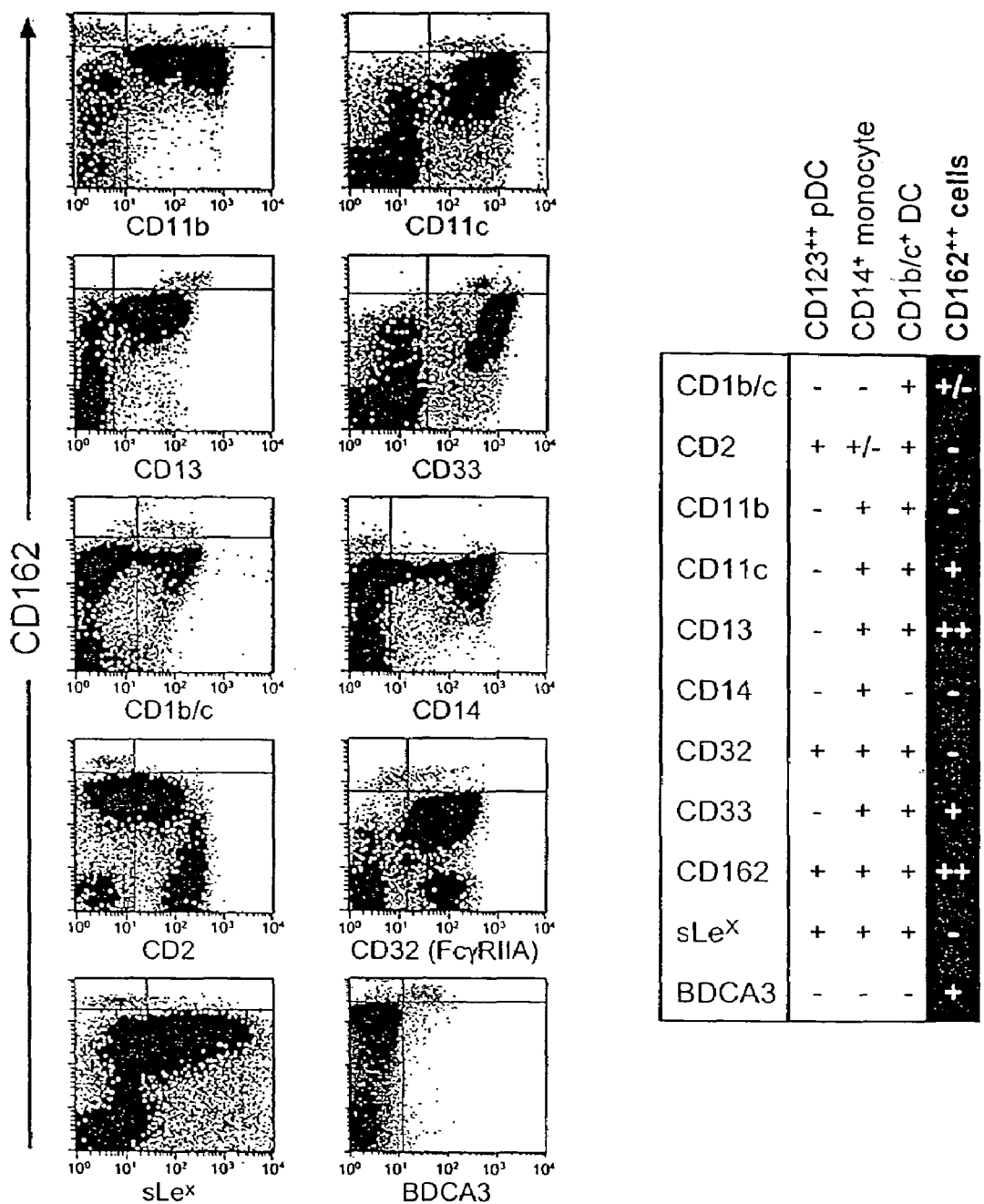
FIG. 1 shows the phenotyping of a new subset of human dendritic cells that are the human counterpart of mouse CD8α+ dendritic cells, which are critical immunomodulating antigen presenting cells for cross-presentation and cross-tolerance.

LDCAM is defined and described in the section below.

CRTAM is defined and described in U.S. Pat. No. 5,686,257, which is incorporated herein by reference in its entirety.

A "LDCAM binding partner" or "LDCAM cognate" is a cognate of LDCAM and includes, but is not limited to, LDCAM (by homotypic aggregation or association—cis and/or trans), CRTAM, B7L-1 (Necl-1), and B7L-4 (Nectin-3).

The term "biologically active" as it relates to LDCAM, means that the LDCAM is capable of one or more of the following activities: LDCAM-to-LDCAM binding (such as by homotypic association—cis and/or trans); binding to CRTAM; binding to B7L-1; binding to B7L-4 (Nectin-3); modulating T-cell activity, such as preventing activation and proliferation; decreasing release of proinflammatory cytokines, such as but not limted to Interferon-gamma and IL-2; modulating T-cell responses to activation stimuli; modulating T-cell responses to CD3 stimulation/acitivation; modulating T-cell responses to mitogen stimulation/acitivation; modulating NK-T-cell activity; modulating NK cell activity; modulating B-cell activity; modulating cytokine expression by immune cells, such as, but not limited to, IL-2, INF-gamma and other pro-inflammatory cytokines; modulating activity between antigen presenting cells and T-cells; modulating activity between dendritic cells and T-cells; modulating activity between BDCA3+ dendritic cells and T-cells; modulating activity between antigen presenting cells and NK-T-cells; modulating activity between dendritic cells and NK-T-cells; modulating activity between BDCA3+ dendritic cells and NK-T-cells; modulating activity between antigen presenting cells and NK cells; modulating activity between dendritic cells and NK cells; modulating activity between BDCA3+ dendritic cells and NK cells; modulating activity between neurons and T-cells; modulating activity between neurons and NK-T-cells; and modulating activity between neurons and NK cells.

Activating or activation of a receptor is defined herein as the engagement of one or more intracellular signaling pathway(s) and the transduction of intracellular signaling (i.e., signal transduction) in response to a molecule binding to a membrane-bound receptor, such as but not limited to, a receptor:ligand interaction.

"Signal transduction," as used herein, is the relaying of a signal by conversion from one physical or chemical form to another. In cell biology, the process by which a cell converts an extracellular signal into a response.

A "peptibody," in general, refers to molecules comprising at least part of an immunoglobulin Fc domain and at least one peptide. Such peptibodies may be multimers or dimers or fragments thereof, and they may be derivatized. Peptibodies are known in the art and are described in greater detail in WO 99/25044 and WO 00/24782, which are incorporated herein by reference in their entirety. The peptide may be from the amino acid sequence of LDCAM B7L-1 or CRTAM.

A "peptide," as used herein refers to molecules of 1 to 100 amino acids. Alternative embodiments comprise molecules of 5 to 20 amino acids. Exemplary peptides may comprise portions of the extracellular domain of naturally occurring molecules or comprise randomized sequences of LDCAM, B7L-1 or CRTAM.

The term "randomized" as used to refer to peptide sequences refers to fully random sequences (e.g., selected by phage display methods or RNA-peptide screening) and sequences in which one or more residues of a naturally occurring molecule is replaced by an amino acid residue not appearing in that position in the naturally occurring molecule. Exemplary methods for identifying peptide sequences include phage display, *E. coli* display, ribosome display, RNA-peptide screening, chemical screening, and the like.

The term "Fc domain" encompasses native Fc and Fc variant molecules and sequences as defined below. As with Fc variants and native Fc's, the term "Fc domain" includes molecules in monomeric or multimeric form, whether digested from whole antibody or produced by other means.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res*. 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference in their entirety. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

A "peptidomimetic" is a peptide analog that displays more favorable pharmacological properties than their prototype native peptides, such as a) metabolic stability, b) good bioavailability, c) high receptor affinity and receptor selectivity, and d) minimal side effects. Designing peptidomimetics and methods of producing the same are known in the art (see for example, U.S. Pat. Nos. 6,407,059 and 6,420,118). Peptidomimetics may be derived from the binding site of the extracellular domain of LDCAM, B7L-1 or CRTAM. In alternative embodiments, a peptidomimetic comprises non-peptide compounds having the same three-dimensional structure as peptides derived from LDCAM, B7L-1 or CRTAM, or compounds in which part of a peptide from the molecules listed above is replaced by a non-peptide moiety having the same three-dimensional structure.

A "mimotope" is defined herein as peptide sequences that mimic binding sites on proteins (see, Partidos, CD, et al., *Combinatorial Chem & High Throughput Screening*, 2002 5:15-27). A mimotope may have the capacity to mimic a conformationally-dependent binding site of a protein. The sequences of these mimotopes do not identify a continuous linear native sequence or necessarily occur in a naturally-occurring protein. Mimotpes and methods of production are taught in U.S. Pat. No. 5,877,155 and U.S. Pat. No. 5,998, 577, which are incorporated by reference in their entireties.

The term "acidic residue" refers to amino acid residues in D- or L-form having sidechains comprising acidic groups. Exemplary acidic residues include D and E.

The term "amide residue" refers to amino acids in D- or L-form having sidechains comprising amide derivatives of acidic groups. Exemplary residues include N and Q.

The term "aromatic residue" refers to amino acid residues in D- or L-form having sidechains comprising aromatic groups. Exemplary aromatic residues include F, Y, and W.

The term "basic residue" refers to amino acid residues in D- or L-form having sidechains comprising basic groups. Exemplary basic residues include H, K, and R.

The term "hydrophilic residue" refers to amino acid residues in D- or L-form having sidechains comprising polar groups. Exemplary hydrophilic residues include C, S, T, N, and Q.

The term "nonfunctional residue" refers to amino acid residues in D- or L-form having sidechains that lack acidic, basic, or aromatic groups. Exemplary nonfunctional amino acid residues include M, G, A, V, I, L and norleucine (Nle).

The term "neutral hydrophobic residue" refers to amino acid residues in D- or L-form having sidechains that lack basic, acidic, or polar groups. Exemplary neutral hydrophobic amino acid residues include A, V, L, I, P, W, M, and F.

The term "polar hydrophobic residue" refers to amino acid residues in D- or L-form having sidechains comprising polar groups. Exemplary polar hydrophobic amino acid residues include T, G, S, Y, C, Q, and N.

The term "hydrophobic residue" refers to amino acid residues in D- or L-form having sidechains that lack basic or acidic groups. Exemplary hydrophobic amino acid residues include A, V, L, I, P, W, M, F, T, G, S, Y, C, Q, and N.

The term "subject" as used herein, refers to mammals. For example, mammals contemplated by the present invention include humans; primates; pets of all sorts, such as dogs, cats, etc.; domesticated animals, such as, sheep, cattle, goats, pigs, horses and the like; common laboratory animals, such as mice, rats, rabbits, guinea pigs, etc.; as well as captive animals, such as in a zoo or free wild animals. Throughout the specification, the term host is used interchangeably with subject.

"Isolated" means that LDCAM, a LDCAM antagonist or a LDCAM agonist is free of association with other proteins or polypeptides, for example, as a purification product of recombinant host cell culture or as a purified extract.

As used herein the singular forms "a", "and", and "the" include plural referents unless the context clearly dictates otherwise. Thus, for example, reference to "an immunization"includes a plurality of such immunizations and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

For clarity, other definitions are provided throughout the specification in order to keep the term in the proper context of the description.

It is understood that the various embodiments of this invention are not limited to the particular methodology, protocols, cell lines, animal species or genera, constructs, and reagents described, as such may vary. It is also understood that the terminology used herein is for the purpose of describing particular embodiments only, and is not intended to limit the scope of the present invention which will be limited only by the appended claims.

2. Antagonists and Agonists of LDCAM

An "antagonist," as defined herein, is a molecule that partially or completely blocks the binding of two cognates thereby inhibiting the downstream biological effects of the cognates' interaction. For example, an antagonist may block the binding of a ligand to its receptor, which in turn reduces and/or prevents intracellular signalling via activating that receptor, which in turn reduces or prevents the downstream biological effects of activating that receptor, such as but not limited to, cell activation, proliferation, differentiation, cytokine release, up-regulation of genes, cell-surface expression of proteins, and the like. Of course, an antagonist may block the interaction of other forms of cognates, such as adhesion molecules.

Therefore, a "LDCAM antagonist" is a molecule that antagonizes one or more of the LDCAM biological activities. A LDCAM antagonists includes, but is not limited to: LDCAM-specific antibodies, LDCAM-specific peptibodies or soluble polypeptides that bind LDCAM (such as LDCAM, CRTAM, B7L-4, and B7L-1 polypeptides) that partially or completely block binding of LDCAM to one or more LDCAM binding partners (such as, but not limited to, LDCAM, CRTAM, B7L-4, and/or B7L-1). A LDCAM antagonist that blocks the binding between LDCAM and CRTAM does not activate CRTAM, such as by binding to CRTAM and crosslinking the CRTAM receptor. Further examples include: CRTAM-specific antibodies, CRTAM-specific peptibodies or soluble polypeptides of CRTAM that bind LDCAM and partially or completely block binding between LDCAM and CRTAM; B7L-1-specific antibodies, B7L-1-specific peptibodies or soluble polypeptides of B7L-1 that bind LDCAM and partially or completely block binding between LDCAM and B7L-1 or other binding partners of LDCAM, such as CRTAM; B7L-4-specific antibodies, B7L-4-specific peptibodies or soluble polypeptides of B7L-4 that bind LDCAM and partially or completely block binding between LDCAM and B7L-4 or other binding partners of LDCAM, such as CRTAM. Antagonists presented herein comprise isolated, soluble polypeptides, antibodies, fusion proteins and peptibodies directed against one or more of the following: LDCAM, B7L-1, B7L-4 or CRTAM. Antagonists presented herein further comprise small molecules, such as peptidomimetics and mimotopes, and the like, that antagonize the interaction between LDCAM, B7L-1, B7L-4, or CRTAM. Additional antagonists comprise antisense oligonucleotides that specifically target and hybridize to the mRNA of LDCAM, B7L-1, B7L-4, or CRTAM thereby preventing gene translation of their respective proteins. Further embodiments comprise gene silencing by RNA-interference molecules tailored to silence expression of LDCAM, B7L-1, B7L-4, or CRTAM. More specific definitions and examples of particular antagonists are provided in the sections below.

An "agonist," as defined herein, is a molecule that activates the downstream biological effects of the cognates' interaction. For example, an agonist may mimic the binding of a ligand to its receptor, which causes intracellular signalling via activating that receptor, which in turn effectuates the downstream biological effects of activating that receptor, such as but not limited to, cell activation, proliferation, differentiation, cytokine release, up-regulation of genes, cell-surface expression of proteins, and the like. Alternatively, the agonist may bind at a site that is adjacent to either of the cognate's respective binding sites and induce a conformational change in that cell protein, thereby enhancing its biological activity. For example, an agonist may bind to LDCAM, but not block the binding between LDCAM/LDCAM or LDCAM/CRTAM or LDCAM/B7L-1 and cause a conformational change in LDCAM such that the binding between LDCAM/LDCAM or LDCAM/CRTAM or LDCAM/B7L-1 is enhanced, such as by increased affinity or avidity between the binding pairs.

Therefore, a "LDCAM agonist" is a molecule that agonizes one or more of the LDCAM biological activities. A LDCAM agonists includes, but is not limited to: LDCAM-specific antibodies, LDCAM-specific peptibodies or soluble polypeptides that bind LDCAM that effectuate the downstream biological effects of LDCAM binding to its one or more LDCAM binding partners (such as, but not limited to, LDCAM, CRTAM, B7L-4, and/or B7L-1). Further examples include: CRTAM-specific antibodies, CRTAM-specific antibodies that are capable of crosslinking CRTAM on the surface of cells and activate the receptor; CRTAM-specific peptibodies or soluble polypeptides that bind CRTAM (such as LDCAM) that effectuate the downstream biological effects of CRTAM binding to one or more CRTAM binding partners, such as LDCAM. Alternative embodiments of LDCAM agonists include soluble LDCAM fusion proteins, such as but not limited to the extracellular domain of LDCAM linked to an Fc domain (as described below). Further embodiments include those LDCAM agonists that have the capacity to bind to CRTAM and crosslink the CRTAM receptor on the surface of cells and activate the receptor. Such LDCAM agonists include CRTAM specific antibodies and peptibodies and LDCAM-Fc fusion proteins capable of crosslinking and activating the CRTAM receptor. Further embodiments include multimeric LDCAM polypeptides that bind CRTAM and have the capacity to crosslink and activate CRTAM receptors on the surface of cells. Agonists presented herein comprise isolated, soluble polypeptides, antibodies, fusion proteins and peptibodies directed against one or more of the following: LDCAM, B7L-1 or CRTAM. Agonists presented herein further comprise small molecules, such as peptidomimetics and mimotopes, and the like, that agonize the interaction between LDCAM, B7L-1 or CRTAM. Additional agonists comprise antisense oligonucleotides that specifically target and hybridize to the mRNA of LDCAM, B7L-1 or CRTAM thereby preventing gene translation of their respective proteins. Further embodiments comprise gene silencing by RNA-interference molecules tailored to silence expression of LDCAM, B7L-1 or CRTAM. More specific definitions and examples of particular agonists are provided in the sections below.

As such, a LDCAM antagonist or agonist may be used to antagonize or agonize one or more of the following: LDCAM-to-LDCAM binding (such as by homotypic aggregation); LDCAM binding to CRTAM; LDCAM binding to B7L-1; T-cell activity, such as activation and proliferation; T-cell responses to activation stimuli; T-cell responses to CD3 stimulation/acitivation; T-cell responses to mitogen stimulation/acitivation; NK-T-cell activity; NK cell activity; B-cell activity; cytokine expression by immune cells, such as, but not limited to, IL-2, INF-gamma and other pro-inflammatory cytokines; activity between antigen presenting cells and T-cells; activity between dendritic cells and T-cells; activity between BDCA3+ dendritic cells and T-cells; activity between antigen presenting cells and NK-T-cells; activity between dendritic cells and NK-T-cells; activity between BDCA3+ dendritic cells and NK-T-cells; activity between antigen presenting cells and NK cells; activity between dendritic cells and NK cells; activity between BDCA3+ dendritic cells and NK cells; activity between neurons and T-cells; activity between neurons and NK-T-cells; and activity between neurons and NK cells.

2.1 Antibodies to LDCAM, CRTAM or B7L-1

Antibodies that are immunoreactive with LDCAM, CRTAM or B7L-1 may be used as a LDCAM antagonist or agonist. One particular embodiment comprises a LDCAM-specific scfv antibody, referred to as 1F12. The 1F12 scfv sequence is presented in FIG. 6. An alternative embodiment is the 1F12 scfv-Fc fusion protein (sometimes referred to as the 1F12 maxibody). The 1F12 scfv antibody was used to isolate a new subset of dendritic cells in humans that are the human counterpart of mouse CD8α+ dendritic cells. This dendritic cell subset is referred to as BDCA3+ dendritic cells.

Dendritic cells (DC) constitute a heterogeneous population of professional antigen-presenting cells that control T cell priming and tolerance. In mice, spleen DC can be subdivided into at least three distinct functional subsets according to the surface expression of CD4 and CD8α antigens. Unlike other mouse DC subsets, CD8α+ DC exhibit the unique ability to engulf apoptotic bodies and thus are believed to play a critical role in antigen cross-presentation. We describe herein a cell panning/phage display approach to target and identify novel surface antigens specifically expressed on human blood DC subsets. We show that an antibody (1F12) targets a surface antigen present on both BDCA3+ human blood DC and HLA-DR+, CD13+ cells in the T-cell area of spleen and lymph nodes. These cells may be geographically distinct representations of the same human DC subpopulation. In the mouse, 1F12 specifically labels a rare subset of blood leukocytes as well as splenic CD8α+ DC. 1F12 immunoprecipitates a surface protein of 100 Kda, which was recognized by mass spectrometry as LDCAM. Both mouse and human LDCAM+ DC express CD11c but not CD11b. They also uniquely express a common panel of ten specific genes, thus reinforcing the notion that they represent equivalent populations of cells. Finally, unlike any other human DC subset, LDCAM+ human DC can efficiently internalize apoptotic bodies. We conclude that LDCAM expression define a unique population of DC in mouse and human that share phenotypic, histologic, and functional characteristics.

The isolated and phenotyped DC subset (see FIG. 1) have significant immunological roles, including being the major source of IL-12 production in response to pathogens in vivo; being responsible for in vivo cross-presentation of antigens to CD8+ T-cells; capable of phagocytosing apoptotic bodies in vivo; and being responsible for the induction of tolerance in steady state conditions (such as in the absence of inflammation).

Antibodies to the BDCA3+ DC may be used in a variety of research, clinical and therapeutic settings, including, but not limited to, modulating the function of BDCA3+ DC to influence the outcome of immune responses, such as targeting the BDCA3+ DCs with the 1F12 antibody linked to an antigen and thereby specifically delivering the antigen to the BDCA3+ DC population. This process may confer immune tolerance to the subject to that antigen. Alternatively, in the presence of inflammatory signals, the targeted antigen would heighten antigen-specific immune responses to that antigen. The 1F12 antibody and other anti-LDCAM antibodies may be used for prognostic purposes, such as comparative or relative BDCA3+ DC quantification in normal and pathological tissues. The 1F12 antibody and other anti-LDCAM antibodies may be used to purify or isolate BDCA3+ DC from diverse bodily fluids, organs and tissues. The BDCA3+ DC may then be used in various cell-based immunotherapies by manipulating the cells ex vivo and reinfusing the manipulated cells back into the subject. The 1F12 antibody and other anti-LDCAM antibodies may be used to deplete BDCA3+ DC in vivo or interfere with their immunological function, such as, but not limited to T-cell priming, DC homing, cross-presentation of antigen to T-cells, especially CD8+ T-cells. Because cross-presentation of antigens and cross-tolerance to antigens are cellular mechanisms central to many autoimmune diseases, transplantation and cancer, the 1F12 antibody and other anti-LDCAM antibodies may be used to treat these disorders by modulating the immune responses through the BDCA3+ DC.

In addition, the 1F12 antibody and other anti-LDCAM antibodies may be used in ex vivo cell therapy. The BDCA3+ DC may be isolated with the 1F12 antibody and other anti-LDCAM antibodies and manipulated ex vivo and reintroduced into the patient to treat disease. For exemplary purposes only, one could break immune tolerance to cancer by exposing the isolated BDCA3+ DC to cancer antigens (such as but not limted to those presented in the Table 2 below) and infusing the BDCA3+ DC/processed cancer antigen back into the patient. The cancer antigen may be derived from the patient and may be in the form of cancer cells. It has been shown that BDCA3+ DC are capable of phagocytosing apoptotic cells and will likely present such exogenous antigen to CD8+ T-cells for generating cancer-specific CTL effectors.

TABLE 2

| Antigen Category | Some Specific Examples of Representative Antigens |
|---|---|
| Viruses | Rotavirus; foot and mouth disease; influenza, including influenza A and B; parainfluenza; Herpes species (Herpes simplex, Epstein-Barr virus, chicken pox, pseudorabies, cytomegalovirus); rabies; polio; hepatitis A; hepatitis B; hepatitis C; hepatitis E; measles; distemper; Venezuelan equine encephalomyelitis; feline leukemia virus; reovirus; respiratory syncytial virus; bovine respiratory syncytial virus; Lassa fever virus; polyoma tumor virus; parvovirus; canine parvovirus; papilloma virus; tick-borne encephalitis; rinderpest; human rhinovirus species; enterovirus species; Mengo virus; paramyxovirus; avian infectious bronchitis virus; HTLV 1; HIV-1; HIV-2; LCMV (lymphocytic choriomeningitis virus); adenovirus; togavirus (rubella, yellow fever, dengue fever); corona virus |
| Bacteria | *Bordetella pertussis*; *Brucella abortis*; *Escherichia coli*; *Salmonella* species including *Salmonella typhi*; streptococci; *Vibrio* species (*V. cholera*, *V. parahaemolyticus*); *Shigella* species; *Pseudomonas* species; *Brucella* species; *Mycobacteria* species (tuberculosis, avium, BCG, leprosy); pneumococci; staphlylococci; *Enterobacter* species; *Rochalimaia henselae*; *Pasterurella* species (*P. haemolytica*, *P. multocida*); *Chlamydia* species (*C. trachomatis*, *C. psittaci*, *Lymphogranuloma venereum*); Syphilis (*Treponema pallidum*); *Haemophilus* species; *Mycoplasma* species; Lyme disease (*Borrelia burgdorferi*); Legionnaires' disease; Botulism (*Colstridium botulinum*); *Corynebacterium diphtheriae*; *Yersinia entercolitica* |

TABLE 2-continued

| Antigen Category | Some Specific Examples of Representative Antigens |
|---|---|
| Ricketsial Infections | Rocky mountain spotted fever; thyphus; *Ehrlichia* species |
| Parasites and Protozoa | Malaria (*Plasmodium falciparum, P. vivax, P. malariae*); schistosomes; trypanosomes; *Leishmania* species; filarial nematodes; trichomoniasis; sarcosporidiasis; *Taenia* species (*T. saginata, T. solium*); *Toxoplasma gondii*; trichinelosis (*Trichinella spiralis*); coccidiosis (*Eimeria* species) |
| Fungi | *Cryptococcus neoformans*; *Candida albicans*; *Apergillus fumigatus*; coccidioidomycosis |
| Recombinant Proteins | Herpes simplex; Epstein-Barr virus; hepatitis B; pseudorabies; flavivirus (dengue, yellow fever); *Neisseria gonorrhoeae*; malaria: circumsporozoite protein, merozoite protein; trypanosome surface antigen protein; pertussis; alphaviruses; adenovirus |
| Proteins | Diphtheria toxoid; tetanus toxoid; meningococcal outer membrane protein (OMP); streptococcal M protein; hepatitis B; influenza hemagglutinin; cancer antigen; tumor antigens; toxins; exotoxins; neurotoxins; cytokines and cytokine receptors; monokines and monokine receptors |
| Synthetic Peptides | Malaria; influenza; foot and mouth disease virus; hepatitis B; hepatitis C |
| Polysaccharides | Pneumococcal polysaccharide; Haemophilus influenza polyribosyl-ribitolphosphate (PRP); *Neisseria meningitides*; *Pseudomonas aeruginosa*; *Klebsiella pneumoniae* |
| Oligosaccharide | Pneumococcal |
| Allergens | Plant pollens; animal dander; dust mites, *Blatella* species antigens (Bla g 1, 2, or 5), *Periplaneta* species antigens (Per a 1) |
| Human Cancer Ags | Class I restricted antigens recognized by CD8+ lymphocytes: Melanoma-Melanocyte Differentiation Antigens (MART-1/Melan A; gp100/pmel-17; Tyrosinase; Tyronsinase Related Protein-1; Tyronsinase Related Protein-2; Melanocyte-Stimulating Hormone Receptor); Cancer-Testes Antigens (MAGE-1; MAGE-2; MAGE-3; MAGE-12, BAGE; CAGE, NYESO-1); Mutated Antigens (β-catenin; MUM-1; CDK-4; Caspase-8; KIA 0205; HLA-A2-R1701); and Non-Mutated Shared Antigens Overexpressed on Cancers (α-Fetoprotein; Telomerase Catalytic Protein; G-250; MUC-1; Carcinoembryonic antigen; p53; Her-2/neu). Class II restricted antigens recognized by CD4+ lymphocytes: Epitopes from Non-Mutated Proteins (gp100; MAGE-1; MAGE-3; Tyrosinase; NY-ESO-1) and Epitopes from Mutated Proteins (Triosephosphate isomerase; CDC-27; LDLR-FUT) |
| Infectious agents as cancer Ags | Bacteria: *Helicobacter pylori* (gastric cancer and lymphoma) Viruses: Human Papliloma Virus (cervical and anal cancers); Hepatitis B and C Virus (liver cancer); HIV (Kaposi's sarcoma, non-Hodgkin's lymphoma); Human-Herpesvirus Type B (Kaposi's sarcoma); Epstein-Barr Virus (lymphomas); Human T-Cell Lymphotropic Viirus (adult T-cell leukemia) Parasite: Schistosomes (bladder cancer); Liver Flukes (cholangiocarcinoma) |

In alternative embodiments, the 1F12 antibody and other anti-LDCAM antibodies may be used to deliver drugs or toxins to the BDCA3+ DC, which would in turn influence downstream immune responses.

Alternative embodiments include antibodies that are agonists or antagonists that bind to LDCAM polypeptides, LDCAM polypeptide fragments, LDCAM polypeptide variants, etc. and modulate the biological activities described in the definition of biological activity. Alternative embodiments of LDCAM antagonists and agonists include antibodies that bind to CRTAM polypeptides, CRTAM polypeptide fragments, CRTAM polypeptide variants, etc. and modulate the biological activities described in the definition of biological activity. Such antibodies specifically bind to the polypeptides via the antigen-binding sites of the antibody (as opposed to non-specific binding). For example, LDCAM-specific antibodies are those that will specifically recognize and bind LDCAM polypeptides, homologues, and variants, but not with other molecules. In one preferred embodiment, the antibodies are specific for the polypeptides of the present invention and do not cross-react with other polypeptides. In this manner, the LDCAM polypeptides, fragments, variants, fusion polypeptides, etc., as set forth above can be employed as "immunogens" in producing antibodies immunoreactive therewith.

More specifically, the polypeptides, fragment, variants, fusion polypeptides, etc. contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (Janeway and Travers, *Immuno Biology* 3:9 (Garland Publishing Inc., 2nd ed. 1996)). Because folded polypeptides have complex surfaces, the number of epitopes available is quite numerous; however, due to the conformation of the polypeptide and steric hindrances, the number of antibodies that actually bind to the epitopes is less than the number of available epitopes (Janeway and Travers, *Immuno Biology* 2:14 (Garland Publishing Inc., 2nd ed. 1996)). Epitopes can be identified by any of the methods known in the art. Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies can be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kozbor et al., 1984, *J. Immunol.* 133:3001-3005; Cole et al., 1983, *Proc. Natl. Acad. Sci. USA* 80:2026-2030); and the EBV-hybridoma technique (Cole et al., 1985, Monoclonal Antibodies And Cancer Therapy, Alan R. Liss, Inc., pp. 77-96). Hybridoma cell lines that produce monoclonal antibodies specific for the polypeptides of the invention are also contemplated herein. Such hybridomas can be produced and identified by conventional techniques. The hybridoma producing the mAb of this invention can be cultivated in vitro or in vivo. Production of high titers of mAbs in vivo makes this the presently preferred method of production. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. For the production of antibodies, various host animals can be immunized by injection with one or more of the following: a LDCAM polypeptide, a fragment of a LDCAM polypeptide, a functional equivalent of a LDCAM polypeptide, a vaiant form of LDCAM or a mutant form of a LDCAM polypeptide; a CRTAM polypeptide, a fragment of a CRTAM polypeptide, a functional equivalent of a CRTAM polypeptide, or a mutant form of a CRTAM polypeptide. Such host animals can include but are not limited to rabbits, guinea pigs, mice, and rats. Various adjuvants can be used to increase the immunologic response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies can be of any immunoglobulin class including IgG, IgM, IgE, IgA, IgD and any subclass thereof.

In addition, techniques developed for the production of LDCAM or CRTAM "chimeric antibodies" (Takeda et al., 1985, *Nature*, 314: 452-454; Morrison et al., 1984, *Proc Natl Acad Sci USA* 81: 6851-6855; Boulianne et al., 1984, *Nature* 312: 643-646; Neuberger et al., 1985, Nature 314: 268-270) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the present invention also include humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen-binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, Can, 1993). Useful techniques for humanizing antibodies are also discussed in U.S. Pat. No. 6,054,297. Procedures to generate antibodies transgenically can be found in GB 2,272,440, U.S. Pat. Nos. 5,569,825 and 5,545,806, and related patents. Preferably, for use in humans, the antibodies are human or humanized; techniques for creating such human or humanized antibodies are also well known and are commercially available from, for example, Medarex Inc. (Princeton, N.J.) and Abgenix Inc. (Fremont, Calif.).

In another embodiment, fully human antibodies for use in humans are produced by screening a library of human antibody variable domains using either phage display methods (Vaughan et al., 1998, *Nat Biotechnol.* 16(6): 535-539; and U.S. Pat. No. 5,969,108), ribosome display methods (Schaffitzel et al., 1999, *J Immunol Methods* 231(1-2): 119-135), or mRNA display methods (Wilson et al., 2001, *Proc Natl Acad Sci USA* 98(7): 3750-3755). An example of an anti-LDCAM scfv antibody produced by phage display methods is described in Example 18.

Antigen-binding antibody fragments that recognize specific epitopes can be generated by known techniques. For example, such fragments include but are not limited to: the F(ab')2 fragments which can be produced by pepsin digestion of the antibody molecule and the Fab fragments which can be generated by reducing the disulfide bridges of the (ab')2 fragments. Alternatively, Fab expression libraries can be constructed (Huse et al., 1989, Science, 246:1275-1281) to allow rapid and easy identification of monoclonal Fab fragments with the desired specificity. Techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334:544-546) can also be adapted to produce single chain antibodies against LDCAM gene products. Single chain antibodies are formed by linking the heavy and light chain fragments of the Fv region via an amino acid bridge, resulting in a single chain polypeptide. Such single chain antibodies can also be useful intracellularly (i.e., as intrabodies), for example as described by Marasco et al. (*J. Immunol. Methods* 231:223-238, 1999) for genetic therapy in HIV infection. In addition, antibodies to the LDCAM polypeptide can, in turn, be utilized to generate anti-idiotype antibodies that "mimic" the LDCAM polypeptide and that may bind to the LDCAM polypeptide's binding partners using techniques well known to those skilled in the art. (See, e.g., Greenspan & Bona, 1993, *FASEB J* 7(5):437-444; and Nissinoff, 1991, *J. Immunol.* 147(8):2429-2438).

Antibodies that are immunoreactive with the polypeptides of the invention include bispecific antibodies (i.e., antibodies that are immunoreactive with the polypeptides of the invention via a first antigen binding domain, and also immunoreactive with a different polypeptide via a second antigen binding domain). A variety of bispecific antibodies have been prepared, and found useful both in vitro and in vivo (see, for example, U.S. Pat. No. 5,807,706; and Cao and Suresh, 1998, Bioconjugate Chem 9: 635-644). Numerous methods of preparing bispecific antibodies are known in the art, including the use of hybrid-hybridomas such as quadromas, which are formed by fusing two differed hybridomas, and triomas, which are formed by fusing a hybridoma with a lymphocyte (Milstein and Cuello, 1983, *Nature* 305: 537-540; U.S. Pat. No. 4,474,893; and U.S. Pat. No. 6,106, 833). U.S. Pat. No. 6,060,285 discloses a process for the production of bispecific antibodies in which at least the genes for the light chain and the variable portion of the heavy chain of an antibody having a first specificity are transfected into a hybridoma cell secreting an antibody having a second specificity. Chemical coupling of antibody fragments has also been used to prepare antigen-binding molecules having specificity for two different antigens (Brennan et al., 1985, *Science* 229: 81-83; Glennie et al., *J. Immunol.*, 1987, 139:2367-2375; and U.S. Pat. No. 6,010, 902). Bispecific antibodies can also be produced via recombinant means, for example, by using. the leucine zipper moieties from the Fos and Jun proteins (which preferentially form heterodimers) as described by Kostelny et al. (*J. Immnol.* 148:1547-4553; 1992). U.S. Pat. No. 5,582,996 discloses the use of complementary interactive domains (such as leucine zipper moieties or other lock and key interactive domain structures) to facilitate heterodimer formation in the production of bispecific antibodies. Tetravalent, bispecific molecules can be prepared by fusion of DNA encoding the heavy chain of an F(ab')2 fragment of an antibody with either DNA encoding the heavy chain of a second F(ab')2 molecule (in which the CH1 domain is replaced by a CH3 domain), or with DNA encoding a single chain FV fragment of an antibody, as described in U.S. Pat. No. 5,959,083. Expression of the resultant fusion genes in mammalian cells, together with the genes for the corresponding light chains, yields tetravalent bispecific molecules having specificity for selected antigens. Bispecific antibodies can also be produced as described in U.S. Pat. No. 5,807,706. Generally, the method involves introducing a protuberance (constructed by replacing small amino acid side chains with larger side chains) at the interface of a first polypeptide and a corresponding cavity (prepared by replacing large amino acid side chains with smaller ones) in the interface of a second polypeptide. Moreover, single-chain variable fragments (sFvs) have been prepared by covalently joining two variable domains; the resulting antibody fragments can form dimers or trimers, depending on the length of a flexible linker between the two variable domains (Kortt et al., 1997, *Protein Engineering* 10:423-433).

Screening procedures by which such antibodies can be identified are well known, and can involve immunoaffinity chromatography, for example. Antibodies can be screened for agonistic (i.e., ligand-mimicking) properties. Such antibodies, upon binding to cell surface portions of LDCAM polypeptides, induce biological effects (e.g., transduction of biological signals) similar to the biological effects induced when the LDCAM binding partner binds to LDCAM polypeptides. Agonistic antibodies can be used to induce LDCAM-mediated cell stimulatory pathways or intercellular communication. Bispecific antibodies can be identified by screening with two separate assays, or with an assay wherein the bispecific antibody serves as a bridge between the first antigen and the second antigen (the latter is coupled to a detectable moiety). Bispecific antibodies that bind LDCAM polypeptides of the invention via a first antigen binding domain will be useful in diagnostic applications and in treating autoimmunity, inflammation and cancer, as described in greater detail below.

Those antibodies that can block binding of the LDCAM polypeptides of the invention to binding partners for LDCAM, such as, but not limited to LDCAM (homotypic aggregation), B7L-1 and CRTAM, can be used to inhibit LDCAM, B7L-1 and/or CRTAM-mediated cell binding, intercellular communication or cell stimulation that results from such binding. Such blocking antibodies can be identified using any suitable assay procedure, such as by testing antibodies for the ability to inhibit binding of LDCAM to certain binding partners, such as, but not limited to LDCAM (homotypic aggregation), B7L-1 and CRTAM. Antibodies can be assayed for the ability to inhibit LDCAM binding partner-mediated cell stimulatory pathways, such as those described in the Examples. Such an antibody can be employed in an in vitro procedure, or administered in vivo to inhibit a biological activity mediated by the entity that generated the antibody. Disorders caused or exacerbated (directly or indirectly) by the interaction of LDCAM with cell surface binding partner, such as, but not limited to LDCAM (homotypic aggregation), B7L-1 and CRTAM, thus can be treated. A therapeutic method involves in vivo administration of a blocking antibody to a mammal in an amount effective in inhibiting LDCAM binding partner-mediated biological activity. Monoclonal antibodies are generally preferred for use in such therapeutic methods. In one embodiment, an antigen-binding antibody fragment is employed, such as the scfv-Fc antibody described in the Examples. Compositions comprising an antibody that is directed against LDCAM, and a physiologically acceptable diluent, excipient, or carrier, are provided herein. Suitable components of such compositions are as described below for compositions containing LDCAM polypeptides.

Also provided herein are conjugates comprising a detectable (e.g., diagnostic) or therapeutic agent, attached to the LDCAM-specific antibody. Examples of such agents are presented above. The conjugates find use in vitro or in vivo procedures. The antibodies of the invention can also be used in assays to detect the presence of the polypeptides or fragments of the invention, either in vitro or in vivo. The antibodies also can be employed in purifying polypeptides or fragments of the invention by immunoaffinity chromatography.

Examples of assays that may be used to screen agonistic or antagonistic antibodies are described below.

2.2 Peptibodies to LDCAM, CRTAM, B7L-4, or B7L-1

A LDCAM antagonist or agonist may be in the form of a peptibody directed against LDCAM, CRTAM, B7L-4 or B7L-1. Additional LDCAM agonist embodiments include CRTAM-directed peptibodies that have the capacity to bind and activate CRTAM on the surface of cells, such as but not limited to crosslinking CRTAM on the surface of cells. Peptibodies are known in the art. For exemplary purposes peptibodies are defined and described in greater detail in WO 99/25044 and WO 00/24782, which are incorporated herein by reference in their entirety. The peptide used to create the peptibody may be from the amino acid sequence of LDCAM B7L-1 or CRTAM. The anti-human LDCAM scfv sequences provided in SEQ ID Nos: 12 and 13 may be incorporated into a peptibody 2.3 Rational Design of Compounds that Interact with LDCAM and CRTAM Polypeptides The goal of rational drug design is to produce structural analogs of biologically active polypeptides of interest or of small molecules with which they interact, e.g., inhibitors, agonists, antagonists, etc. Any of these examples can be used to fashion drugs which are more active or stable forms of the polypeptide or which enhance or interfere with the function of a polypeptide in vivo (Hodgson J (1991) Biotechnology 9:19-21). In one approach, the three-dimensional structure of a polypeptide of interest, or of a polypeptide-inhibitor complex, is determined by x-ray crystallography, by nuclear magnetic resonance, or by computer homology modeling or, most typically, by a combination of these approaches. Both the shape and charges of the polypeptide must be ascertained to elucidate the structure and to determine active site(s) of the molecule. Less often, useful information regarding the structure of a polypeptide may be gained by modeling based on the structure of homologous polypeptides. In both cases, relevant structural information is used to design analogous molecules for LDCAM and CRTAM polypeptides, to identify efficient inhibitors, or to identify small molecules that bind LDCAM or CRTAM polypeptides. Useful examples of rational drug design include molecules which have improved activity or stability as shown by Braxton S and Wells J A (1992 Biochemistry 31:7796-7801) or which act as inhibitors, agonists, or antagonists of native peptides as shown by Athauda S B et al (1993 J Biochem 113:742-746). The use of LDCAM and CRTAM polypeptide structural information in molecular modeling software systems to assist in inhibitor design and in studying inhibitor-LDCAM or CRTAM polypeptide interaction is also encompassed by the invention. A particular method of the invention comprises analyzing the three dimensional structure of LDCAM and CRTAM polypeptides for likely binding sites of substrates, synthesizing a new molecule that incorporates a predictive reactive site, and assaying the new molecule as described further herein.

It is also possible to isolate a target-specific antibody, selected by functional assay, as described further herein, and then to solve its crystal structure. This approach, in principle, yields a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original antigen. The anti-id could then be used to identify and isolate peptides from banks of chemically or biologically produced peptides. The isolated peptides would then act as the pharmacore.

2.4 Nucleic Acid-Based LDCAM Antagonists and Agonists

In alternative embodiments, nucleic acid-based immuno therapy can be designed to reduce the level of endogenous LDCAM, CRTAM and/or B7L-1 gene expression, e.g., using antisense or ribozyme approaches to inhibit or prevent translation of LDCAM, CRTAM and/or B7L-1 mRNA transcripts; triple helix approaches to inhibit transcription of the LDCAM, CRTAM and/or B7L-1 gene; or targeted homologous recombination to inactivate or "knock out" the LDCAM, CRTAM and/or B7L-1 gene or its endogenous promoter.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a mRNA having an LDCAM, CRTAM and/or B7L-1 polynucleotide sequence. Absolute complementarity, although preferred, is not required. A sequence "complementary" to a portion of RNA, as referred herein, means a sequence having sufficient complementarity to be able to hybridize with the RNA, thereby forming a stable duplex. Oligonucleotides that are complementary to the 5' end of the message, e.g., the 5' untranslated sequence up to and including the AUG initiation codon, should work most efficiently at inhibiting translation. However, oligonucleotides complementary to either the 5'- or 3'-non-translated, non-coding regions of the LDCAM, CRTAM and/or B7L-1 gene transcript could be used in an antisense approach to inhibit translation of endogenous LDCAM, CRTAM and/or B7L-1. Oligonucleotides complementary to the 5' untranslated region of the mRNA should include the complement of the AUG start codon. Antisense nucleic acids should be at least six nucleotides in length, and are preferably oligonucleotides ranging from 6 to about 50 nucleotides in length. The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988), or hybridization-triggered cleavage agents or intercalating agents (see, e.g., Zon, 1988, Pharm. Res. 5:539-549).

The antisense molecules are delivered to cells, which express a transcript having an LDCAM, CRTAM and/or B7L-1 polynucleotide sequence in vivo by, for example, injecting directly into the tissue or cell derivation site, or by use of modified antisense molecules, designed to target the desired cells (e.g., antisense linked to peptides or antibodies that specifically bind receptors or antigens expressed on the target cell surface) can be administered systemically. Another approach utilizes a recombinant DNA construct in which the antisense oligonucleotide is placed under the control of a strong pol III or pol II promoter. The use of such a construct to transfect target cells in the subject will result in the transcription of sufficient amounts of single stranded RNAs that will form complementary base pairs with the endogenous LDCAM, CRTAM and/or B7L-1 transcripts and thereby prevent translation of the IL-17 mRNA. For example, a vector can be introduced in vivo such that it is taken up by a cell and directs the transcription of an antisense RNA. Such a vector can remain episomal or become chromosomally integrated, so long as it can be transcribed to produce the desired antisense RNA. Vectors can be plasmid, viral, or others known in the art, used for replication and expression in mammalian cells.

Ribozyme molecules designed to catalytically cleave mRNA transcripts having an LDCAM, CRTAM and/or B7L-1 polynucleotide sequence prevent translation of LDCAM, CRTAM and/or B7L-1 mRNA (see, e.g., PCT International Publication WO90/11364, published Oct. 4, 1990; U.S. Pat. No. 5,824,519). Ribozymes are RNA molecules possessing the ability to specifically cleave other single-stranded RNA in a manner analogous to DNA restriction endonucleases. A major advantage of this approach is that, because they are sequence-specific, only mRNAs with particular sequences are inactivated. There are two basic types of ribozymes namely, tetrahymena-type (Hasselhoff, Nature, 334:585-591, 1988) and "hammerhead"-type. Tetrahymena-type ribozymes recognize sequences, which are four bases in length, while "hammerhead"-type ribozymes recognize base sequences 11-18 bases in length. The longer the recognition sequence, the greater the likelihood that the sequence will occur exclusively in the target mRNA species.

Consequently, hammerhead-type ribozymes are preferable to tetrahymena-type ribozymes.

As in the antisense approach, the ribozymes can be composed of modified oligonucleotides (e.g. for improved stability, targeting, and the like). A typical method of delivery involves using a DNA construct "encoding" the ribozyme under the control of a strong constitutive pol III or pol II promoter, so that transfected cells will produce sufficient quantities of the ribozyme to destroy endogenous LDCAM, CRTAM and/or B7L-1 message and inhibit translation. Because ribozymes, unlike antisense molecules, are catalytic, a lower intracellular concentration is required for efficiency.

Alternatively, endogenous LDCAM, CRTAM and/or B7L-1 expression can be reduced by targeting deoxyribonucleotide sequences complementary to the regulatory region of the target gene (i.e., the target gene promoter and/or enhancers) to form triple helical structures that prevent transcription of the target LDCAM, CRTAM and/or B7L-1 gene (see generally, Helene, 1991, Anticancer Drug Des., 6(6), 569-584; Helene, et al., 1992, Ann. N.Y. Acad. Sci., 660, 27-36; and Maher, 1992, Bioassays 14(12), 807-815).

Antisense RNA and DNA, ribozyme, and triple helix molecules of the invention may be prepared by any method known in the art for the synthesis of DNA and RNA molecules and include techniques for chemically synthesizing oligodeoxyribonucleotides and oligoribonucleotides such as, for example, solid phase phosphoramidite chemical synthesis, e.g. by use of an automated DNA synthesizer (such as are commercially available from Biosearch, Applied Biosystems, and the like). As examples, phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448-7451). Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In alternative embodiments LDCAM, CRTAM and/or B7L-1 expression may be blocked by post-translational gene silencing, such as by double-stranded RNA-induced gene silencing, also known as RNA interference (RNAi). RNA sequences of LDCAM, CRTAM and/or B7L-1 may be modified to provide double-stranded sequences or short hairpin RNAs for therapeutic use.

3. LDCAM

LDCAM antagonists and agonists comprise all suitable forms of LDCAM described herein that exhibit biological activity. LDCAM is a cell surface protein having limited homology to adhesion molecules that are expressed on a variety of cells including, but not limited to, dendritic cells and in particular lymphoid-derived dendritic cells. The nucleotide sequence encoding human LDCAM, isolated as described in Example 3, is presented in SEQ ID NO:1, and the amino acid sequence encoded thereby is presented in SEQ ID NO:2. The encoded human LDCAM amino acid sequence described in SEQ ID NO:2 has a predicted extracellular domain of 374 amino acids including a leader sequence of 38 amino acids 1-38 (thus, the extracellular domain lacking a leader sequence spans amino acids 39-374); a transmembrane domain of 21 amino acids (375-395) and a cytoplasmic domain of 47 amino acids (396-442). A soluble form of LDCAM is naturally formed by alternative splicing. Further examples of LDCAM are provided in the following section, which includes, but is not limited to, variants, biologically active fragments, fragments, biologically active fragments and fragments of variants, fusion proteins, peptibodies, mimetopes, derivatives and the like.

B7L-1, which has sequence similarity to B7-1, is a binding partner for LDCAM, as described in U.S. patent application Ser. No. 09/778,187, filed Feb. 6, 2001, which is incorporated herein by reference in its entirety. Because B7L-1 is a LDCAM binding protein and because B7L-1 and LDCAM display homology within their intracellular domain that includes potential binding sites for band 4.1 and PDZ family members, and are found on many of the same cell types, their cell bound forms may deliver similar signals when engaged. Thus, they are termed co-receptors or counterstructures. The nucleotide sequence encoding long and short extracellular forms of human B7L-1 are presented in SEQ ID NO:7 and SEQ ID NO:9, respectively. The amino acid sequences encoded by the nucleotide sequences of SEQ ID NO:7 and SEQ ID NO:9 are disclosed in SEQ ID NO:8 and SEQ ID NO:10, respectively.

To identify cell lines to which B7L-1 binds and to subsequently isolate a protein to which B7L-1 binds, a B7L-1/Fc fusion protein was prepared as described in Example 1 and binding studies, described in Example 2, were carried out. Example 3 describes screening a cDNA library prepared from WI-26, a cell line to which B7L-1 binds, and identifying a full length LDCAM human clone. The nucleotide sequence encoding human LDCAM, isolated as described in Example 3, is presented in SEQ ID NO:1, and the amino acid sequence encoded thereby is presented in SEQ ID NO:2. The encoded human LDCAM amino acid sequence described in SEQ ID NO:2 has a predicted extracellular domain of 374 amino acids including a leader sequence of 38 amino acids 1-38; a transmembrane domain of 21 amino acids (375-395) and a cytoplasmic domain of 47 amino acids (396-442).

Examples 5 and 6 describe making and using a human LDCAM/Fc in binding studies to identify cell lines to which the human LDCAM binds. Among cell lines positively identified were S49.1 cells and lymphoid dendritic cells from spleens and lymph nodes of Flt3-L treated mice. Example 7 describes screening pools of an expression library to identify murine LDCAM clones. The isolated murine LDCAM DNA sequence is disclosed in SEQ ID NO:3. The amino acid sequence encoded by the nucleotide sequence of SEQ ID NO:3 is disclosed in SEQ ID NO:4. The encoded murine LDCAM amino acid sequence (SEQ ID NO:4) has a predicted extracellular domain of 356 amino acids (residues 1-356); a transmembrane domain of 21 amino acids (357-377); and a cytoplasmic domain that includes amino acid residues 378-423. SEQ ID NO:3 and SEQ ID NO:4 describes the full length mature murine LDCAM sequences. As compared to the human LDCAM sequence, the signal sequence is not completely described.

The purified mammalian LDCAM molecules described herein are Type I transmembrane proteins having limited overall homology to B7-1 and other cell adhesion molecules. LDCAM has high homology to the cytoplasmic region of B7L-1. As described below in Example 6, LDCAM proteins demonstrate widespread expression. In particular, human LDCAM mRNA is found in breast, retina, fetal liver spleen, fetal heart, lung, muscle, placenta, thyroid, and lung carcinoma. Cell lines that have LDCAM message include Wi-26. Mouse LDCAM mRNA is found on whole embryo, testes, triple negative cells murine splenic and lymph node CD8+, S49.1 and dendritic cells.

The discovery of the DNA sequences disclosed in SEQ ID NOs:1 and 3 enables construction of expression vectors comprising DNAs encoding human and mouse LDCAM proteins; host cells transfected or transformed with the expression vectors; biologically active LDCAM as homogeneous proteins; and antibodies immunoreactive with LDCAM.

Like B7L-1, LDCAM has limited homology to poliovirus receptor, delta opoid binding protein and adhesion molecules. Moreover, as described in Example 13, LDCAM blocks T cell proliferation caused by ConA and PHA, suggesting the LDAM is useful in modulating T cell mediated immune response. LDCAM does not inhibit TCR mAb induced T cell proliferation suggesting that the inhibitory effects of LDCAM on mitogen-induced T cell proliferation is due to inhibition of cytokine secretion, e.g. IL-2, or due to the regulation of downstream responses of the T cell following activation and increases in the expression of the LDCAM binding partner. While not limited to such, particular uses of the LDCAM molecules are described infra.

As used herein, the term LDCAM encompasses polypeptides having the amino acid sequence 1-442 of SEQ ID NO:2 and the amino acid sequence 1-423 of SEQ ID NO:4. In addition, LDCAM encompasses polypeptides that have a high degree of similarity or a high degree of identity with the amino acid sequence of SEQ ID NO:2, the amino acid sequence of SEQ ID NO:4, and which polypeptides are biologically active.

The term "LDCAM" refers to a genus of polypeptides described herein that, at least in part, bind and complex with themselves, bind B7L-1 and CRTAM and alter T cell activation signals in response to antigen and mitogens.

The term "murine LDCAM" refers to biologically active gene products of the DNA of SEQ ID NO:3 and the term "human LDCAM" refers to biologically active gene products of the DNA of SEQ ID NO:1. Further encompassed by the term "LDCAM" are soluble or truncated proteins that comprise primarily the B7L-1 co-binding portion of the protein, retain biological activity and are capable of being secreted. Specific examples of such soluble proteins are those comprising the sequence of amino acids 1-374 of SEQ ID NO:2 and those comprising the sequence of amino acids 1-356 of SEQ ID NO:4. Alternatively, such soluble proteins can exclude a leader sequence and thus encompass amino acids 39-374 of SEQ ID NO:2.

Example 9 describes the construction of a novel LDCAM/Fc fusion protein that may be utilized in LDCAM binding studies, screening assays for LDCAM antagonists and/or agonists, and studies directed to examining functional characteristics of the molecule. Other antibody Fc regions may be substituted for the human IgG1 Fc region described in the Example. Other suitable Fc regions are those that can bind with high affinity to protein A or protein G, or those that include fragments of the human or murine IgG1 Fc region, e.g., fragments comprising at least the hinge region so that interchain disulfide bonds will form. The LDCAM fusion protein offers the advantage of being easily purified. In addition, disulfide bonds form between the Fc regions of two separate fusion protein chains, creating dimers.

As described supra, an aspect of the invention is soluble LDCAM polypeptides. Soluble LDCAM polypeptides comprise all or part of the extracellular domain of a native LDCAM but lack the signal that would cause retention of the polypeptide on a cell membrane. Soluble LDCAM polypeptides advantageously comprise the native (or a heterologous) signal peptide when initially synthesized to promote secretion, but the signal peptide is cleaved upon secretion of LDCAM from the cell. Soluble LDCAM polypeptides encompassed by the invention retain the ability to bind B7L-1, or the ability to bind to themselves. Alternatively soluble LDCAM polypeptides of the present invention retain the ability to alter T cell responses. Soluble LDCAM may include part of the signal or part of the cytoplasmic domain or other sequences, provided that the soluble LDCAM protein can be secreted.

Soluble LDCAM may be identified (and distinguished from its non-soluble membrane-bound counterparts) by separating intact cells which express the desired protein from the culture medium, e.g., by centrifugation, and assaying the medium or supernatant for the presence of the desired protein. The presence of LDCAM in the medium indicates that the protein was secreted from the cells and thus is a soluble form of the desired protein.

Soluble forms of LDCAM possess many advantages over the native bound LDCAM protein. Purification of the proteins from recombinant host cells is feasible, since the soluble proteins are secreted from the cells. Further, soluble proteins are generally more suitable for intravenous administration.

Examples of soluble LDCAM polypeptides include those comprising a substantial portion of the extracellular domain of a native LDCAM protein. For example, a soluble human LDCAM protein comprises amino acids 38-374 or 1-374 of SEQ ID NO:2 and a soluble murine LDCAM includes amino acids 1-356 of SEQ ID NO:4. In addition, truncated soluble LDCAM proteins comprising less than the entire extracellular domain are included in the invention. When initially expressed within a host cell, soluble LDCAM may include one of the heterologous signal peptides described below that is functional within the host cells employed. Alternatively, the protein may comprise the native signal peptide. In one embodiment of the invention, soluble LDCAM can be expressed as a fusion protein comprising (from N— to C-terminus) the yeast a-factor signal peptide, a FLAG® peptide described below and in U.S. Pat. No. 5,011,912, and soluble LDCAM consisting of amino acids 39-374 of SEQ ID NO:2 or 21-356 of SEQ ID NO:4. This recombinant fusion protein is expressed in and secreted from yeast cells. The FLAG® peptide facilitates purification of the protein, and subsequently may be cleaved from the soluble LDCAM using bovine mucosal enterokinase. Isolated DNA sequences encoding soluble LDCAM proteins are encompassed by the invention.

Truncated LDCAM, including soluble polypeptides, may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the receptor-binding domain.

As stated above, the invention provides isolated or homogeneous LDCAM polypeptides, both recombinant and non-recombinant. Additionally within the scope of the present invention are variants and derivatives of native LDCAM proteins that retain the desired biological activity. Such activity includes the ability of LDCAM to bind to itself, or the ability to bind to B7L-1, or the ability to alter T cell signaling. LDCAM variants and derivatives may be obtained by mutations of nucleotide sequences coding for native LDCAM polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol*. 154:367, 1987); and U.S. Pat. Nos. 4,518,584 and 4,737,462 all of which are incorporated by reference.

LDCAM variants may be used as antagonists or agonists or be used to develop LDCAM antagonists or agonists, such as antibodies, peptibodies and mimetoopes. A "LDCAM variant" as referred to herein, means a polypeptide substantially homologous to native LDCAM, but which has an amino acid sequence different from that of native LDCAM (human, murine or other mammalian species) because of one or more deletions, insertions or substitutions. Substantially homologous means a variant amino acid sequence that is at least 75%, at least 80%, at least 85%, at least 90%, at least 95%, at least 96%, at least 97%, at least 98% or at least 99% identical to the native amino acid sequences, as disclosed above. The percent identity of two amino acid or two nucleic acid sequences can be determined by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al., 1984, *Nucl. Acids Res*. 12: 387). The preferred default parameters for the 'GAP' program includes: (1) The GCG implementation of a unary comparison matrix (containing a value of 1 for identities and 0 for non-identities) for nucleotides, and the weighted amino acid comparison matrix of Gribskov and Burgess, *Nucl. Acids Res*. 14:6745, 1986, as described by Schwartz and Dayhoff, eds., Atlas of Polypeptide Sequence and Structure, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.0.9, available for use via the National Library of Medicine website www.ncbi.nlm.nih-.gov/gorf/wblast2.cgi, or the UW-BLAST 2.0 algorithm. Standard default parameter settings for UW-BLAST 2.0 are described at the following Internet site: sapiens.wustl.edu/blast/blast/#Features. In addition, the BLAST algorithm uses the BLOSUM62 amino acid scoring matix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, *Methods Enzymol*. 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

Such variants include polypeptides that are substantially homologous to native LDCAM sequences, but which have an amino acid sequence different from that of a native IL-17 receptor because of one or more deletions, insertions or substitutions. Particular embodiments include, but are not limited to, LDCAM polypeptides that comprise at least one conservative amino acid substitution. Alternative embodiments comprise LDCAM polypeptides comprising from one to ten deletions, insertions or substitutions of amino acid residues, when compared to a native sequences. The LDCAM-encoding polynucleotides of the present invention include variants that differ from a LDCAM polynucleotide sequence because of one or more deletions, insertions or substitutions, but that encode a biologically active polypeptide. Included as variants of LDCAM polypeptides are those variants that are naturally occurring, such as allelic forms and alternatively spliced forms, as well as variants that have been constructed by modifying the amino acid sequence of a LDCAM polypeptide or the nucleotide sequence of a nucleic acid encoding a LDCAM polypeptide.

As mentioned above, LDCAM variants may comprise a sequence having at least one conservatively substituted amino acid, meaning that a given amino acid residue is replaced by a residue having similar physiochemical characteristics. Alternative embodiments comprise LDCAM variants that comprise between 1-10, 1-20 or 1-30 conservatively substituted sequences. Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of LDCAM. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring variants are also encompassed by the invention. Examples of such variants are proteins that result from alternate mRNA splicing events or from proteolytic cleavage of the native protein, wherein the native biological property is retained.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, *Acta Physiol. Scand. Suppl.* 643:55-67; Sasaki et al., 1998, *Adv. Biophys.* 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-peptide molecules (see preceding formulae) described herein. Exemplary amino acid substitutions are set forth in Table 1.

TABLE 1

Amino Acid Substitutions

| Original Residues | Exemplary Substitutions | Preferred Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

As noted above, naturally occurring residues may be divided into classes based on common sidechain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. (Kyte, et al., *J. Mol. Biol.*, 157:105-131 (1982)). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in the foregoing sequences using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a peptide to similar peptides. With such a comparison, one can identify residues and portions of the molecules that are conserved among similar polypeptides. It will be appreciated that changes in areas of a peptide that are not conserved relative to such similar peptides would be less likely to adversely affect the biological activity and/or structure of the peptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides.

One skilled in the art can also analyze the three-dimensional structure and amino acid sequence in relation to that structure in similar polypeptides. In view of that information, one skilled in the art may predict the alignment of amino acid residues of a peptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See, Moult J., *Curr. Op. in Biotech.*, 7(4): 422-427 (1996), Chou et al., *Biochemistry*, 13(2): 222-245 (1974); Chou et al., *Biochemistry*, 113(2): 211-222 (1974); Chou et al., *Adv. Enzymol. Relat. Areas Mol. Biol.*, 47: 45-148 (1978); Chou et al., *Ann. Rev. Biochem.*, 47: 251-276 and Chou et al., *Biophys. J.*, 26: 367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm, et al., *Nucl. Acid. Res.*, 27(1): 244-247 (1999). It has been suggested (Brenner et al., *Curr. Op. Struct. Biol.*, 7(3): 369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., *Curr. Opin. Struct. Biol.*, 7(3): 377-87 (1997); Sippl, et al., *Structure*, 4(1): 15-9 (1996)), "profile analysis" (Bowie, et al., *Science*, 253: 164-170 (1991); Gribskov, et al., *Meth. Enzym.*, 183: 146-159 (1990); Gribskov, et al., *Proc. Nat. Acad. Sci.*, 84(13): 4355-8 (1987)), and "evolutionary linkage" (See Holm, supra, and Brenner, supra).

Further modifications in the LDCAM polypeptide or LDCAM polynucleotide sequences can be made by those skilled in the art using known techniques. Modifications of interest in the polypeptide sequences can include the alteration, substitution, replacement, insertion or deletion of a selected amino acid. For example, one or more of the cysteine residues can be deleted or replaced with another amino acid to alter the conformation of the molecule, an alteration which may involve preventing formation of incorrect intramolecular disulfide bridges upon folding or renaturation. Techniques for such alteration, substitution, replacement, insertion or deletion are well known to those skilled in the art (see, e.g., U.S. Pat. No. 4,518,584). As another example, N-glycosylation sites in the LDCAM extracellular domain can be modified to preclude glycosylation, allowing expression of a reduced carbohydrate analog in mammalian and yeast expression systems. N-glycosylation sites in the LDCAM extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X—Y, wherein X is any amino acid except Pro and Y is Ser or Thr. The human LDCAM polypeptide of SEQ ID NO:2 includes six such triplets, at amino acids 67-69, 101-103, 113-115, 165-167, 304-306, and 308-310. Similarly, the murine LDCAM polypeptide of SEQ ID NO:4 includes sic such triplets at 49-51, 83-85, 95-97, 147-149, 286-288 and 290-292. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

Additional variants within the scope of the invention include LDCAM polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Preferably, such alteration, substitution, replacement, insertion or deletion does not diminish the biological activity of LDCAM. One example is a variant that binds with essentially the same binding affinity as does the native form. Binding affinity can be measured by conventional procedures, e.g., as described in U.S. Pat. No. 5,512,457 and as set forth herein. Furthermore, LDCAM molecules may be modified by the addition of one or more water-soluble polymers, such as, but not limited to, polyethylene glycol to increase bio-availability and/or pharmacokinetic half-life.

Various means for attaching chemical moieties useful for increase bio-availability and/or pharmacokinetic half-life are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

An alternative polymer vehicle is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kD to about 50 kD, most preferably from about 5 kD to about 10 kD. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water-soluble polymer which may be used for protein modification. Dextrans are polysaccharide polymers comprised of individual subunits of glucose predominantly linked by $\alpha$1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference in its entirety. Dextran of about 1 kD to about 20 kD is preferred when dextran is used as a vehicle in accordance with the present invention.

Additional LDCAM derivatives include covalent or aggregative conjugates of the polypeptides with other polypeptides or polypeptides, such as by synthesis in recombinant culture as N-terminal or C-terminal fusions. Examples of fusion polypeptides are discussed below in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., Bio/Technology 6:1204, 1988. One such peptide is the FLAG® octapeptide (SEQ ID NO:31), which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Additional embodiments of LDCAM that may be used in the methods described herein include oligomers or fusion polypeptides that contain LDCAM polypeptide, one or more fragments of LDCAM, or any of the derivative or variant forms of LDCAM as disclosed herein, as well as in the U.S. patents listed above. In particular embodiments, the oligomers comprise soluble LDCAM polypeptides. Oligomers can be in the form of covalently linked or non-covalently-linked multimers, including dimers, trimers, or higher oligomers. In alternative embodiments, LDCAM oligomers comprise multiple LDCAM polypeptides joined via covalent or non-covalent interactions between peptide moieties fused to the polypeptides, such peptides having the property of promoting oligomerization. Leucine zippers and certain polypeptides derived from antibodies are among the peptides that can promote oligomerization of the polypeptides attached thereto, as described in more detail below.

LDCAM may be modified to create LDCAM derivatives by forming covalent or aggregative conjugates with other chemical moieties, such as glycosyl groups, lipids, phosphate, acetyl groups and the like. Covalent derivatives of LDCAM may be prepared by linking the chemical moieties to functional groups on LDCAM amino acid side chains or at the N-terminus or C-terminus of a LDCAM polypeptide or the extracellular domain thereof. Other derivatives of LDCAM within the scope of this invention include covalent or aggregative conjugates of LDCAM or its fragments with other proteins or polypeptides, such as by synthesis in recombinant culture as N-terminal or C-terminal fusions. For example, the conjugate may comprise a signal or leader polypeptide sequence (e.g. the $\alpha$-factor leader of Saccharomyces) at the N-terminus of a LDCAM polypeptide. The signal or leader peptide co-translationally or post-translationally directs transfer of the conjugate from its site of synthesis to a site inside or outside of the cell membrane or cell wall.

LDCAM polypeptide fusions can comprise peptides added to facilitate purification and identification of LDCAM. Such peptides include, for example, poly-His or the antigenic identification peptides described in U.S. Pat. No. 5,011,912 and in Hopp et al., Bio/Technology 6:1204, 1988.

Equivalent DNA constructs that encode various additions or substitutions of amino acid residues or sequences, or deletions of terminal or internal residues or sequences not needed for biological activity or binding are encompassed by the invention. For example, N-glycosylation sites in the LDCAM extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The human LDCAM polypeptide of SEQ ID NO:2 includes six such triplets, at amino acids 67-69, 101-103, 113-115, 165-167, 304-306, and 308-310. Similarly, the murine LDCAM polypeptide of SEQ ID NO:4 includes sic such triplets at 49-51, 83-85, 95-97, 147-149, 286-288 and 290-292. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Nucleic acid sequences within the scope of the invention include isolated DNA and RNA sequences that hybridize to the LDCAM nucleotide sequences disclosed herein under conditions of moderate or severe stringency, and that encode biologically active LDCAM. Conditions of moderate stringency, as defined by Sambrook et al. *Molecular Cloning: A Laboratory Manual*, 2 ed. Vol. 1, pp. 101-104, Cold Spring Harbor Laboratory Press, (1989), include use of a prewashing solution of 5×SSC, 0.5% SDS, 1.0 mM EDTA (pH 8.0) and hybridization conditions of about 55° C., 5×SSC, overnight. Conditions of severe stringency include higher temperatures of hybridization and washing. The skilled artisan will recognize that the temperature and wash solution salt concentration may be adjusted as necessary according to factors such as the length of the nucleic acid molecule.

Due to the known degeneracy of the genetic code wherein more than one codon can encode the same amino acid, a DNA sequence may vary from that shown in SEQ ID NO:1 and 3 and still encode a LDCAM protein having the amino acid sequence of SEQ ID NO:2 and SEQ ID NO:4, respectively. Such variant DNA sequences may result from silent mutations (e.g., occurring during PCR amplification), or may be the product of deliberate mutagenesis of a native sequence.

The invention provides equivalent isolated DNA sequences encoding biologically active LDCAM, selected from: (a) cDNA comprising the nucleotide sequence presented in SEQ ID NO:1 and SEQ ID NO:3; (b) DNA capable of hybridization to a DNA of (a) under moderately stringent conditions and that encodes biologically active LDCAM; and (c) DNA that is degenerate as a result of the genetic code to a DNA defined in (a), or (b) and that encodes biologically active LDCAM. LDCAM proteins encoded by such DNA equivalent sequences are encompassed by the invention.

DNAs that are equivalent to the DNA sequence of SEQ ID NO:1 and SEQ ID NO:3 will hybridize under moderately and severely stringent conditions to DNA sequences that encode polypeptides comprising SEQ ID NO:2, and SEQ ID NO:4. Examples of LDCAM proteins encoded by such DNA, include, but are not limited to, LDCAM fragments (including soluble fragments) and LDCAM proteins comprising inactivated N-glycosylation site(s), inactivated KEX2 protease processing site(s), or conservative amino acid substitution(s), as described above. LDCAM proteins encoded by DNA derived from other mammalian species, wherein the DNA will hybridize to the cDNA of SEQ ID NO:1 or SEQ ID NO:3 are also encompassed by the present invention.

Variants possessing the ability to bind B7L-1 may be identified by any suitable assay. Biological activity of LDCAM may be determined, for example, by competition for binding to the binding domain of B7L-1 (i.e. competitive binding assays).

One type of a competitive binding assay for a LDCAM polypeptide uses a radiolabeled, soluble LDCAM and intact cells expressing B7L-1-expressing. Instead of intact cells, one could substitute soluble B7L-1/Fc fusion proteins such as a B7L-1/Fc bound to a solid phase through the interaction of a Protein A, Protein G or an antibody to the B7L-1 or Fc portions of the molecule, with the Fc region of the fusion protein. Another type of competitive binding assay utilizes a radiolabeled soluble LDCAM receptor and intact cells expressing LDCAM.

Competitive binding assays can be performed following conventional methodology. For example, radiolabeled LDCAM can be used to compete with a putative LDCAM homologue to assay for binding activity against B7L-1 or a surface-bound LDCAM receptor. Qualitative results can be obtained by competitive autoradiographic plate binding assays, or Scatchard plots may be utilized to generate quantitative results.

Alternatively, LDCAM-binding proteins, such as B7L-1 and anti-LDCAM antibodies, can be bound to a solid phase such as a column chromatography matrix or a similar substrate suitable for identifying, separating or purifying cells that express LDCAM on their surface. Binding of a LDCAM-binding protein to a solid phase contacting surface can be accomplished by any means, for example, by constructing a B7L-1/Fc fusion protein and binding such to the solid phase through the interaction of Protein A or Protein G. Various other means for fixing proteins to a solid phase are well known in the art and are suitable for use in the present invention. For example, magnetic microspheres can be coated with B7L-1 and held in the incubation vessel through a magnetic field. Suspensions of cell mixtures containing LDCAM-expressing cells are contacted with the solid phase that has B7L-1 polypeptides thereon. Cells having LDCAM on their surface bind to the fixed B7L-1 and unbound cells then are washed away. This affinity-binding method is useful for purifying, screening or separating such LDCAM-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of B7L-1:LDCAM interactions, the enzyme preferably frees the resulting cell suspension from the LDCAM material. The purified cell population, especially if obtained from fetal tissue, then may be used to repopulate mature (adult) tissues.

Alternatively, mixtures of cells suspected of containing LDCAM$^+$ cells first can be incubated with biotinylated B7L-1. Incubation periods are typically at least one hour in duration to ensure sufficient binding to LDCAM. The resulting mixture then is passed through a column packed with avidin-coated beads, whereby the high affinity of biotin for avidin provides the binding of the cell to the beads. Use of avidin-coated beads is known in the art. See Berenson, et al. *J. Cell. Biochem.*, 10D:239 (1986). Wash of unbound material and the release of the bound cells is performed using conventional methods.

As described above, B7L-1 can be used to separate cells expressing LDCAM. In an alternative method, LDCAM or an extracellular domain or a fragment thereof can be conjugated to a detectable moiety such as $^{125}$I to detect B7L-1-expressing cells. Radiolabeling with $^{125}$I can be performed by any of several standard methodologies that yield a functional $^{125}$I-LDCAM molecule labeled to high specific activity. Or an iodinated or biotinylated antibody against the B7L-1 region or the Fc region of the molecule could be used. Another detectable moiety such as an enzyme that can catalyze a colorimetric or fluorometric reaction, biotin or avidin may be used. Cells to be tested for B7L-1-expression can be contacted with labeled LDCAM. After incubation, unbound labeled LDCAM is removed and binding is measured using the detectable moiety.

The binding characteristics of LDCAM (including variants) may also be determined using the conjugated, soluble LDCAM/Fc (for example, $^{125}$I-LDCAM/Fc) in competition assays similar to those described above. In this case, however, intact cells expressing LDCAM/Fc bound to a solid substrate, are used to measure the extent to which a sample containing a putative LDCAM variant competes for binding with a conjugated soluble binding partner for LDCAM.

Other means of assaying for LDCAM include the use of anti-LDCAM antibodies, cell lines that proliferate in response to LDCAM, or recombinant cell lines that proliferate in the presence of LDCAM.

The LDCAM proteins disclosed herein also may be employed to measure the biological activity of B7L-1 or other LDCAM binding proteins in terms of their binding affinity for LDCAM. As one example, LDCAM may be used in determining whether biological activity is retained after modification of B7L-1 (e.g., chemical modification, truncation, mutation, etc.). The biological activity of a B7L-1 protein thus can be ascertained before it is used in a research study, or possibly in the clinic, for example.

LDCAM proteins find use as reagents that may be employed by those conducting "quality assurance" studies, e.g., to monitor shelf life and stability of B7L-1 or other LDCAM binding protein under different conditions. To illustrate, LDCAM may be employed in a binding affinity study to measure the biological activity of an B7L-1 protein that has been stored at different temperatures, or produced in different cell types. The binding affinity of the modified B7L-1 protein for LDCAM is compared to that of an unmodified B7L-1 protein to detect any adverse impact of the modifications on biological activity of B7L-1. Likewise, the biological activity of a LDCAM protein can be assessed using B7L-1.

LDCAM polypeptides also find use as carriers for delivering agents attached thereto to T cells or other cells bearing B7L-1, LDCAM and/or CRTAM. LDCAM proteins can be used to deliver diagnostic or therapeutic agents to these cells in in vitro or in vivo procedures. As described in Example 5, LDCAM is found on the PAE81BM cell line, which is an EBV transformed cell line. Thus, one example of such carrier use is to expose this cell line to a therapeutic agent/LDCAM conjugate to assess whether the agent exhibits cytotoxicity toward any EBV cancers. Additionally, since LDCAM is expressed on dendritic cells and CD40L activated B cells that are important in antigen presentation, LDCAM is a useful carrier for targeting, identifying, and purifying these cells. Also, LDCAM/diagnostic agent conjugates may be employed to detect the presence of dendritic cells and B cells in vitro or in vivo. Example 6 demonstrates that human LDCAM mRNA, transcripts are found in human breast, retinal, fetal liver, spleen, fetal heart, lung, placenta, thyroid and lung carcinoma. Similar studies for expression of mouse LDCAM mRNA showed that mouse LDCAM mRNA is found in whole embryo, testes, lymphoid derived dendritic cells and triple negative cells. Since, LDCAM binds to itself, LDCAM can be used to study its functional role in these tissues.

Alternatively, LDCAM may be targeted to other LDCAM binding partners, such as, but not limited to B7L-1, CRTAM and LDCAM, on additional target cells. Examples include, but are not limited to, activated CD4+ T-cells, CD8+ T-cells, NK-T cells and/or NK cells via CRTAM; antigen presenting cells, such as dendritic cells, which includes BDCA3+ human dendritic cells and CD8α$^+$ via LDCAM.

A number of different therapeutic agents or other functional markers attached to LDCAM, as well as anti-LDCAM or CRTAM antibodies, peptibodies and the like, may be used in conjugates in an assay to detect and compare the cytotoxic effects of the agents on the cells or study the role of LDCAM in tissues and cells. Diagnostic and therapeutic agents that may be attached to a LDCAM polypeptide include, but are not limited to, drugs, toxins, radionuclides, chromophores, enzymes that catalyze a colorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diptheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the LDCAM, as well as anti-LDCAM or CRTAM antibodies, peptibodies and the like, by any suitable conventional procedure. LDCAM, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to LDCAM by using a suitable bifunctional chelating agent, for example.

Conjugates comprising LDCAM, as well as anti-LDCAM or CRTAM antibodies, peptibodies and the like, and a suitable diagnostic or therapeutic agent (preferably covalently linked) are thus prepared. The conjugates are administered or otherwise employed in an amount appropriate for the particular application.

As mentioned above, because LDCAM blocks T cell proliferation caused by ConA and PHA and does not inhibit TCR mAb induced T cell proliferation, the inhibitory effects of LDCAM on mitogen-induced T cell proliferation may be due to the inhibition of cytokine secretion, e.g. IL-2. Accordingly, another use of the LDCAM of the present invention is as a research tool for studying the role that LDCAM plays in the production of IL-2 in T cells. The LDCAM polypeptides of the present invention also may be employed in in vitro assays for detection of B7L-1 or the interactions thereof.

One embodiment of the present invention is directed to a method of treating disorders associated with a malfunctioning immune system. More particularly, since LDCAM is known to block ConA stimulated T cells and PHA stimulated T cells, LDCAM may be useful in treating inflammation and autoimmune disorders mediated by T cell responses. A composition that includes a LDCAM protein, preferably a soluble polypeptide, and a pharmaceutically acceptable diluent or carrier may be administered to a mammal to treat such inflammation or autoimmune disorder. SCID mice that have been injected with soluble LDCAM, in the form of LDCAM/Fc, experience an increase in splenic cellularity. Part of this increase is due to an increase in DX-5$^+$ cells, also known as natural killer cells (NK cells). When injected with LDCAM/Fc and IL-15, a NK cell growth factor, SCID mice demonstrate an increase in NK cells that is additive. This further evidences the ability of LDCAM, LDCAM fragments soluble LDCAM, as well as LDCAM agonists to generate NK cells. In view of this discovery, another embodiment of the present invention includes methods for increasing the number of NK cells in an individual by administering, to that individual, pharmaceutical compositions, of the present invention, containing LDCAM, soluble LDCAM LDCAM fragments, as well as LDCAM agonists. In another embodiment, NK cells may be increased ex vivo by contacting NK cells with LDCAM or soluble forms of LDCAM, as well as LDCAM agonists and allowing the NK cells to expand. Similarly, NK cells can be generated in vivo or ex vivo, as just described, by administering LDCAM or soluble forms of LDCAM, as well as LDCAM agonists in connection with additional cytokines or growth factors. Thus, the present methods for generating NK cells, in vivo or ex vivo can further include the use of an effective amount of a cytokine in sequential or concurrent combination with LDCAM. Such cytokines include, but are not limited to, interleukins ("ILs") IL-15, IL-3 and IL-4, a colony stimulating factor ("CSF") selected from the group consisting of granulocyte macrophage colony stimulating factor ("GM-CSF") or GM-CSF/IL-3 fusions, or other cytokines such as TNF-α, CD40 binding proteins (e.g. CD40-L), 4-1BB antagonists (e.g. antibodies immunoreactive with 4-1BB and 4-1BB-L) or c-kit ligand.

NK cells are large granular lymphocytes that are distinct from T or B lymphocytes in morphology and function. NK cells mediate killing certain tumor cells and virally infected cells in non-MHC restricted manners. Additionally, NK cells are involved in the rejection of donor cells by bone marrow transplant recipients. Since LDCAM increases NK cell numbers, LDCAM, soluble LDCAM, LDCAM fragments, as well as LDCAM agonists are useful in combating virally infected cells and infectious diseases. Similarly, LDCAM, soluble LDCAM, and LDCAM fragments are useful for killing tumor cells. Accordingly, within the scope of the present invention are methods for treating infectious diseases and methods for treating individuals afflicted with tumors. Such therapeutic methods involve administering LDCAM, soluble forms of LDCAM, or LDCAM fragments to an individual in need of increasing their numbers of NK cells in order to kill tumor cells or enhance their ability to combat infectious disease. Similarly, the therapeutic methods of the present invention can be carried out by administering LDCAM, soluble LDCAM, e.g. LDCAM fusion protein, or LDCAM fragments sequentially or concurrently in combination cytokines. Such cytokines include, but are not limited to, interleukins ("ILs") IL-15, IL-3 and IL-4, a colony stimulating factor ("CSF") selected from the group consisting of granulocyte macrophage colony stimulating factor ("GM-CSF") or GM-CSF/IL-3 fusions, or other cytokines such as TNF-α, CD40 binding proteins (e.g. CD40-L), 4-1BB antagonists (e.g. antibodies immunoreactive with 4-1BB and 4-1BB-L) or c-kit ligand. Further within the scope of the present invention are methods for preventing or decreasing the effect of organ and bone marrow transplant rejection by recipients of the transplant. Such methods involve treating recipients with a composition that includes a LDCAM antagonist, thus inhibiting increases in NK cell populations and decreasing the ability of NK cells to reject transplants. Treatment of human endothelial cells (aortic and umbilical cord) with a soluble form of human LDCAM results in calcium fluxes within the cells. Calcium fluxes in endothelial cells are important in modulating vascular permeability, endothelial cell migration and angiogenesis, and adhesion and transmigration of leukocytes. LDCAM polypeptides and LDCAM inhibitors may therefore be used to improve drug delivery across the blood-brain barrier, to augment an immune response against a tumor or pathogen, to lessen an autoimmune or inflammatory syndrome, to lessen leukocyte adhesion and formation of atherosclerotic plaques, to block angiogenesis, and in the treatment of pathogenic vascular leakage. LDCAM polypeptides, as well as LDCAM antagonists and agonists, may exist as oligomers, such as covalently linked or non-covalently-linked dimers or trimers. Oligomers may be linked by disulfide bonds formed between cysteine residues on different LDCAM polypeptides. In one embodiment of the invention, a LDCAM dimer is created by fusing LDCAM to the Fc region of an antibody (e.g., IgG1) in a manner that does not interfere with binding of LDCAM to the T cells, B7L-1 or itself. The Fc polypeptide preferably is fused to the C-terminus of a soluble LDCAM (comprising only the receptor binding). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the LDCAM:Fc fusion protein is inserted into an appropriate expression vector. LDCAM:Fc fusion proteins are allowed to assemble much like antibody molecules, whereupon interchain disulfide bonds form between Fc polypeptides, yielding divalent LDCAM. If fusion proteins are made with both heavy and light chains of an antibody, it is possible to form a LDCAM oligomer with as many as four LDCAM extracellular regions. Alternatively, one can link two soluble LDCAM domains with a peptide linker.

Antagonists and Agonists as Immunoglobulin-based Oligomers. Suitable forms of LDCAM antagonists and agonists include chimeric proteins which include a second polypeptide that may promote the spontaneous formation by the chimeric protein of a dimer, trimer or higher order multimer that is capable of binding their respective cognates and thereby inhibiting or reducing the effects of inflammation and symptoms of cardiovascular disease. Chimeric proteins used as antagonists or agonists may be proteins that contain portions of an antibody molecule and a soluble polypeptide from LDCAM, B7L-1 or CRTAM. Suitable fusion proteins include an LDCAM, B7L-1 or CRTAM polypeptide, e.g. the extracellular domain, or a fragment of the extracellular domain, linked to an immunoglobulin Fc region. Fragments of a Fc region may also be used, as well as Fc muteins that exhibit decreased affinity for Fc receptors. Soluble LDCAM, B7L-1 or CRTAM, as well as fragments thereof, can be fused directly or through linker sequences to the Fc portion of an immunoglobulin.

One embodiment of a LDCAM antagonist and agonist is directed to a dimer comprising two fusion polypeptides created by fusing LDCAM, B7L-1 or CRTAM polypeptide to a Fc polypeptide derived from an antibody. A gene fusion encoding such a fusion polypeptide is inserted into an appropriate expression vector. LDCAM, B7L-1 or CRTAM-Fc fusion polypeptides are expressed in host cells transformed with the recombinant expression vector, and allowed to assemble much like antibody molecules, whereupon interchain disulfide bonds form between the Fc moieties to yield divalent molecules. One suitable Fc polypeptide, described in PCT application WO 93/10151, is a single chain polypeptide extending from the N-terminal hinge region to the native C-terminus of the Fc region of a human IgG1 antibody. For a bivalent form of LDCAM, B7L-1 or CRTAM, such a fusion could be to the Fc portion of an IgG molecule. Other immunoglobulin isotypes can also be used to generate such fusions. For example, a polypeptide-IgM fusion would generate a decavalent form of the polypeptide of the invention.

Preparation of fusion polypeptides comprising certain heterologous polypeptides fused to various portions of antibody-derived polypeptides (including the Fc domain) are known in the art and have been described, e.g., by Ashkenazi et al. (*PNAS* USA 88:10535, 1991); Byrn et al. (Nature 344:677, 1990); and Hollenbaugh and Aruffo ("Construction of Immunoglobulin Fusion Polypeptides", in *Current Protocols in Immunology*, Suppl. 4, pages 10.19.1-10.19.11, 1992). Another useful Fc polypeptide is the Fc mutein described in U.S. Pat. No. 5,457,035 and in Baum et al., (*EMBO J.* 13:3992-4001, 1994). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The above-described fusion polypeptides comprising Fc moieties (and oligomers formed therefrom) offer the advantage of facile purification by affinity chromatography over Polypeptide A or Polypeptide G columns. In other embodiments, the polypeptides of the invention can be substituted for the variable portion of an antibody heavy or light chain. If fusion polypeptides are made with both heavy and light chains of an antibody, it is possible to form an oligomer with as many as four IL-17R extracellular regions.

LDCAM Antagonists and Agonists Peptide-linker Based Oligomers. Alternatively, the oligomer is a fusion polypeptide comprising multiple LDCAM, B7L-1 and/or CRTAM polypeptides, with or without peptide linkers (spacer peptides). Among the suitable peptide linkers are those described in U.S. Pat. Nos. 4,751,180 and 4,935,233. A DNA sequence encoding a desired peptide linker can be inserted between, and in the same reading frame as, the DNA sequences of the invention, using any suitable conventional technique. For example, a chemically synthesized oligonucleotide encoding the linker can be ligated between the sequences. In particular embodiments, a fusion polypeptide comprises from two to four soluble LDCAM, B7L-1 or CRTAM polypeptides, separated by peptide linkers. Suitable peptide linkers, their combination with other polypeptides, and their use are well known by those skilled in the art.

Oligomeric forms of LDCAM antagonists and agonist may include LDCAM, B7L-1 or CRTAM polyeptide, the extracellular domain of LDCAM, B7L-1 and/or CRTAM polypeptide, or LDCAM, B7L-1 and/or CRTAM fragment of the extracellular domain associated with a zipper domain, such as zipper proteins described in U.S. Patent 5,716,805, the disclosure of which is incorporated by reference herein. Other Examples of zipper domains are those found in the yeast transcription factor GCN4 and a heat-stable DNA-binding protein found in rat liver (C/EBP; Landschulz et al., *Science* 243:1681, 1989), the nuclear transforming proteins, fos and jun, which preferentially form a heterodimer (O'Shea et al., *Science* 245:646, 1989; Turner and Tjian, *Science* 243:1689, 1989), and the gene product of the murine proto-oncogene, c-myc (Landschulz et al., *Science* 240: 1759, 1988). The fusogenic proteins of several different viruses, including paramyxovirus, coronavirus, measles virus and many retroviruses, also possess leucine zipper domains (Buckland and Wild, *Nature* 338:547, 1989; Britton, *Nature* 353:394, 1991; Delwart and Mosialos, *AIDS Research and Human Retroviruses* 6:703, 1990). Leucine zipper domains are peptides that promote oligomerization of the polypeptides in which they are found. Leucine zippers were originally identified in several DNA-binding polypeptides and have since been found in a variety of different polypeptides. Among the known leucine zippers are naturally occurring peptides and derivatives thereof that dimerize or trimerize. The zipper domain (also referred to herein as an oligomerizing, or oligomer-forming, domain) comprises a repetitive heptad repeat, often with four or five leucine residues interspersed with other amino acids. Use of leucine zippers and preparation of oligomers using leucine zippers are well known in the art.

The present invention comprises fusion polypeptides with or without spacer amino acid linking groups. For example, two soluble LDCAM, B7L-1 or CRTAM domains can be linked with a linker sequence, such as $(Gly)_4Ser(Gly)_5Ser$ (SEQ ID NO:32), which is described in U.S. Pat. No. 5,073,627. Other linker sequences include, for example, $GlyAlaGlyGlyAlaGlySer(Gly)_5Ser$ (SEQ ID NO:33), $(Gly_4Ser)_2$ (SEQ ID NO:34), $(GlyThrPro)_3$ (SEQ ID NO:35), and $(Gly_4Ser)_3Gly_4SerGly_5Ser$ (SEQ ID NO:36).

Suitable host cells for expression of LDCAM antagonists and agonists, such as LDCAM, B7L-1 or CRTAM polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce LDCAM polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a LDCAM polypeptide may include an N-terminal methionine residue to facilitate expression of the recombinant polypeptide in the prokaryotic host cell. The N-terminal Met may be cleaved from the expressed recombinant LDCAM polypeptide.

LDCAM antagonists and agonists such as LDCAM, B7L-1 or CRTAM polypeptides may be expressed in yeast host cells, preferably from the *Saccharomyces* genus (e.g., *S. cerevisiae*). Other genera of yeast, such as *Pichia, K. lactis* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285-195 (1991); and van den Berg et. al., *Bio/Technology*, 8:135-139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the LDCAM polypeptide. The a-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 µg/ml adenine and 20 µg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian or insect host cell culture systems could also be employed to express recombinant LDCAM polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, and in addition to an initiator methionine, a heterologous signal sequence may be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

LDCAM antagonists and agonists, as an isolated, purified or homogeneous protein according to the invention, may be produced by recombinant expression systems as described above or purified from naturally occurring cells. LDCAM can be purified to substantial homogeneity, as indicated by a single protein band upon analysis by SDS-polyacrylamide gel electrophoresis (SDS-PAGE).

One process for producing LDCAM comprises culturing a host cell transformed with an expression vector comprising a DNA sequence that encodes LDCAM under conditions sufficient to promote expression of LDCAM. LDCAM is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify LDCAM. Some or all of the foregoing purification steps, in various combinations, are well known and can be employed to provide a substantially homogeneous recombinant protein.

It is possible to utilize an affinity column comprising the ligand-binding domain of a LDCAM binding protein to affinity-purify expressed LDCAM polypeptides. LDCAM polypeptides can be removed from an affinity column using conventional techniques, e.g., in a high salt elution buffer and then dialyzed into a lower salt buffer for use or by changing pH or other components depending on the affinity matrix utilized. Alternatively, the affinity column may comprise an antibody that binds LDCAM. Example 10 describes a procedure for employing LDCAM of the invention to generate monoclonal antibodies directed against LDCAM.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express LDCAM as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Useful fragments of the LDCAM nucleic acids include antisense or sense oligonucleotides comprising a single-stranded nucleic acid sequence (either RNA or DNA) capable of binding to target LDCAM mRNA (sense) or LDCAM DNA (antisense) sequences. Antisense or sense oligonucleotides, according to the present invention, comprise a fragment of the coding region of LDCAM cDNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

4. CRTAM

As described above, LDCAM antagonists and agonists comprise CRTAM-specific antibodies, CRTAM-specific peptibodies or soluble polypeptides that bind CRTAM (such as LDCAM) modulate downstream biological effects of CRTAM binding to one or more CRTAM binding partners, such as LDCAM. CRTAM is described in U.S. Pat. No. 5,686,257, which is incorporated by reference in its entirety. The sequence for human CRTAM is provided in SEQ ID NO: 11.

5. Assays of LDCAM Antagonists and Agonists Activities

The purified LDCAM polypeptides of the invention (including polypeptides, fragments, variants, oligomers, and other forms) are useful in a variety of assays.

Embodiments include screening assays to identify test compounds that act as LDCAM agonists or antagonists. A number of formats and permutations thereof are envisioned, including, but not limited to: a method of screening for a LDCAM antagonist or agonist, comprising: (a) combining an isolated LDCAM polypeptide with a test compound; (b) adding an isolated CRTAM polypeptide; and (c) determining the relative binding between the LDCAM polypeptide and the CRTAM polypeptide in the presence and absence of the test compound. An alternative embodiment includes a method of screening for a LDCAM antagonist or agonist, comprising: (a) combining a cell expressing a LDCAM polypeptide with a test compound; (b) adding an isolated CRTAM polypeptide; and (c) determining the relative binding between the cell expressing a LDCAM polypeptide and the CRTAM polypeptide in the presence and absence of the test compound. An alternative embodiment includes a method of screening for a LDCAM antagonist or agonist, comprising: (a) combining a cell expressing a LDCAM polypeptide with a test compound; (b) adding a cell expressing a CRTAM polypeptide; and (c) determining the relative binding between the cell expressing a LDCAM polypeptide and the cell expressing the CRTAM polypeptide in the presence and absence of the test compound. An alternative embodiment includes a method of screening for a LDCAM antagonist or agonist, comprising: (a) combining an isolated LDCAM polypeptide with a test compound; (b) adding a cell expressing a CRTAM polypeptide; and (c) determining the relative binding between the LDCAM polypeptide and the cells expressing a CRTAM polypeptide in the presence and absence of the test compound. An alternative embodiment includes a method of screening for a LDCAM agonist, comprising: (a) combining an isolated CRTAM polypeptide with a test compound; and (b) determining the relative binding between the test compound and the CRTAM polypeptide. An alternative embodiment includes a method of screening for a LDCAM agonist, comprising: (a) combining a cell expressing a CRTAM polypeptide; and (b) determining the relative binding or biological effects between the cell expressing a CRTAM polypeptide and the test compound.

For example, the LDCAM and LDCAM-Like molecules of the present invention can be used to identify binding partners of LDCAM polypeptides, which can also be used to modulate intercellular communication, cell stimulation, or immune cell activity. Alternatively, they can be used to identify non-binding-partner molecules or substances, i.e. LDCAM antagonist or agonists, that modulate intercellular communication, cell stimulatory pathways, or immune cell activity.

LDCAM polypeptides also find use in measuring the biological activity of LDCAM-binding polypeptides in terms of their binding affinity. Examples include, but are not limited to LDCAM, CRTAM, B71-4, B7L-1, as well as anti-LDCAM antibodies and peptibodies. The examples listed above can be employed by those conducting "quality assurance" studies, e.g., to monitor shelf life and stability of polypeptide under different conditions. For example, the LDCAM polypeptides can be employed in a binding affinity study to measure the biological activity of a binding partner polypeptide such as, but not limited to, LDCAM (homotypic aggregation), B7L-1, B71-4, and CRTAM, that has been stored at different temperatures, or produced in different cell types. The polypeptides also can be used to determine whether biological activity is retained after modification of a binding partner polypeptide (e.g., chemical modification, truncation, mutation, etc.). The binding affinity of the modified polypeptide is compared to that of an unmodified binding polypeptide to detect any adverse impact of the modifications on biological activity of the binding polypeptide.

Assays to Identify Binding Partners. LDCAM polypeptides and fragments thereof can be used to identify binding partners. Binding partners for LDCAM include, but are not limited to, LDCAM (homotypic aggregation), B7L-1, B7L-4, and CRTAM. For example, they can be tested for the ability to bind a candidate binding partner in any suitable assay, such as a conventional binding assay. To illustrate, the LDCAM polypeptide can be labeled with a detectable reagent (e.g., a radionuclide, chromophore, enzyme that catalyzes a colorimetric or fluorometric reaction, and the like). The labeled LDCAM polypeptide is contacted with cells expressing the candidate binding partner. The cells then are washed to remove unbound labeled polypeptide, and the presence of cell-bound label is determined by a suitable technique, chosen according to the nature of the label.

The LDCAM polypeptides of the invention each can be used as reagents in methods to screen for or identify binding partners such as, but not limited to, LDCAM (homotypic aggregation), B7L-1, B7L-4, and CRTAM. For example, the LDCAM polypeptides can be attached to a solid support material and may bind to their binding partners in a manner similar to affinity chromatography. In particular embodiments, a polypeptide is attached to a solid support by conventional procedures. As one example, chromatography columns containing functional groups that will react with functional groups on amino acid side chains of polypeptides are available (Pharmacia Biotech, Inc., Piscataway, N.J.). In an alternative, a LDCAM polypeptide/Fc fusion protein (as discussed above) is attached to protein A- or protein G-containing chromatography columns through interaction with the Fc moiety. The LDCAM polypeptides also find use in identifying cells that express a LDCAM binding partner on the cell surface such as, but not limited to, LDCAM (homotypic aggregation), B7L-1, B7L-4, and CRTAM. Purified LDCAM polypeptides, as well as other forms, such as variants, fragments, fusion proteins or derivatives, are bound to a solid phase such as a column chromatography matrix or a similar suitable substrate. For example, magnetic microspheres can be coated with the polypeptides and held in an incubation vessel through a magnetic field. Suspensions of cell mixtures containing potential binding-partner-expressing cells are contacted with the solid phase having the polypeptides thereon. Cells expressing the binding partner on the cell surface bind to the fixed polypeptides, and unbound cells are washed away. Alternatively, LDCAM polypeptides can be conjugated to a detectable moiety, then incubated with cells to be tested for binding partner expression. After incubation, unbound labeled matter is removed and the presence or absence of the detectable moiety on the cells is determined. In a further alternative, mixtures of cells suspected of expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods. In some instances, the above methods for screening for or identifying binding partners may also be used or modified to isolate or purify such binding partner molecules or cells expressing them. Examples of binding partners discovered by such methods include, but are not limited to, LDCAM (homotypic aggregation), B7L-1, B7L-4, and CRTAM, as described in the Examples.

One example of a binding assay procedure is as follows. A recombinant expression vector containing the candidate binding partner cDNA is constructed (such as, but not limited to LDCAM (homotypic aggregation), B7L-1, B7L-4, and CRTAM). CV1-EBNA-1 cells in 10 cm$^2$ dishes are transfected with this recombinant expression vector. CV-1/EBNA-1 cells (ATCC CRL 10478) constitutively express EBV nuclear antigen-1 driven from the CMV Immediate-early enhancer/promoter. CV1-EBNA-1 was derived from the African Green Monkey kidney cell line CV-1 (ATCC CCL 70), as described by McMahan et al., (*EMBO J.* 10:2821, 1991). The transfected cells are cultured for 24 hours, and the cells in each dish then are split into a 24-well plate. After culturing an additional 48 hours, the transfected cells (about 4×10$^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion polypeptide of LDCAM made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization. The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any LDCAM polypeptide/Fc polypeptide that has bound to the cells. In all assays, non-specific binding of $^{125}$I-antibody is assayed in the absence of the Fc fusion polypeptide/Fc, as well as in the presence of the Fc fusion polypeptide and a 200-fold molar excess of unlabeled mouse anti-human IgG antibody. Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer. Binding can also be detected using methods that are well suited for high-throughput screening procedures, such as scintillation proximity assays (Udenfriend et al., 1985, *Proc Natl Acad Sci USA* 82: 8672-8676), homogeneous time-resolved fluorescence methods (Park et al., 1999, *Anal Biochem* 269: 94-104), fluorescence resonance energy transfer (FRET) methods (Clegg R M, 1995, *Curr Opin Biotechnol* 6: 103-110), or methods that measure any changes in surface plasmon resonance when a bound polypeptide is exposed to a potential binding partner, using for example a biosensor such as that supplied by Biacore AB (Uppsala, Sweden). Compounds that can be assayed for binding to LDCAM and/or LDCAM-Like polypeptides include but are not limited to small organic molecules, such as those that are commercially available—often as part of large combinatorial chemistry compound 'libraries'—from companies such as Sigma-Aldrich (St. Louis, Mo.), Arqule (Woburn, Mass.), Enzymed (Iowa City, Iowa), Maybridge Chemical Co.(Trevillett, Cornwall, UK), MDS Panlabs (Bothell, Wash.), Pharmacopeia (Princeton, N.J.), and Trega (San Diego, Calif.). Preferred small organic molecules for screening using these assays are usually less than 10K molecular weight and can possess a number of physicochemical and pharmacological properties which enhance cell penetration, resist degradation, and/or prolong their physiological half-lives (Gibbs, J., 1994, Pharmaceutical Research in Molecular Oncology, *Cell* 79(2): 193-198). Compounds including natural products, inorganic chemicals, and biologically active materials such as proteins and toxins can also be assayed using these methods for the ability to bind to LDCAM polypeptides.

Yeast Two-Hybrid or "Interaction Trap" Assays. Where the LDCAM polypeptide binds or potentially binds to another polypeptide (such as, for example, LDCAM (homotypic aggregation), B7L-1 and CRTAM), the nucleic acid encoding the LDCAM polypeptide can also be used in interaction trap assays (such as, for example, that described in Gyuris et al., Cell 75:791-803 (1993)) to identify nucleic acids encoding the other polypeptide with which binding occurs or to identify inhibitors of the binding interaction. Polypeptides involved in these binding interactions can also be used to screen for peptide or small molecule inhibitors or agonists of the binding interaction.

Competitive Binding Assays. Another type of suitable binding assay is a competitive binding assay. To illustrate, biological activity of a variant can be determined by assaying for the variant's ability to compete with the native polypeptide for binding to the candidate binding partner. Competitive binding assays can be performed by conventional methodology. Reagents that can be employed in competitive binding assays include radiolabeled LDCAM and intact cells expressing LDCAM, B7L-1, B7L-4, or CRTAM (endogenous or recombinant) polypeptides on the cell surface. For example, a radiolabeled soluble LDCAM fragment, such as a LDCAM-Fc construct described in the Examples, can be used to compete with a soluble LDCAM variant for binding to binding partners. A soluble binding partner/Fc fusion polypeptide bound to a solid phase through the interaction of Polypeptide A or Polypeptide G (on the solid phase) with the Fc moiety can be used. Chromatography columns that contain Polypeptide A and Polypeptide G include those available from Pharmacia Biotech, Inc., Piscataway, N.J.

Assays to Identify Modulators of Intercellular Communication, Cell Stimulation, or Immune Cell Activity. The influence of LDCAM polypeptides on intercellular communication, cell stimulation, or immune cell activity can be manipulated to control these activities in target cells. For example, the disclosed LDCAM polypeptides, nucleic acids encoding the disclosed LDCAM polypeptides, or agonists or antagonists of such polypeptides, can be administered to a cell or group of cells to induce, enhance, suppress, or arrest cell binding, cellular communication, cell stimulation, or activity in the target cells. Identification of LDCAM polypeptides, agonists or antagonists that can be used in this manner can be carried out via a variety of assays known to those skilled in the art. Included in such assays are those that evaluate the ability of an LDCAM polypeptide to influence cell binding, intercellular communication, cell stimulation or activity. Such an assay would involve, for example, the analysis of immune cell interaction in the presence of a LDCAM polypeptide. In such an assay, one would determine a rate of communication or cell stimulation in the presence of the LDCAM polypeptide and then determine if such communication or cell stimulation is altered in the presence of a candidate agonist or antagonist or another LDCAM polypeptide. Exemplary assays for this aspect of the invention include cytokine secretion assays, T-cell co-stimulation assays, and mixed lymphocyte reactions involving antigen presenting cells and T cells. These assays are well known to those skilled in the art. Further assays are presented in the Examples section below.

In another aspect, the present invention provides a method of detecting the ability of a test compound to affect cell binding, intercellular communication or cell stimulatory activity of a cell. In this aspect, the method comprises: (1) contacting a first group of target cells with a test compound including a LDCAM polypeptide or fragment thereof under conditions appropriate to the particular assay being used; (2) measuring the net rate of cell binding, intercellular communication or cell stimulation among the target cells; and (3) observing the net rate of intercellular communication or cell stimulation among control cells containing the LDCAM polypeptides or fragments thereof, in the absence of a test compound, under otherwise identical conditions as the first group of cells. In this embodiment, the net rate of intercellular communication or cell stimulation in the control cells is compared to that of the cells treated with both the LDCAM molecule as well as a test compound. The comparison will provide a difference in the net rate of cell binding, intercellular communication or cell stimulation such that an effector of cell binding, intercellular communication or cell stimulation can be identified. The test compound can function as an effector by either activating or up-regulating, or by inhibiting or down-regulating cell binding, intercellular communication or cell stimulation, and can be detected through this method.

Cell Proliferation, Cell Death, Cell Differentiation, and Cell Adhesion Assays. A polypeptide of the present invention may exhibit cytokine, cell proliferation (either inducing or inhibiting), or cell differentiation (either inducing or inhibiting) activity, or may induce production of other cytokines in certain cell populations. Many polypeptide factors discovered to date have exhibited such activity in one or more factor-dependent cell proliferation assays, and hence the assays serve as a convenient confirmation of cell stimulatory activity. The activity of a polypeptide of the present invention is evidenced by any one of a number of routine factor-dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK. The activity of a LDCAM polypeptide of the invention may, among other means, be measured by the following methods:

Assays for T-cell or thymocyte proliferation include without limitation those described in: *Current Protocols in Immunology*, Coligan et al. eds, Greene Publishing Associates and Wiley-Interscience (pp. 3.1-3.19: In vitro assays for mouse lymphocyte function; Chapter 7: Immunologic studies in humans); Takai et al., J. Immunol. 137: 3494-3500, 1986; Bertagnolli et al., J. Immunol. 145: 1706-1712, 1990; Bertagnolli et al., Cellular Immunology 133:327-341, 1991; Bertagnolli, et al., J. Immunol. 149:3778-3783, 1992; Bowman et al., J. Immunol. 152: 1756-1761, 1994.

Assays for cytokine production and/or proliferation of spleen cells, lymph node cells or thymocytes include, without limitation, those described in: Kruisbeek and Shevach, 1994, Polyclonal T cell stimulation, in *Current Protocols in Immunology*, Coligan et al. eds. Vol 1 pp. 3.12.1-3.12.14, John Wiley and Sons, Toronto; and Schreiber, 1994, Measurement of mouse and human interferon gamma in *Current Protocols in Immunology*, Coligan et al. eds. Vol 1 pp. 6.8.1-6.8.8, John Wiley and Sons, Toronto.

Assays for proliferation and differentiation of hematopoietic and lymphopoietic cells include, without limitation, those described in: Bottomly et al., 1991, Measurement of human and murine interleukin 2 and interleukin 4, in *Cur-* rent Protocols in Immunology, Coligan et al. eds. Vol 1 pp. 6.3.1-6.3.12, John Wiley and Sons, Toronto; deVries et al., J Exp Med 173: 1205-1211, 1991; Moreau et al., Nature 336:690-692, 1988; Greenberger et al., Proc Natl Acad Sci.USA 80: 2931-2938, 1983; Nordan, 1991, Measurement of mouse and human interleukin 6, in *Current Protocols in Immunology* Coligan et al. eds. Vol 1 pp. 6.6.1-6.6.5, John Wiley and Sons, Toronto; Smith et al., Proc Natl Acad Sci USA 83: 1857-1861, 1986; Bennett et al., 1991, Measurement of human interleukin 11, in *Current Protocols in Immunology* Coligan et al. eds. Vol 1 pp. 6.15.1 John Wiley and Sons, Toronto; Ciarletta et al., 1991, Measurement of mouse and human Interleukin 9, in Current Protocols in Immunology Coligan et al. eds. Vol 1 pp. 6.13.1, John Wiley and Sons, Toronto.

Assays for T-cell clone responses to antigens (which will identify, among others, polypeptides that affect APC-T cell interactions as well as direct T-cell effects by measuring proliferation and cytokine production) include, without limitation, those described in: *Current Protocols in Immunology*, Coligan et al. eds, Greene Publishing Associates and Wiley-Interscience (Chapter 3: In vitro assays for mouse lymphocyte function; Chapter 6: Cytokines and their cellular receptors; Chapter 7: Immunologic studies in humans); Weinberger et al., Proc Natl Acad Sci USA 77: 6091-6095, 1980; Weinberger et al., Eur. J. Immun. 11:405-411, 1981; Takai et al., J. Immunol. 137:3494-3500, 1986; Takai et al., J. Immunol. 140:508-512, 1988

Assays for thymocyte or splenocyte cytotoxicity include, without limitation, those described in: *Current Protocols in Immunology*, Coligan et al. eds, Greene Publishing Associates and Wiley-Interscience (Chapter 3, In Vitro assays for Mouse Lymphocyte Function 3.1-3.19; Chapter 7, Immunologic studies in Humans); Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Takai et al., J. Immunol. 140:508-512, 1988; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Bowmanet al., J. Virology 61:1992-1998; Takai et al., J. Immunol. 140:508-512, 1988; Bertagnolli et al., Cellular Immunology 133:327-341, 1991; Brown et al., J. Immunol. 153:3079-3092, 1994.

Assays for T-cell-dependent immunoglobulin responses and isotype switching (which will identify, among others, polypeptides that modulate T-cell dependent antibody responses and that affect Th1/Th2 profiles) include, without limitation, those described in: Maliszewski, J Immunol 144: 3028-3033, 1990; and Mond and Brunswick, 1994, Assays for B cell function: in vitro antibody production, in *Current Protocols in Immunology* Coligan et al. eds. Vol 1 pp. 3.8.1-3.8.16, John Wiley and Sons, Toronto.

Mixed lymphocyte reaction (MLR) assays (which will identify, among others, polypeptides that generate predominantly Th1 and CTL responses) include, without limitation, those described in: *Current Protocols in Immunology*, Coligan et al. eds, Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137:3494-3500, 1986; Takai et al., J. Immunol. 140:508-512, 1988; Bertagnolli et al., J. Immunol. 149:3778-3783, 1992.

Dendritic cell-dependent assays (which will identify, among others, polypeptides expressed by dendritic cells that activate naive T-cells) include, without limitation, those described in: Guery et al., J. Immunol 134:536-544, 1995; Inaba et al., J Exp Med 173:549-559, 1991; Macatonia et al., J Immunol 154:5071-5079, 1995; Porgador et al., J Exp Med 182:255-260, 1995; Nair et al., J Virology 67:4062-4069, 1993; Huang et al., Science 264:961-965, 1994; Macatonia et al., J Exp Med 169:1255-1264, 1989; Bhardwaj et al., J Clin Invest 94:797-807, 1994; and Inaba et al., J Exp Med 172:631-640,1990.

Assays for lymphocyte survival/apoptosis (which will identify, among others, polypeptides that prevent apoptosis after superantigen induction and polypeptides that regulate lymphocyte homeostasis) include, without limitation, those described in: Darzynkiewicz et al., Cytometry 13:795-808, 1992; Gorczyca et al., Leukemia 7:659-670, 1993; Gorczyca et al., Cancer Research 53:1945-1951, 1993; Itoh et al., Cell 66:233-243, 1991; Zacharchuk, J Immunol 145:4037-4045, 1990; Zamai et al., Cytometry 14:891-897, 1993; Gorczyca et al., International Journal of Oncology 1:639-648, 1992.

Assays for polypeptides that influence early steps of T-cell commitment and development include, without limitation, those described in: Antica et al., Blood 84:111-117, 1994; Fine et al., Cell Immunol 155:111-122, 1994; Galy et al., Blood 85:2770-2778, 1995; Toki et al., Proc Natl Acad Sci. USA 88:7548-7551, 1991

Assays for embryonic stem cell differentiation (which will identify, among others, polypeptides that influence embryonic differentiation hematopoiesis) include, without limitation, those described in: Johansson et al. Cellular Biology 15:141-151, 1995; Keller et al., Molecular and Cellular Biology 13:473-486, 1993; McClanahan et al., Blood 81:2903-2915, 1993.

Assays for stem cell survival and differentiation (which will identify, among others, polypeptides that regulate lympho-hematopoiesis) include, without limitation, those described in: Methylcellulose colony forming assays, Freshney, 1994, In *Culture of Hematopoietic Cells*, Freshney et al. eds. pp. 265-268, Wiley-Liss, Inc., New York, N.Y.; Hirayama et al., Proc. Natl. Acad. Sci. USA 89:5907-5911, 1992; Primitive hematopoietic colony forming cells with high proliferative potential, McNiece and Briddell, 1994, In *Culture of Hematopoietic Cells*, Freshney et al. eds. pp. 23-39, Wiley-Liss, Inc., New York, N.Y.; Neben et al., Experimental Hematology 22:353-359, 1994; Ploemacher, 1994, Cobblestone area forming cell assay, In *Culture of Hematopoietic Cells*, Freshney et al. eds. pp. 1-21, Wiley-Liss, Inc., New York, N.Y.; Spooncer et al., 1994, Long term bone marrow cultures in the presence of stromal cells, In *Culture of Hematopoietic Cells*, Freshney et al. eds. pp. 163-179, Wiley-Liss, Inc., New York, N.Y.; Sutherland, 1994, Long term culture initiating cell assay, In *Culture of Hematopoietic Cells*, Freshney et al. eds. Vol pp. 139-162, Wiley-Liss, Inc., New York, N.Y.

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium). Assays for wound healing activity include, without limitation, those described in: Winter, Epidermal Wound Healing, pps. 71-112 (Maibach and Rovee, eds.), Year Book Medical Publishers, Inc., Chicago, as modified by Eaglstein and Mertz, J. Invest. Dermatol 71:382-84 (1978).

Assays for activin/inhibin activity include, without limitation, those described in: Vale et al., Endocrinology 91:562-572, 1972; Ling et al., Nature 321:779-782, 1986; Vale et al., Nature 321:776-779, 1986; Mason et al., Nature 318:659-663, 1985; Forage et al., Proc. Natl. Acad. Sci. USA 83:3091-3095, 1986.

Assays for cell movement and adhesion include, without limitation, those described in: *Current Protocols in Immunology* Coligan et al. eds, Greene Publishing Associates and Wiley-Interscience (Chapter 6.12, Measurement of alpha and beta chemokines 6.12.1-6.12.28); Taub et al. J. Clin. Invest. 95:1370-1376, 1995; Lind et al. APMIS 103:140-146, 1995; Muller et al Eur. J. Immunol. 25: 1744-1748; Gruber et al. J Immunol. 152:5860-5867, 1994; Johnston et al. J Immunol. 153: 1762-1768, 1994

Assay for hemostatic and thrombolytic activity include, without limitation, those described in: Linet et al., J. Clin. Pharmacol. 26:131-140, 1986; Burdick et al., Thrombosis Res. 45:413-419,1987; Humphrey et al., Fibrinolysis 5:71-79 (1991); Schaub, Prostaglandins 35:467-474, 1988.

Assays for receptor-ligand activity include without limitation those described in: *Current Protocols in Immunology* Coligan et al eds, Greene Publishing Associates and Wiley-Interscience (Chapter 7.28, Measurement of cellular adhesion under static conditions 7.28.1-7.28.22), Takai et al., Proc. Natl. Acad. Sci. USA 84:6864-6868, 1987; Bierer et al., J. Exp. Med. 168:1145-1156, 1988; Rosenstein et al., J. Exp. Med. 169:149-160 1989; Stoltenborg et al., J. Immunol. Methods 175:59-68, 1994; Stitt et al., Cell 80:661-670, 1995.

Assays for cadherin adhesive and invasive suppressor activity include, without limitation, those described in: Hortsch et al. J Biol Chem 270 (32): 18809-18817, 1995; Miyaki et al. Oncogene 11: 2547-2552, 1995; Ozawa et al. Cell 63:1033-1038, 1990.

6. Diagnostic and other uses of LDCAM Antagonists and Agonists

The nucleic acids encoding the LDCAM antagonists and agonists provided by the present invention can be used for numerous diagnostic or other useful purposes. The nucleic acids of the invention can be used to express recombinant polypeptide for analysis, characterization or therapeutic use; as markers for tissues in which the corresponding polypeptide is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel nucleic acids; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for gene therapy. Uses of LDCAM polypeptides and fragmented polypeptides include, but are not limited to, the following: purifying polypeptides and measuring the activity thereof; delivery agents; therapeutic and research reagents; molecular weight and isoelectric focusing markers; controls for peptide fragmentation; identification of unknown polypeptides; and preparation of antibodies. Any or all nucleic acids suitable for these uses are capable of being developed into reagent grade or kit format for commercialization as products. Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Probes and Primers. Among the uses of the disclosed LDCAM nucleic acids, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human LDCAM homologues.

Chromosome Mapping. The nucleic acids encoding LDCAM polypeptides, and the disclosed fragments and combinations of these nucleic acids, can be used by those skilled in the art using well-known techniques to identify the human chromosome to which these nucleic acids map. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution). For example, chromosomes can be mapped by radiation hybridization. PCR is performed using the Whitehead Institute/MIT Center for Genome Research Genebridge4 panel of 93 radiation hybrids, using primers that lie within a putative exon of the gene of interest and which amplify a product from human genomic DNA, but do not amplify hamster genomic DNA. The PCR results are converted into a data vector that is submitted to the Whitehead/MIT Radiation Mapping site (www-seq.wi.mit.edu). The data is scored and the chromosomal assignment and placement relative to known Sequence Tag Site (STS) markers on the radiation hybrid map is provided. Alternatively, the genomic sequences corresponding to nucleic acids encoding a LDCAM polypeptide are mapped by comparison to sequences in public and proprietary databases, such as the GenBank non-redundant database (ncbi.nlm.nih.gov/BLAST), Locuslink (ncbi.nlm.nih.gov:80/LocusLink/), Unigene (ncbi.nlm.nih.gov/cgi-bin/UniGene), AceView (ncbi.nlm.nih.gov/AceView), Online Mendelian Inheritance in Man (OMIM) (ncbi.nlm.nih.gov/Omim), Gene Map Viewer (ncbi.nlm.nih.gov/genemap), and proprietary databases such as the Celera Discovery System (celera.com). These computer analyses of available genomic sequence information can provide the identification of the specific chromosomal location of genomic sequences corresponding to sequences encoding LDCAM polypeptides, and the unique genetic mapping relationships between the LDCAM genomic sequences and the genetic map locations of known human genetic disorders.

Diagnostics and Gene Therapy. The nucleic acids encoding LDCAM polypeptides, and the disclosed fragments and combinations of these nucleic acids can be used by one skilled in the art using well-known techniques to analyze abnormalities associated with the genes corresponding to these polypeptides. This enables one to distinguish conditions in which this marker is rearranged or deleted. In addition, nucleic acids of the invention or a fragment thereof can be used as a positional marker to map other genes of unknown location. The DNA can be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes can be detected in in vitro diagnostic assays, and by comparison of a native nucleotide sequence disclosed herein with that of a gene derived from a person suspected of harboring a defect in this gene.

Carriers and Delivery Agents. The LDCAM polypeptides (fragments, variants, fusion proteins, derivatives, oligomers, and the like), antagonists and agonists (which includes antibodies of all sorts described herein) as well as peptibodies and the like, can also find use as transporters for delivering agents to cells. The LDCAM polypeptides (fragments, variants, fusion proteins, derivatives, oligomers, and the like), antagonists and agonists (which includes antibodies of all sorts described herein) as well as peptibodies and the like can be used to deliver diagnostic or therapeutic agents to such cells in in vitro or in vivo procedures. Detectable (diagnostic) and therapeutic agents that can be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to the polypeptide by any suitable conventional procedure. The polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). A number of techniques for radiolabeling polypeptides are known. Radionuclide metals can be attached to polypeptides by using a suitable bifunctional chelating agent, for example. Conjugates comprising polypeptides and a suitable diagnostic or therapeutic agent (preferably covalently linked) are thus prepared. The conjugates are administered or otherwise employed in an amount appropriate for the particular application.

7. Therapeutic Application of LDCAM Antagonists or Agonists

The LDCAM antatonists and agonists, which are defined above and includes, but is not limited to, LDCAM polypeptides (as well as variants thereof, fragments, fusion proteins, derivatives, mimetopes, and the like), anti-LDCAM antibodies, anti-LDCAM peptibodies, CRTAM polypeptides (as well as variants thereof, fragments, fusion proteins, derivatives, mimetopes, and the like), anti-CRTAM antibodies and anti-CRTAM peptibodies are likely to be useful for treating medical conditions and diseases. Therefore, throughout the specification, "LDCAM antagonists or agonists" refers to all the various embodiments described in the definition of LDCAM antagonists or agonists.

In general, these diseases include, but not limited to, autoimmune disease, inflammation, cancer, infectious disease, as well as other conditions as described in more detail below. The therapeutic molecule or molecules to be used will depend on the etiology of the condition to be treated and the biological pathways involved. For example, an antagonist or agonist of the LDCAM/CRTAM, or LDCAM/LDCAM interaction can be selected for treatment of conditions involving cell binding, intracellular signaling, cellular activation, cytokine production that influence autoimmune disease, inflammation, cancer, infectious disease, etc. More specifically, a LDCAM agonist would "cool down" inflammatory processes, such as the proliferation of T-cells and the release of proinflammatory cytokines, such as but not limited to Interferon-gamma and IL-2, as described in the Examples. LDCAM agonists may be used in the treatment of autoimmune diseases, contact hypersensitivity, multiple sclerosis, graft rejection and the like. A LDCAM antagonist would enhance immune responses by interfering with the binding of LDCAM and CRTAM. Thus, a LDCAM antagonist would be useful in treating diseases and conditions that require an enhanced immune response, and in particular diseases characterized by a deficient T-cell response, such as but not limited to cancer, infection (viral or bacterial), and in some transplantation settings.

Antibodies to the BDCA3+ DC may be used in a variety of therapeutic settings, including, but not limited to modulate the function of BDCA3+ DC to influence the outcome of immune responses, such as targeting the BDCA3+ DCs with the 1F12 antibody linked to a antigen and thereby specifically delivering the antigen to the DC population that may confer immune tolerance to that antigen. Alternatively, in the presence of inflammatory signals, such as proinflammatory cytokines, chemokines and the like, the targeted antigen would heighten antigen specific immune responses to that antigen. The 1F12 antibody and other anti-LDCAM antibodies may be used for prognostic purposes, such as comparative or relative BDCA3+ DC quantification in normal and pathological tissues. The 1F12 antibody and other anti-LDCAM antibodies may be used to purify or isolate BDCA3+ DC from diverse bodily fluids, organs and tissues. The 1F12 antibody and other anti-LDCAM antibodies may be used to deplete BDCA3+ DC in vivo or interfere with their immunological function, such as, but not limited to T-cell priming, DC homing, cross-presentation of antigen to CD8+ T-cells, and the like. Because cross-presentation of antigens and cross-tolerance to antigens are cellular mechanisms central to many autoimmune diseases, transplantation and cancer, 1F12 antibody and other anti-LDCAM antibodies may be used to treat these disorders by modulating the immune responses accordingly through the BDCA3+ DC.

In addition, 1F12 antibody and other anti-LDCAM antibodies may be used in ex vivo cell therapy. The BDCA3+

DC may be isolated with the 1F12 antibody and other anti-LDCAM antibodies and manipulated ex vivo and reintroduced into the patient to treat disease. For exemplary purposes only, one could break immune tolerance to cancer by exposing the isolated BDCA3+ DC to cancer antigens (such as, but not limted to, those presented in the Table 2, supra) and infusing the BDCA3+ DC/processed cancer antigen back into the patient. In alternavie embodiments, the cancer antigen may come from the patient and may be in the form of cancer cells. BDCA3+ DC are capable of phagocytosing apoptotic cells and presenting this exogenous antigen to CD8+ T-cells for generating cancer-specific CTL effectors. Thus, the cancer cells or tumor removed from the patient may be exposed to apoptosis-inducing stimuli, such as irradiation or chemicals/drugs, and exposed to the patient's isolated BDCA3+ DC. The BDCA3+ DC would phagocytose the apoptotic cancer cells and present cancer antigens in the context of class-I MHC. These DCs would be reinfused into the patient and would prime a CTL effector response to the patient's own cancer antigens. The CTL effectors would lyse only those cells expressing the patient's cancer antigens. This form of ex vivo therapy may be used in combination with other conventional therapies, such as, but not limited to surgery, radiation and/or chemotherapy.

Figure 17:
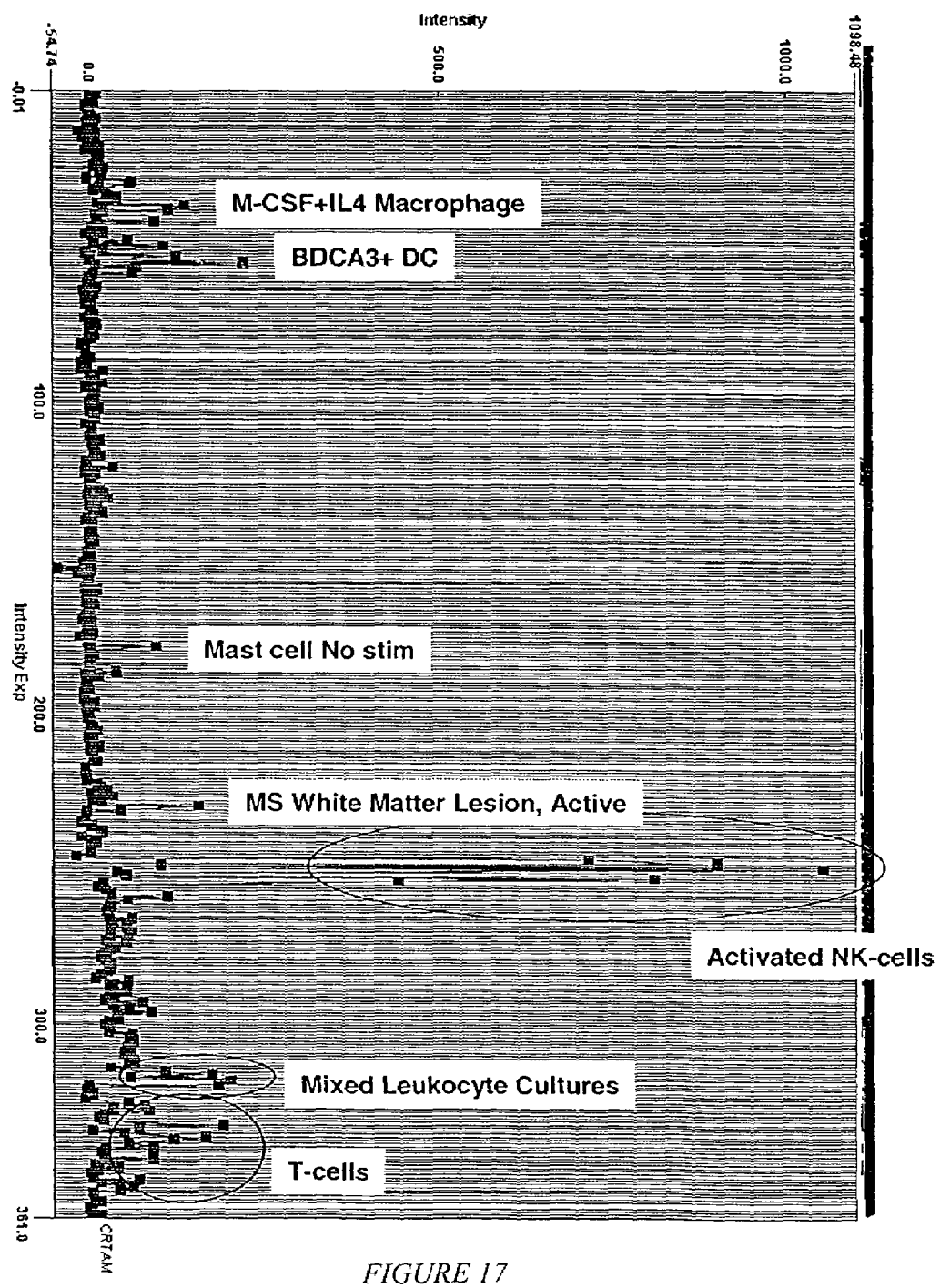
FIG. 17 is differential expression data showing CRTAM is expressed to a larger extent in macrophages, BDCA3+ DC, mast cells, active multiple sclerosis white matter lesions, activated NK cells, mixed leukocytes, and T-cells.

Example 19 describes the discovery that CRTAM is a cognate or binding partner of LDCAM. LDCAM is expressed on dendritic cells and especially on the newly-discovered BDCA3+ dendritic cells, which are likely to have the unique immunological properties described above. CRTAM is expressed on activated T-cells (see FIG. 17 showing increased expression as determined by differential expression experiments). Both CD4+ and CD8+ T-cells express CRTAM, and at especially high levels on activated CD8+ T-cells. Therefore, the interaction between LDCAM and CRTAM may be involved in forming an immunological synapse between antigen presenting cells and lymphoid effector cells (such as between dendritic cells, including the BDCA3+ DC and T-cells, including class-I-restriced T-cells, such as CD8+ T-cells). Without being bound by theory, it may be that the LDCAM/CRTAM interaction between antigen presenting cells and T-cells is a negative regulator of killing. As shown in the Examples, the LDCAM/CRTAM interaction prevented activation of T-cells in the presence of a variety of T-cell activation stimuli, including anti-CD3 sitmulation and various mitogens. It may be that the interaction between LDCAM/CRTAM is a way for the antigen presenting cell to engage and prime the T-cell to the antigen but not be killed by the T-cell. This would permit multiple engagements by the antigen presenting cell, which is known to occur in DC.

Furthermore, it has been reported that CRTAM is expressed on activated NK and NK-T cells and that these cells have been implicated in the immunopathology of diabetes (Kennedy, et al., *J Leuk Bio* 67 (2000)). This data has been confirmed by differential expression experiments, which show that CRTAM is highly expressed on activated NK cells (FIG. 17). Therefore, the interaction between LDCAM and CRTAM may be involved in forming an immunological synapse between antigen presenting cells and NK-T cells. Thus, LDCAM antagonists of the present invention may be used to inhibit or block the interaction between antigen presenting cells (such as DC) and NK and/or NK-T cells that cause symptoms of disease in diabetes.

Additionally, LDCAM has been shown to be expressed on neuronal tissue, particularly in the brain (Biederer, et al., *Science* 297, 1525 (2002)). Therefore, the interaction between LDCAM on neurons and CRTAM on T-cells may be involved in forming an immunological synapse between the nervous system and the immune system. Thus, LDCAM antagonists of the present invention may be used to inhibit or block the interaction between immune cells expressing CRTAM (such as T cells) and neurons that express LDCAM and thereby prevent or treat disease resulting from that interaction. Examples include multiple sclerosis and other diseases of the nervous system listed below. It has been determined by differential expression experiments that CRTAM is expressed on active multiple sclerosis (MS) lesions (FIG. 17). This provides a sound basis on which to predict that a LDCAM agonist would decrease the proinflammatory response of activated T-cells and in particular prevent or diminish the release of Interferon-gamma from activated T-cells. It is well-known in the art that Interferon-gamma is increased in active MS lesions and in circulating levels in patients experiencing relapse and that increased levels of Interferon-gamma is correlated with worsening symptoms and myelin destruction. Therefore, a LDCAM agonist would prevent or diminish the autoimmune-like destruction of the white matter by blocking T-cells from releasing proinflammatory cytokines such as Interferon-gamma.

In additional embodiments, LDCAM antagonists may be used to treat subjects with cancer, such as, but not limited to: leukemia, Epstein-Barr virus-positive nasopharyngeal carcinoma, colon, stomach, prostate, renal cell, cervical and ovarian cancers, lung cancermammalian sarcomas and carcinomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, such as acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Various lymphoproliferative disorders also are treatable including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sézary syndrome.

LDCAM antagonists may also be used in combination with other recognized treatments known in the art. For example, in the treatment of cancer, LDCAM antagonists and agonists may be used in combination with surgery, chemotherapy, radiation therapy, adoptive immunotherapy and the like. One underlying rationale is that tumor bulk is minimal and/or tumor cells are shed into the circulation during and following surgery and immunotherapy through LDCAM antagonists may be more effective in this situation. In a specific embodiment, the preventive and therapeutic utility of the invention is directed at enhancing the immunocompetence of the cancer subject either before surgery, at or after surgery, and at inducing tumor-specific immunity to cancer cells, with the objective being inhibition of cancer, and with the ultimate clinical objective being cancer regression and/or eradication.

The effect of LDCAM antagonists on progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens; d) changes in the morphology of tumors using techniques such as a computed tomographic (CT) scan; e) changes in levels of putative biomarkers of risk for a particular cancer in individuals at high risk, and f) changes in the morphology of tumors. Alternatively, immune responses to the antigen of interest may be measured using standard techniques, such as CTL assays, proliferation assays, antibody capture assays, and the like.

In alternative embodiments, LDCAM antagonists and agonists may be combined with adoptive immunotherapy using antigen presenting cells (APC) sensitized with one or more of the antigens described above. Adoptive immunotherapy refers to a therapeutic approach for treating infectious diseases or cancer in which immune cells are administered to a host with the aim that the cells mediate specific immunity, either directly or indirectly, to the infected cells or tumor cells and/or antigenic components, and result in treatment of the infectious disease or regression of the tumor. In one embodiment, the antigen-sensitized APC can be administered prior to, concurrently with or after administration of a vaccine. Furthermore, the mode of administration for adoptive immunotherapy can be varied, including but not limited to, e.g., subcutaneously, intravenously, intraperitoneally, intramuscularly, intradermally or mucosally.

LDCAM agonists may be used to treat cardiovascular disease. Embodiments of the present invention include methods of treating cardiovascular disease in a subject having having cardiovascular disease comprising administering an effective amount of one or more LDCAM agonists, alone or in any combination.

Cardiovascular disease includes disease states having pathophysiology of the heart and vasculature systems, as well as organs and systems compromised by disease states of the heart and vasculature systems. Examples include, but are not limited to: inflammation of the heart and/or vasculature such as myocarditis, chronic autoimmune myocarditis, bacterial and viral myocarditis, as well as infective endocarditis; heart failure; congestive heart failure; chronic heart failure; cachexia of heart failure; cardiomyopathy, including non-ischemic (dilated cardiomyopathy; idiopathic dilated cardiomyopathy; cardiogenic shock, heart failure secondary to extracorporeal circulatory support ("post-pump syndrome"), heart failure following ischemia/reperfusion injury, brain death associated heart failure (as described in Owen et al., 1999 (Circulation. 1999 May 18;99(19):2565-70)); hypertrophic cardiomyopathy; restrictive cardiomyopathy; non-ischemic systemic hypertension; valvular disease; arythmogenic right ventricular cardiomyopathy) and ischemic (atherogenesis; atherosclerosis; arteriosclerosis; peripheral vascular disease; coronary artery disease; infarctions, including stroke, transient ischemic attacks and myocardial infarctions). Additional disease states encompassed by the definition of cardiovascular disease include: aneurysms; arteritis; angina; embolism; platelet-associated ischemic disorders; ischemia/reperfusion injury; restenosis; mitral and/or tricuspid regurgitation; mitral stenosis; silent myocardial ischemia; Raynaud's phenomena; thrombosis; deep venous thrombosis; pulmonary embolism; thrombotic microangiopathies including thrombotic thrombocytopenic purpura (TTP) and hemolytic uremic syndrome (HUS), essential thrombocythemia, disseminated intravascular coagulation (DIC), and thrombosis and coagulopathies associated with exposure to a foreign or injured tissue surfacethrombophlebitis; vasculitis, including Kawasaki's vasculitis; Takayasu's arteritis; veno-occlusive disease, giant cell arteritis, Wegener's granulomatosis; Schoenlein-Henoch purpura, as well as cardiovascular disease arising from periodontal infections by one or more oral pathogens, such as bacteria.

Additional examples of the therapeutic uses of one or more LDCAM agonists include the treatment of individuals who suffer from coronary artery disease or injury following platelet-associated ischemic disorders including lung ischemia, coronary ischemia, and cerebral ischemia, and for the prevention of reocclusion following thrombosis, thrombotic disorders including coronary artery thrombosis, cerebral artery thrombosis, intracardiac thrombosis, peripheral artery thrombosis, venous thrombosis, thrombotic microangiopathies including thrombotic thrombocytopenic purpura (TTP) and hemolytic uremic syndrome (HUS), essential thrombocythemia, disseminated intravascular coagulation (DIC), and thrombosis and coagulopathies associated with exposure to a foreign or injured tissue surface, in combination with angioplasty, carotid endarterectomy, anastomosis of vascular grafts, and chronic cardiovascular devices such as in-dwelling catheters or shunts.

Further indications include subjects that are or will be undergoing angioplasty procedures (i.e., balloon angioplasty, laser angioplasty, coronary atherectomy and similar techniques), placement of endovascular prosthetic devices such as carotid, coronary, peripheral arterial or other endovascular stents, dialysis access devices, or procedures to treat peripheral vascular disease; individuals undergoing surgery that has a high risk of thrombus formation (i.e., coronary bypass surgery, insertion of a prosthetic valve or vessel and the like).

A number of pulmonary disorders also can be treated with the LDCAM agonists. One such condition is adult respiratory distress syndrome (ARDS), which is associated with elevated TNFα, and may be triggered by a variety of causes, including exposure to toxic chemicals, pancreatitis, trauma or other causes. The disclosed compounds, compositions and combination therapies of the invention also are useful for treating broncho-pulmonary dysplasia (BPD); lymphangioleiomyomatosis; and chronic fibrotic lung disease of preterm infants. In addition, the compounds, compositions and combination therapies of the invention are used to treat occupational lung diseases, including asbestosis, coal worker's pneumoconiosis, silicosis or similar conditions associated with long-term exposure to fine particles. In other aspects of the invention, the LDCAM agonists and combination therapies are used to treat pulmonary disorders, including chronic obstructive pulmonary disease (COPD) associated with chronic bronchitis or emphysema; fibrotic lung diseases, such as cystic fibrosis, idiopathic pulmonary fibrosis and radiation-induced pulmonary fibrosis; pulmonary sarcoidosis; and allergies, including allergic rhinitis, contact dermatitis, atopic dermatitis and asthma.

Other embodiments provide methods for using the LDCAM agonists or combination therapies to treat a variety of rheumatic disorders. These include: adult and juvenile rheumatoid arthritis; systemic lupus erythematosus; gout; osteoarthritis; polymyalgia rheumatica; seronegative spondylarthropathies, including ankylosing spondylitis; and Reiter's disease. The subject LDCAM agonists and combination therapies are used also to treat psoriatic arthritis and chronic Lyme arthritis. Also treatable with these LDCAM antagonists and agonists and combination therapies are Still's disease and uveitis associated with rheumatoid arthritis. In addition, the LDCAM agonists and combination therapies of the invention are used in treating disorders resulting in inflammation of the voluntary muscle, including dermatomyositis and polymyositis. Moreover, the LDCAM agonists and combinations disclosed herein are useful for treating sporadic inclusion body myositis, as TNFα may play a significant role in the progression of this muscle disease. In addition, the LDCAM antagonists and agonists and combinations disclosed herein are used to treat multicentric reticulohistiocytosis, a disease in which joint destruction and papular nodules of the face and hands are associated with excess production of proinflammatory cytokines by multinucleated giant cells.

Disorders associated with transplantation also are treatable with the disclosed LDCAM antagonists or combination therapies, such as graft-versus-host disease, and complications resulting from solid organ transplantation, including transplantion of heart, liver, lung, skin, kidney or other organs. LDCAM antagonists may be administered, for example, to prevent or inhibit the development of bronchiolitis obliterans after lung transplantation.

Various other medical disorders treatable with the disclosed LDCAM agonists and combination therapies include: multiple sclerosis; Behcet's syndrome; Sjogren's syndrome; autoimmune hemolytic anemia; beta thalassemia; amyotrophic lateral sclerosis (Lou Gehrig's Disease); Parkinson's disease; and tenosynovitis of unknown cause, as well as various autoimmune disorders or diseases associated with hereditary deficiencies.

LDCAM antagonists may be used in the treatment and/or prevention of viral infection, including infection by: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunga viruses, phleboviruses and Nairo viruses); Arena viridae (hemorrhagic fever viruses); Reoviridae (e.g., reoviruses, orbiviuises and rotaviruses); Birnaviridae; Hepadnaviridae (Hepatitis B virus); Parvoviridae (parvovirusies); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

LDCAM antagonists may be used in the treatment and/or prevention of infection by bacterium, including infection by: *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira*, and *Actinomyces israeli*.

In alternative embodiments, LDCAM antagonists may be used to treat or immunize subjects against infectious unicellular organisms, including infection by: schistosomes; trypanosomes; *Leishmania* species; filarial nematodes; trichomoniasis; sarcosporidiasis; *Taenia saginata, Taenia solium, Cryptococcus neoformans, Apergillus fumigatus, Histoplasma capsulatum, Coccidiodes immitis, trichinelosis, Blastomyces dermatitidis, Chlamydia trachomatis, Candida albicans, Plasmodium falciparum, Plasmodium vivax, Plasmodium malariae*, and *Toxoplasma gondii* and the like.

Further therapeutic applications include: ALS; Alzheimer's disease; asthma; atherosclerosis; autoimmune hemolytic anemia; cancer, particularly cancers related to B cells; cachexia/anorexia; chronic fatigue syndrome; cirrhosis (e.g., primary biliary cirrhosis); diabetes (e.g., insulin diabetes); fever; glomerulonephritis, including IgA glomerulonephritis and primary glomerulonephritis; Goodpasture's syndrome; Guillain-Barre syndrome; graft versus host disease; Hashimoto's thyroiditis; hemorrhagic shock; hyperalgesia; inflammatory bowel disease; inflammatory conditions of a joint, including osteoarthritis, psoriatic arthritis and rheumatoid arthritis; inflammatory conditions resulting from strain, sprain, cartilage damage, trauma, orthopedic surgery, infection or other disease processes; insulin-dependent diabetes mellitus; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; *Myasthenia gravis; myelogenous* (e.g., AML and CML) and other leukemias; myopathies (e.g., muscle protein metabolism, esp. in sepsis); neurotoxicity (e.g., as induced by HIV); osteoporosis; pain; Parkinson's disease; Pemphigus; polymyositis/dermatomyositis; pulmonary inflammation, including autoimmune pulmonary inflammation; psoriasis; Reiter's disease; reperfusion injury; septic shock; side effects from radiation therapy; Sjogren's syndrome; temporal mandibular joint disease; thrombocytopenia, including idiopathic thrombocytopenia and autoimmune neonatal thrombocytopenia; tumor metastasis; uveitis; and vasculitis.

Conditions of the gastrointestinal system also are treatable with LDCAM antagonists and agonists or combination therapies, including coeliac disease. LDCAM agonists and combination therapies of the invention are used to treat Crohn's disease; ulcerative colitis; idiopathic gastroparesis; pancreatitis, including chronic pancreatitis and lung injury associated with acute pancreatitis. Included also are methods for using LDCAM agonists and combination therapies for treating disorders of the genitourinary system, such as glomerulonephritis, including autoimmune glomerulonephritis, glomerulonephritis due to exposure to toxins or glomerulonephritis secondary to infections with haemolytic streptococci or other infectious agents.

8. Formulation and Administration of LDCAM Antagonists and Agonists

This invention provides pharmaceutical or therapeutic agents as compositions, and methods for treating a patient, preferably a mammalian patient, and most preferably a human patient, who is suffering from a medical disorder, and in particular a disorder mediated by LDCAM. Such LDCAM-mediated disorders include conditions caused (directly or indirectly) or exacerbated by binding between LDCAM and a binding partner, such as, but not limited to LDCAM, CRTAM and B7L-1. For purposes of this disclosure, the terms "illness," "disease," "medical condition," "abnormal condition" and the like are used interchangeably with the term "medical disorder." The terms "treat", "treating", and "treatment" used herein includes curative, preventative (e.g., prophylactic) and palliative or ameliorative treatment. For such therapeutic uses, LDCAM antagonists and agonists can be administered to the patient in need through well-known means. Pharmaceutical or therapeutic compositions of the present invention can contain one or more LDCAM antagonists and agonists in any form as described herein.

Therapeutically Effective Amount. In practicing the method of treatment or use of the present invention, a therapeutically effective amount of a therapeutic agent of the present invention is administered to a patient having a condition to be treated, preferably to treat or ameliorate diseases associated with the activity of a LDCAM antagonists and agonists. As used herein, the term "therapeutically effective amount" means the total amount of each therapeutic agent or other active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual therapeutic agent or active ingredient, administered alone, the term refers to that ingredient alone. When applied to a combination, the term refers to combined amounts of the ingredients that result in the therapeutic effect, whether administered in combination, serially or simultaneously. As used herein, the phrase "administering a therapeutically effective amount" of a therapeutic agent means that the patient is treated with said therapeutic agent in an amount and for a time sufficient to induce an improvement, and preferably a sustained improvement, in at least one indicator that reflects the severity of the disorder. An improvement is considered "sustained" if the patient exhibits the improvement on at least two occasions separated by one or more days, or more preferably, by one or more weeks. The degree of improvement is determined based on signs or symptoms, and determinations can also employ questionnaires that are administered to the patient, such as quality-of-life questionnaires. Various indicators that reflect the extent of the patient's illness can be assessed for determining whether the amount and time of the treatment is sufficient. The baseline value for the chosen indicator or indicators is established by examination of the patient prior to administration of the first dose of the therapeutic agent. Preferably, the baseline examination is done within about 60 days of administering the first dose. If the therapeutic agent is being administered to treat acute symptoms, the first dose is administered as soon as practically possible after the injury has occurred. Improvement is induced by administering therapeutic agents such as LDCAM antagonists or agonists until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating injuries or other acute conditions. Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Dosing. One skilled in the pertinent art will recognize that suitable dosages will vary, depending upon such factors as the nature and severity of the disorder to be treated, the patient's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the compound and can be readily determined by routine experimentation. A dose can be formulated in animal models to achieve a circulating plasma concentration range that includes the IC50 (i.e., the concentration of the test compound which achieves a half-maximal inhibition of symptoms) as determined in cell culture, while minimizing toxicities. Such information can be used to more accurately determine useful doses in humans. Ultimately, the attending physician will decide the amount of polypeptide of the present invention with which to treat each individual patient. Initially, the attending physician will administer low doses of polypeptide of the present invention and observe the patient's response. Larger doses of polypeptide of the present invention can be administered until the optimal therapeutic effect is obtained for the patient, and at that point the dosage is not increased further. It is contemplated that the various pharmaceutical compositions used to practice the method of the present invention should contain about 0.01 ng to about 100 mg (or about 0.1 ng to about 10 mg, or about 0.1 microgram to about 1 mg) of polypeptide of the present invention per kg body weight. In one embodiment of the invention, LDCAM antagonists and agonists are administered one time per week to treat the various medical disorders disclosed herein, in another embodiment is administered at least two times per week, and in another embodiment is administered at least three times per week. If injected, the effective amount of LDCAM antagonists and agonists per adult dose ranges from 1-20 mg/m$^2$, and preferably is about 5-12 mg/m$^2$.

Alternatively, a flat dose can be administered, whose amount may range from 5-100 mg/dose. Exemplary dose ranges for a flat dose to be administered by subcutaneous injection are 5-25 mg/dose, 25-50 mg/dose and 50-100 mg/dose. In one embodiment of the invention, the various indications described below are treated by administering a preparation acceptable for injection containing LDCAM antagonists and agonists at 25 mg/dose, or alternatively, containing 50 mg per dose. The 25 mg or 50 mg dose can be administered repeatedly, particularly for chronic conditions. If a route of administration other than injection is used, the dose is appropriately adjusted in accord with standard medical practices. In many instances, an improvement in a patient's condition will be obtained by injecting a dose of about 25 mg of LDCAM antagonists and agonists one to three times per week over a period of at least three weeks, or a dose of 50 mg of LDCAM antagonists and agonists one or two times per week for at least three weeks, though treatment for longer periods may be necessary to induce the desired degree of improvement. For incurable chronic conditions, the regimen can be continued indefinitely, with adjustments being made to dose and frequency if such are deemed necessary by the patient's physician. The foregoing doses are examples for an adult patient who is a person who is 18 years of age or older. For pediatric patients (age 4-17), a suitable regimen involves the subcutaneous injection of 0.4 mg/kg, up to a maximum dose of 25 mg of LDCAM antagonists and agonists, administered by subcutaneous injection one or more times per week. If an antibody against a LDCAM polypeptide is used as the LDCAM antagonist, a preferred dose range is 0.1 to 20 mg/kg, and more preferably is 1-10 mg/kg. Another preferred dose range for an anti-LDCAM polypeptide antibody is 0.75 to 7.5 mg/kg of body weight. Humanized antibodies are preferred, that is, antibodies in which only the antigen-binding portion of the antibody molecule is derived from a non-human source. Such antibodies can be injected or administered intravenously.

Formulations. Compositions comprising an effective amount of a LDCAM antagonist or agonist of the present invention (from whatever source derived, including without limitation from recombinant and non-recombinant sources), in combination with other components such as a physiologically acceptable diluent, carrier, or excipient, are provided herein. The term "pharmaceutically acceptable" means a non-toxic material that does not interfere with the effectiveness of the biological activity of the active ingredient(s). Formulations suitable for administration include aqueous and non-aqueous sterile injection solutions which can contain anti-oxidants, buffers, bacteriostats and solutes which render the formulation isotonic with the blood of the recipient; and aqueous and non-aqueous sterile suspensions which can include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences*, 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. In one preferred embodiment of the invention, sustained-release forms of LDCAM or LDCAM-Like polypeptides are used. Sustained-release forms suitable for use in the disclosed methods include, but are not limited to, LDCAM and/or LDCAM-Like polypeptides that are encapsulated in a slowly-dissolving biocompatible polymer (such as the alginate microparticles described in U.S. Pat. No. 6,036, 978), admixed with such a polymer (including topically applied hydrogels), and or encased in a biocompatible semi-permeable implant.

In one embodiment, sustained-release forms of LDCAM antagonists and agonists are used. Sustained-release forms suitable for use in the disclosed methods include, but are not limited to, LDCAM antagonists and agonists that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

One type of sustained release technology that may be used in administering soluble LDCAM antagonists and agonists therapeutic compositions is that utilizing hydrogel materials, for example, photopolymerizable hydrogels (Sawhney et al., *Macromolecules* 26:581; 1993). Similar hydrogels have been used to prevent postsurgical adhesion formation (Hill-West et al., *Obstet. Gynecol.* 83:59, 1994) and to prevent thrombosis and vessel narrowing following vascular injury (Hill-West et al., *Proc. Natl. Acad. Sci. USA* 91:5967, 1994). Polypeptides can be incorporated into such hydrogels to provide sustained, localized release of active agents (West and Hubbel, *Reactive Polymers* 25:139, 1995; Hill-West et al., *J. Surg. Res.* 58:759; 1995). The sustained, localized release LDCAM antagonists and agonists when incorporated into hydrogels would be amplified by the long half life of LDCAM antagonists and agonists.

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms; e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., *Pharma. Res.* (1990) 7: 565-9; Adjei et al. (1990), *Internatl. J. Pharmaceutics* 63: 135-44 (leuprolide acetate); Braquet et al. (1989), *J. Cardiovasc. Pharmacol.* 13 (suppl.5): s.143-146 (endothelin-1); Hubbard et al. (1989), *Annals Int. Med.* 3: 206-12 ($\alpha$1-antitrypsin); Smith et al. (1989), *J. Clin. Invest.* 84: 1145-6 ($\alpha$1-proteinase); Oswein et al. (March 1990), "Aerosolization of Proteins", *Proc. Symp. Resp. Drug Delivery II*, Keystone, Colorado (recombinant human growth hormone); Debs et al. (1988), *J. Immunol.* 140: 3482-8 (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 µm (or microns), most preferably 0.5 to 5 µm, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Combinations of Therapeutic Compounds. A LDCAM antagonists and agonists of the present invention may be active in multimers (e.g., heterodimers or homodimers) or complexes with itself or other polypeptides. As a result, pharmaceutical compositions of the invention may comprise a polypeptide of the invention in such multimeric or complexed form. The pharmaceutical composition of the invention may be in the form of a complex of the polypeptide(s) of present invention along with polypeptide or peptide antigens. The invention further includes the administration of LDCAM antagonists and agonists or concurrently with one or more other drugs that are administered to the same patient in combination with the LDCAM antagonists and agonists, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components can be administered in the same or in separate compositions, and by the same or different routes of administration. Examples of components that can be administered concurrently with the pharmaceutical compositions of the invention are: cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-17, IL-18, IFN, TNF0, TNF1, TNF2, G-CSF, Meg-CSF, thrombopoietin, stem cell factor, and erythropoietin, or inhibitors or antagonists of any of these factors. The pharmaceutical composition can further contain other agents that either enhance the activity of the polypeptide or compliment its activity or use in treatment. Such additional factors and/or agents may be included in the pharmaceutical composition to produce a synergistic effect with polypeptide of the invention, or to minimize side effects. Conversely, a LDCAM antagonists and agonists of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. Additional examples of drugs to be administered concurrently include but are not limited to antivirals, antibiotics, analgesics, corticosteroids, antagonists of inflammatory cytokines, non-steroidal anti-inflammatories, pentoxifylline, thalidomide, and disease-modifying antirheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose. Additionally, LDCAM antagonists and agonists can be combined with a second LDCAM antagonists and agonists, including an antibody or peptibody against a LDCAM and/or CRTAM polypeptide, or a LDCAM or CRTAM polypeptide-derived peptide that acts as a competitive inhibitor of a native LDCAM and/or CRTAM polypeptide.

The duration of treatment will vary, but typically repeated doses will be administered over at least a period of two weeks or longer, or may be adminstered indefinitely. Several rounds of treatment may be given, alternating with periods of no treatment. If discontinued, treatment may be resumed if a relapse of the cancer should occur.

Treatment of cancer with a LDCAM antagonists and agonists may be administered concurrently with other treatments, and may be administered concurrently with chemotherapy or radiation treatment. In one example, the LDCAM antagonists and agonists is given concurrently with an agent that is effective against a variety of tumor types, such as Apo2 ligand/TRAIL or an anti-angiogenic agent such as an antibody against VEGF or an antibody against the EGF receptor. The LDCAM antagonists and agonists treatment also may be combined with other treatments that target specific kinds of cancer, such as for example, monoclonal antibodies targeted to tumor-specific antigens, or with other treatments used for particular kinds of cancer. For example, breast cancer may treated with a LDCAM antagonists and agonists administered concurrently with chemotherapy, hormone treatment, tamoxifen, raloxifene or agents that target HER2, such as an anti-HER2 antibody such as HERCEPTIN® (Genentech, Inc.), or any combination thereof. In another example, chronic lymphocytic leukemia or non-Hodgkin's lymphoma is treated with a combination of a LDCAM antagonists and agonists and the anti-CD20 monoclonal antibody RITUXIN® (Genentech, Inc.). The invention also contemplates the concurrent administration of LDCAM antagonists and agonists with various soluble cytokine receptors or cytokines or other drugs used for chemotherapy of cancer. "Concurrent administration" encompasses simultaneous or sequential treatment with the components of the combination, as well as regimens in which the drugs are alternated, or wherein one component is administered long-term and the other(s) are administered intermittently. Such other drugs include, for example, bisphosphonates used to restore bone loss in cancer patients, or the use of more than one RANK antagonist administered concurrently. Examples of other drugs to be administered concurrently include but are not limited to antivirals, antibiotics, analgesics, corticosteroids, antagonists of inflammatory cytokines, DMARDs, various systemic chemotherapy regimens and non-steroidal anti-inflammatories, such as, for example, COX I or COX II inhibitors.

Routes of Administration. Any efficacious route of administration can be used to therapeutically administer LDCAM antagonists and agonists, including those compositions comprising nucleic acids. Parenteral administration includes injection, for example, via intra-articular, intravenous, intramuscular, intralesional, intraperitoneal or subcutaneous routes by bolus injection or by continuous infusion., and also includes localized administration, e.g., at a site of disease or injury. Other suitable means of administration include sustained release from implants; aerosol inhalation and/or insufflation.; eyedrops; vaginal or rectal suppositories; buccal preparations; oral preparations, including pills, syrups, lozenges, ice creams, or chewing gum; and topical preparations such as lotions, gels, sprays, ointments or other suitable techniques. Alternatively, polypeptideaceous LDCAM antagonists and agonists may be administered by implanting cultured cells that express the polypeptide, for example, by implanting cells that express LDCAM antagonists and agonists. Cells may also be cultured ex vivo in the presence of polypeptides of the present invention in order to modulate cell proliferation or to produce a desired effect on or activity in such cells. Treated cells can then be introduced in vivo for therapeutic purposes. The polypeptide of the instant invention may also be administered by the method of protein transduction. In this method, the LDCAM antagonists and agonists is covalently linked to a protein-transduction domain (PTD) such as, but not limited to, TAT, Antp, or VP22 (Schwarze et al., 2000, *Cell Biology* 10: 290-295). The PTD-linked peptides can then be transduced into cells by adding the peptides to tissue-culture media containing the cells (Schwarze et al., 1999, *Science* 285: 1569; Lindgren et al., 2000, *TiPS* 21: 99; Derossi et al., 1998, *Cell Biology* 8: 84; WO 00/34308; WO 99/29721; and WO 99/10376). In another embodiment, the patient's own cells are induced to produce LDCAM polypeptides or antagonists by transfection in vivo or ex vivo with a DNA that encodes LDCAM antagonists and agonists. This DNA can be introduced into the patient's cells, for example, by injecting naked DNA or liposome-encapsulated DNA that encodes LDCAM antagonists and agonists, or by other means of transfection. Nucleic acids of the invention can also be administered to patients by other known methods for introduction of nucleic acid into a cell or organism (including, without limitation, in the form of viral vectors or naked DNA). When LDCAM antagonists and agonists are administered in combination with one or more other biologically active compounds, these can be administered by the same or by different routes, and can be administered simultaneously, separately or sequentially.

Oral Administration. When a therapeutically effective amount of polypeptide of the present invention is administered orally, polypeptide of the present invention will be in the form of a tablet, capsule, powder, solution or elixir. When administered in tablet form, the pharmaceutical composition of the invention can additionally contain a solid carrier such as a gelatin or an adjuvant. The tablet, capsule, and powder contain from about 5 to 95% polypeptide of the present invention, and preferably from about 25 to 90% polypeptide of the present invention. When administered in liquid form, a liquid carrier such as water, petroleum, oils of animal or plant origin such as peanut oil, mineral oil, soybean oil, or sesame oil, or synthetic oils can be added. The liquid form of the pharmaceutical composition can further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide of the present invention, and preferably from about 1 to 50% polypeptide of the present invention.

Intravenous Administration. When a therapeutically effective amount of polypeptide of the present invention is administered by intravenous, cutaneous or subcutaneous injection, polypeptide of the present invention will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to polypeptide of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention can also contain stabilizers, preservatives, buffers, antioxidants, or other additives known to those of skill in the art. The duration of intravenous therapy using the pharmaceutical composition of the present invention will vary, depending on the severity of the disease being treated and the condition and potential idiosyncratic response of each individual patient. It is contemplated that the duration of each application of the polypeptide of the present invention will be in the range of 12 to 24 hours of continuous intravenous administration. Ultimately the attending physician will decide on the appropriate duration of intravenous therapy using the pharmaceutical composition of the present invention.

Bone and Tissue Administration. For compositions of the present invention which are useful for bone, cartilage, tendon or ligament disorders, the therapeutic method includes administering the composition topically, systematically, or locally as an implant or device. When administered, the therapeutic composition for use in this invention is, of course, in a pyrogen-free, physiologically acceptable form. Further, the composition can desirably be encapsulated or injected in a viscous form for delivery to the site of bone, cartilage or tissue damage. Topical administration may be suitable for wound healing and tissue repair. Therapeutically useful agents other than a polypeptide of the invention which may also optionally be included in the composition as described above, can alternatively or additionally, be administered simultaneously or sequentially with the composition in the methods of the invention. Preferably for bone and/or cartilage formation, the composition would include a matrix capable of delivering the polypeptide-containing composition to the site of bone and/or cartilage damage, providing a structure for the developing bone and cartilage and optimally capable of being resorbed into the body. Such matrices can be formed of materials presently in use for other implanted medical applications. The choice of matrix material is based on biocompatibility, biodegradability, mechanical properties, cosmetic appearance and interface properties. The particular application of the compositions will define the appropriate formulation. Potential matrices for the compositions can be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure polypeptides or extracellular matrix components. Other potential matrices are nonbiodegradable and chemically defined, such as sintered hydroxapatite, bioglass, aluminates, or other ceramics Matrices can be comprised of combinations of any of the above mentioned types of material, such as polylactic acid and hydroxyapatite or collagen and tricalciumphosphate. The bioceramics can be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix. A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethyl-cellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorbtion of the polypeptide from the polymer matrix and to provide appropriate handling of the composition, yet not so much that the progenitor cells are prevented from infiltrating the matrix, thereby providing the polypeptide the opportunity to assist the osteogenic activity of the progenitor cells. In further compositions, polypeptides of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-alpha and TGF-beta), and insulin-like growth factor (IGF). The therapeutic compositions are also presently valuable for veterinary applications. Particularly domestic animals and thoroughbred horses, in addition to humans, are desired patients for such treatment with polypeptides of the present invention. The dosage regimen of a polypeptide-containing pharmaceutical composition to be used in tissue regeneration will be determined by the attending physician considering various factors which modify the action of the polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage can vary with the type of matrix used in the reconstitution and with inclusion of other polypeptides in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Veterinary Uses. In addition to human patients, LDCAM antagonists and agonists are useful in the treatment of disease conditions in non-human animals, such as pets (dogs, cats, birds, primates, etc.), domestic farm animals (horses cattle, sheep, pigs, birds, etc.), or any animal that suffers from a condition mediated by LDCAM antagonists and agonists In such instances, an appropriate dose can be determined according to the animal's body weight. For example a dose of 0.2-1 mg/kg may be used. Alternatively, the dose is determined according to the animal's surface area, an exemplary dose ranging from 0.1-20 mg/m$^2$, or more preferably, from 5-12 mg/m$^2$. For small animals, such as dogs or cats, a suitable dose is 0.4 mg/kg. In a preferred embodiment, LDCAM antagonists and agonists (preferably constructed from genes derived from the same species as the patient), is administered by injection or other suitable route one or more times per week until the animal's condition is improved, or it can be administered indefinitely.

Manufacture of Medicaments. The present invention also relates to the use of LDCAM antagonists and agonists, as variously defined herein in the manufacture of a medicament for the prevention or therapeutic treatment of each medical disorder disclosed herein.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are offered by way of illustration, and not limitation.

| Sequence Identity Numbers and Associated Molecules | |
|---|---|
| SEQ ID NO. | Molecule |
| 1 | DNA sequence for human LDCAM |
| 2 | Amino acid sequence for human LDCAM |
| 3 | DNA sequence for murine LDCAM |
| 4 | Amino acid sequence for murine LDCAM |
| 5 | PCR oligo primer for LDCAM-Fc construct |
| 6 | PCR oligo primer for LDCAM-Fc construct |
| 7 | DNA sequence for the long extracellular domain of human B7L-1 |
| 8 | Amino acid sequence for the long extracellular domain of human B7L-1 |
| 9 | DNA sequence for the short extracellular domain of human B7L-1 |
| 10 | Amino acid sequence for the short extracellular domain of human B7L-1 |
| 11 | Amino acid sequence for human CRTAM |
| 12 | Amino acid sequence for the variable heavy chain of the 1F12 antibody (FIG. 6) |
| 13 | Amino acid sequence for the variable light chain of the 1F12 antibody (FIG. 6) |

EXAMPLES

Example 1

Preparing B7L-1/Fc Fusion Protein

The following describes generating a human B7L-1/Fc protein which was used to identify cells to which B7L-1 binds. The fusion protein includes the soluble extracellular region of human B7L-1 and the mutein human Fc region and was prepared by first isolating cDNA encoding the extracellular region of human B7L-1 using primers which flank the extracellular region of B7L-1 (See U.S. Pat. No. 5,011,912).

To isolate the nucleotides that encode the extracellular domain of B7L-1 (nucleotides 108-1249 of SEQ ID NO:1 of copending application Ser. No. 60/095,663 filed Aug. 7, 1998) oligonucleotides that flank the extracellular region of B7L-1 were used as primers in a PCR reaction to obtain a PCR product from clone #44904 which was the template in the reaction. The resulting PCR product was digested with SalI and BglII restriction enzymes at the SalI and BglII sites incorporated by the primers. The resulting fragment was ligated into an expression vector (pDC409) containing the human IgG1 Fc region mutated to lower Fc receptor binding.

The resulting DNA construct was transfected into the monkey kidney cell lines CV-1/EBNA (with co-transfection of psv3neo). After 7 days of culture in medium containing 0.5% low immunoglobulin bovine serum, a solution of 0.2% azide was added to the supernatant and the supernatant was filtered through a 0.22 μm filter. Then approximately 1L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 30 mL of PBS solution and bound fusion protein was eluted from the HPLC column with citric acid adjusted to pH 3.0. Eluted purified fusion protein was neutralized as it eluted using 1M HEPES solution at pH 7.4.

Example 2

B7L-1 Binding Studies

The B7L-1/Fc fusion protein prepared as described in Example 1 was used to screen cell lines for B7L-1 binding using quantitative binding studies according to standard flow cytometry methodologies. For each cell line screened, the procedure involved incubating cells blocked with 2% FCS (fetal calf serum), 5% normal goat serum and 5% rabbit serum in PBS for 1 hour. Then the blocked cells were incubated with 5 μg/mL of B7L-1/Fc fusion protein in 2% FCS, 5% goat serum and 5% rabbit serum in PBS. Following the incubation the sample was washed 2 times with FACS buffer (2% FCS in PBS) and then treated with mouse anti human Fc/biotin (purchased from Jackson Research) and SAPE (streptavidin-phycoerythrin purchased from Molecular Probes). This treatment causes the antihuman Fc/biotin to bind to any bound B7L-1/Fc and the SAPE to bind to the anti-human Fc/biotin resulting in a fluorescent identifying label on B7L-1/Fc which is bound to cells. The cells were analyzed for any bound protein using fluorescent detection flow cytometry. The results indicated that human B7L-1 binds well to human lung epithelial line (WI-28), human B lymphoblastoid lines (Daudi and PAE8LBM1), human fresh tonsillar B cells, murine CD8$^+$ dendritic cells from spleens/ lymph nodes of flt3-L treated animals and murine T cell lymphoma S49.1.

Example 3

Screening WI-26 Expression Library for B7L-1 Counter Receptors

The following describes screening a expression cloning library with the B7L-1/Fc fusion protein prepared as described in Example 1. The expression library was prepared from the human cell line WI-26 using methods described in *Current Protocols In Molecular Biology*, Vol. 1, (1987). Using standard indirect-binding methods, transfected monolayers of CV1/EBNA cells were assayed by slide autoradiography for expression of a B7L-1 counter receptor using radioiodinated B7L-1/Fc fusion protein. Positive slides showing cells expressing a counter receptor were identified and one pool containing approximately 2,000 individual clones was identified as potentially positive for binding the B7L-1/Fc fusion protein.

The pool was titered and plated and then scraped to provide pooled plasmid DNA for transfection into CV1/EBNA cells. After screening the smaller pools, one pool contained clones that were positive for B7L-1 counter receptor as indicated by the presence of an expressed gene product capable of binding to B7L-1/Fc. The positive pool was titered and plated to obtain individual colonies. DNA was isolated from each potential candidate clone, retransfected and rescreened. The resulting positive clones contained a cDNA insert of 1535 nucleotides. The cDNA coding region of the B7L-1 counter receptor (LDCAM) corresponds to that disclosed SEQ ID NO:1. The amino acid sequence encoded by SEQ ID NO:1 is disclosed in SEQ ID NO:2.

Example 4

Expressing Human LDCAM

To following describes expressing full length membrane-bound human LDCAM in CV1/EBNA cells. A vector construct for expressing human LDCAM was prepared by ligating the coding region of SEQ ID NO:1 into a pDC409 expression vector. The expression vector was then transfected in CV1/EBNA cells and LDCAM was expressed using techniques described in McMahan et al., *EMBO J.* 10:2821,1991.

After the cells were shocked and incubated for several days, cells having membrane bound LDCAM were harvested, fixed in 1% paraformaldehyde, washed and used in their intact form.

To express a soluble form of LDCAM that includes the LDCAM extracellular region encoded by nucleotides 8 to 1130 of SEQ ID NO:1, a vector construct is prepared by ligating the extracellular coding region of SEQ ID NO:1 into a pDC409 expression vector. The vector is transfected in CV1/EBNA cells Following a 3 day incubation period in fresh medium, soluble LDCAM is recovered by collecting CV1/EBNA cell supernatants containing the soluble form and isolating LDCAM using HPLC techniques or affinity chromatography techniques.

Example 5

LDCAM Binding Studies

In order to identify cell lines to which LDCAM binds, the LDCAM/Fc fusion protein, described in Example 9 below, was prepared and used in cell binding and FACS assays. Using standard cell binding and FACS methodologies, LDCAM was found to bind to the B lymphoblastoid cell lines, DAUDI and PAE8LBM1, cells transfected with human B7L-1, cells transfected with LDCAM, S49.1 cells, and to the lymphoid DCs from spleens and lymph nodes of Flt3-L treated mice.

Example 6

Identifying Tissue Expressing LDCAM

Using standard RT-PCR methodologies, Northern analyses and EST data base (GENBANK) sequence matching, a number of cell lines were examined for mRNA expression of human LDCAM and mouse LDCAM. The results demonstrated that LDCAM has a widespread tissue distribution. Expression of human LDCAM was found in breast, retina, fetal liver, spleen, fetal heart, lung, muscle, placenta, thyroid, and lung carcinoma. Mouse mRNA LDCAM was found in whole embryo, testes, and triple negative cells.

Example 7

Isolating Murine LDCAM

Since the soluble human B7L-1 demonstrated binding to the murine lymphoma S49.1 (Example 2), a S49.1 expression library was screened for murine LDCAM cDNA clones. The process involved RT-PCR methodologies using the S49.1 cell line RNA and primers described in SEQ ID NO:7 and SEQ ID NO:8. These primers are based on a murine EST, discovered in a database and having homology to human LDCAM. The cDNAs were amplified by PCR using the primers, confirming the murine LDCAM is present in S49.1 cells.

The amplified product was cloned into a cloning vector and clones containing a LDCAM cDNA insert were detected by hybridization with an oligonucleotide complementary to the human LDCAM coding region. To detect cDNAs with 5' extensions as compared with human LDCAM an oligonucleotide primer complementary to the 5' end of the coding region and a primer complementary to vector sequences adjacent to the cDNA insert were used to perform anchored PCR so that the 5' region of the cDNA clones is amplified. The PCR products were examined by gel electrophoresis and their lengths were compared with a similarly derived amplification product from the human LDCAM cDNA. The cDNA inserts for the clones giving longer 5' PCR product were sequenced to give a murine LDCAM cDNA encoding all but the first 4 amino acids, as compared with the human LDCAM. The nucleotide sequence for murine LDCAM is given in SEQ ID NO:3. The amino acid sequence encoded by the nucleotide sequence of SEQ ID NO:3 is provided in SEQ ID NO:4.

Example 8

Expressing Murine LDCAM Polypeptide

To prepare a vector construct for expressing murine extracellular B7L-1 the coding region of SEQ ID NO:3 was ligated into a pDC409 expression vector. The expression vector was then transfected in CV1/EBNA cells and LDCAM was expressed using techniques described in McMahan et al., *EMBO J.* 10:2821,1991.

After the cells were shocked and incubated for several days, cell supernatants containing soluble murine LDCAM were collected and the protein was recovered using HPLC techniques.

Example 9

Preparing LDCAM/fusion Proteins

The following describes generating a human LDCAM/Fc protein which was used to identify cells to which LDCAM binds. The fusion protein includes the soluble extracellular region of human LDCAM and the mutein human Fc region and was prepared by first isolating cDNA encoding the extracellular region of human LDCAM using primers which flank the extracellular region of LDCAM (See U.S. Pat. No. 5,011,912).

To isolate the nucleotides that encode the extracellular domain of LDCAM, nucleotides 16-1137 of SEQ ID NO:1, oligonucleotides that flank the extracellular region of LDCAM were used as primers in a PCR reaction to obtain a PCR product from the WI-26 clone. The primers are shown in SEQ ID NO:5 and SEQ ID NO:6. The resulting PCR product was digested with Sal1 and Bg1II restriction enzymes at the Sal1 and Bg1II sites incorporated by the primers. The resulting fragment was ligated into an expression vector (pDC409) containing the human IgG1 Fc region mutated to lower Fc receptor binding.

The resulting DNA construct was transfected into the monkey kidney cell lines CV-1/EBNA. After 7 days of culture in medium containing 0.5% low immunoglobulin bovine serum, a solution of 0.2% azide was added to the supernatant and the supernatant was filtered through a 0.22 µm filter. Then approximately 1L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 30 mL of PBS solution and bound fusion protein was eluted from the HPLC column with citric acid adjusted to pH 3.0. Eluted purified fusion protein was neutralized as it eluted using 1M HEPES solution at pH 7.4.

Example 10

Monoclonal Antibodies to LDCAM

This example illustrates a method for preparing monoclonal antibodies to LDCAM. Purified LDCAM, a fragment thereof such as the extracellular domain, synthetic peptides or cells that express LDCAM can be used to generate monoclonal antibodies against LDCAM using conventional techniques, for example, those techniques described in U.S. Pat. No. 4,411,993. Briefly, mice are immunized with LDCAM as an immunogen emulsified in complete Freund's adjuvant, and injected in amounts ranging from 10-100 µg subcutaneously or intraperitoneally. Ten to twelve days later, the immunized animals are boosted with additional LDCAM emulsified in incomplete Freund's adjuvant. Mice are periodically boosted thereafter on a weekly to bi-weekly immunization schedule. Serum samples are periodically taken by retro-orbital bleeding or tail-tip excision to test for LDCAM antibodies by dot blot assay or ELISA (Enzyme-Linked Immunosorbent Assay).

Following detection of an appropriate antibody titer, positive animals are provided one last intravenous injection of LDCAM in saline. Three to four days later, the animals are sacrificed, spleen cells harvested, and spleen cells are fused to a murine myeloma cell line, e.g., NS1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified B7L-1 by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-LD-CAM monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to B7L-1.

Example 11

Detecting LDCAM Expression by Northern Blot Analyses

The following describes Northern Blot experiments carried out to identify tissue and cell types that express LDCAM polypeptides of the present invention.

Northern blots were generated by fractionating 5 µg to 10 µg of total RNA on a 1.2% agarose formaldehyde gel and blotting the RNA onto Hybond Nylon membranes (Amersham, Arlington Heights, Ill.). Standard northern blot generating procedures as described in Maniatis, (*Molecular Cloning: a Laboratory Manual*, Cold Spring Harbor Lab. Press, 1989) were used. Poly A+ multiple tissue blots containing 1 µg of mRNA from a number of different sources were purchased from Clonetech.

A riboprobe, containing the coding region of LDCAM, was generated using Promega's Riboprobe Combination Kit and T7 RNA Polymerase according to the manufacturer's instruction. The results of probing the Northern blots and visualizing the resulting x-ray film for positively binding probes show that a 5.0 kB hybridizing mRNA was detected for murine LDCAM in lung, liver, brain, testes and splenic dendritic cells. Additional hybridizing mRNA having different sizes included an approximately 1.9 kB mRNA in lung and testes; an approximately 3.0 kB mRNA in LPS stimulated bone marrow macrophages, lung and testes; an approximately 7.0 kB hybridizing mRNA in anti-T cell receptor antibody stimulated splenic T cells, LPS stimulated bone marrow macrophages, and testes; and, an approximately 9.0 kB hybridizing mRNA was detected in thymus and anti-T cell receptor antibody stimulated splenic T cells.

Example 12

Immune System Cell Binding Studies

The following describes FACS cell binding experiments that demonstrate that LDCAM binds to certain activated immune system cells. For study and comparison purposes, the binding characteristics of B7L-1 are also included. Cells studied included murine T cells, human T cells, murine B cells, murine NK cells, human endothelial cells, and human tumor cell lines.

To study murine T cell binding, BALB/c murine lymph node (LN) cells were cultured in culture medium alone and in the presence of different stimuli for 18-20 hours. The cultured cells were harvested and prepared for binding studies using B7L1l/Fc fusion protein, LDCAM/Fc fusion protein and a control Fc protein. Following an overnight culture BALB/c murine LN cells are typically >90% CD3+. Bound protein was detected using flow cytometric analysis. The results shown in Table I indicate observed binding expressed as mean fluorescence intensity units (MFI) on unstimulated T cells (medium) and on stimulated T cells (by stimuli).

TABLE I

| Fc | medium | Con A | TCR mAb | PHA |
|---|---|---|---|---|
| control Fc | 12.7 | 10.4 | 14.5 | 14.2 |
| B7L1Fc | 11.7 | 14.3 | 24.0 | 12.6 |
| LDCAM Fc | 18.7 | 51.7 | 230.0 | 91.4 |

When analyzed by T cell subsets, 75-80% of LN CD4+ murine T cells displayed detectable LDCAM binding after anti-TCR stimulation in vitro. About 50% of LN CD8+ murine T cells display detectable binding. In addition, CD4+ T cells exhibit higher levels of LDCAM binding than do CD8+ murine T cells. The results demonstrate that LDCAM/Fc binds at low levels to naïve T cells. However, after an overnight activation with polyclonal stimuli binding increased 5-20 fold depending on the stimuli. Of the stimuli studied PMA induces the least LDCAM binding to murine T cells, and anti-TCR induces the highest binding.

To study human T cells binding to LDCAM and it counterstructure B7L1, human peripheral blood (PB) T cells were cultured in culture medium only or in the presence of different stimuli for 18-20 hours. The cultured cells were harvested and prepared for binding studies using either B7L/1Fc fusion protein, LDCAM/Fc fusion protein and a control Fc protein. Bound protein on the human PB T cells was determined by flow cytometric analysis. Table II details results observed, expressed as MFI, on unstimulated T cells (medium) and on stimulated T cells (by stimuli).

TABLE II

| Fc | medium | Con A | PMA | PHA |
|---|---|---|---|---|
| control Fc | 4.7 | 4.8 | 3.5 | 4.3 |
| B7L1Fc | 6.3 | 7.5 | 4.5 | 5.7 |
| LDCAM Fc | 22.3 | 42.8 | 61.9 | 38.8 |

The results show that, PMA induces greater LDCAM binding on human T cells than it does on murine T cells. The presence of specific binding of LDCAM to both murine and human T cells in the absence of B7L1 binding suggests that LDCAM is binding to B7L1, or a different molecule and not to itself. Because studies indicate that T cells express little or no B7L1, LDCAM may have another binding partner.

Studies similar to those described above were performed to evaluate LDCAM and B7L1 binding to murine splenic B cells. Neither B7L1 nor LDCAM binding was detected on unstimulated murine B cells. Culturing murine splenic B cells with muCD40L or LPS induced low levels of LDCAM binding but no appreciable level of B7L1 binding was detected.

In order to study binding to murine NK cells, spleens were removed from IL-15 treated CB-17/SCID mice and used as a source for highly enriched and activated murine NK cells. Spleen cells isolated from IL-15 treated SCID mice are 60-80% DX-5 positive. DX-5 is a pan NK marker than is expressed on NK cells from many different strains of mice. Flow cytometric analysis was performed as described above to detect B7L1 and LDCAM binding to DX-5+ in vivo IL-15 activated murine NK cells. Table II gives the results of a binding murine NK cell binding study.

TABLE III

| Fc molecule | DX-5+ NK cell %+/MFI |
|---|---|
| control Fc | 8%/88 |
| B7L1Fc | 19%/265 |
| LDCAM Fc | 38%/432 |

In contrast to that which was observed on murine and human T cells, LDCAM and B7L1 binding can be detected on in vivo activated murine NK cells.

Results of experiments directed at studying B7L1 and LDCAM binding to human endothelial cells demonstrated no binding on human umbilical vein endothelial cells (HUVEC) from different donors. However, one HUVEC from one donor B7L1 did induce low levels of CD62E and CD106 compared to control Fc.

Table IV details the results of experiments directed at evaluating B7L1 and LDCAM binding to human tumor cell lines. The results are expressed as percentage of cells binding LDCAM or B7L1.

TABLE IV

| Cell line | Cell type | LDCAMFc (%+)** | B7L1Fc (%+)** |
|---|---|---|---|
| U937 | monocytic leukemia | 10 | 7 |
| K562 | erythroblastic leukemia | 7 | 5 |
| Jurkat | acute T cell leukemia | 10 | 7 |
| MP-1 | B-cell LCL | 46 | 10 |
| DAUDI-hi | B-cell Burkitt's | 8 | 6 |
| RPMI 8866 | B-cell lymphoma | 0 | 0 |
| #88EBV | B-cell LCL | 4 | 3 |
| #33EBV | B-cell LCL | 0 | 0 |
| Tonsil G EBV | B-cell LCL | 25 | 13 |
| MDA231 | breast adenocarcinoma | 8 | 9 |
| OVCAR-3 | ovarian carcinoma | 48 | 30 |
| H2126M1 | lung adenocarcinoma | 0 | 0 |

**binding of control Fc has been subtracted out so this is net % + cells binding over background The results show significant LDCAM binding on ovarian carcinoma cell line and 2 of the human B-cell tumor lines (MP-1 and Tonsil G). B7L1 also binds to these three tumor cell lines but a much lower levels. These results demonstrate that LDCAM is a marker for certain types of B cell lymphomas or different types of carcinomas. In addition, biological signaling mediated by LDCAM or B7L1 could mediate functional anti tumor effects on these types of tumors.

Example 13

Effects of LDCAM on T Cell Proliferation

The following discussion describes experiments performed to evaluate the effects of LDCAM on murine and human T cell proliferation induced by polyclonal stimuli.

LDCAM/Fc fusion protein and B7L1/Fc fusion protein were evaluated in a standard model of in vitro murine T cell proliferation. Lymph node (LN) cells were obtained from normal BALB/c mice and placed in culture in media. Varying amounts of control Fc, B7L1/Fc and LDCAM/Fc alone or in the presence of different polyclonal stimuli for T cells including ConA, PHA or immobilized TCR mAb were placed in the culture media.

The results of these experiments demonstrated that LDCAM strongly inhibits ConA induced murine T cell proliferation (50% inhibition at ~0.625 ug/ml), moderately inhibits PHA induced proliferation (50% inhibition at ~5 ug/ml) and does not effect the proliferation induced by immobilized TCR mAb. In human peripheral blood T cell proliferation assays, LDCAM inhibits ConA induced proliferation but does not effectively inhibit PHA or OKT3-induced proliferation. B7L1/Fc does not effect the proliferative responses of murine or human T cells.

Results suggest that the inhibitory effects of LDCAM/Fc on mitogen-induced murine and human T cell proliferation are due to inhibition of cytokine secretion (especially IL-2) or due to regulation of downstream responses of the T cell following activation and increases in the expression of the LDCAM binding partner. LDCAM may also modulate cell to cell interactions between T cells, T cells and APC or T cells and NK cells. The inability of LDCAM to inhibit TCR mAb induced proliferation suggests that cytokine dysregulation is occurring in that proliferation induced by ConA and PHA is very cytokine dependent where as that induced by anti TCR mAb is less so.

Example 14

Effects of LDCAM on Murine T Cell Cytokine Production

The following describes experiments performed in order to evaluate LDCAM for its effects on murine LN cell or purified T cell cytokine secretion following the in vivo activation of T cells with PHA, ConA and TCR mAb. Results are shown in Table V. The levels of cytokine detected are expressed in pg/ml.

TABLE V

| culture condition | Fc molecule | IL-2(pg/ml) | IFN-gamma(pg/ml) |
|---|---|---|---|
| media | None | <2 | <10 |
|  | control Fc | <2 | <10 |
|  | LDCAM/Fc | <2 | <10 |
| ConA | None | 366 | 100 |
|  | control Fc | 614 | 244 |
|  | LDCAM/Fc | <2 | <10 |
| PHA | None | 36 | 358 |
|  | control Fc | 39 | 354 |
|  | LDCAM/Fc | 10 | <10 |
| immob. TCR mAb | None | 1703 | 1114 |
|  | control Fc | 1722 | 1215 |
|  | LDCAM/Fc | 1642 | 1027 |

The results show that LDCAM/Fc significantly inhibits murine LN T cell IL-2 and IFN-gamma production that is induced by both ConA and PHA. When immobilized anti TCR mAb is used to induce cytokine production from murine T cell, less pronounced effects of LDCAM on cytokine production were observed. LDCAM decreased IFN-gamma production after TCR activation. In contrast, IL-2 production was not decreased after TCR activation. Very little IL-4 was generated by the T cells in these experiments so whether or not LDCAM effects T cell production of IL-4 or other additional cytokines/chemokines was not evaluated.

Example 15

Effects of LDCAM on Murine Mixed Cell Activation Assays

An in vitro mixed cell assay was developed to examine the ability of T cells to activate B cells through their CD40L/CD40 interaction. The assay involves culturing spleen cells and LN cells with anti-TCR mAb in vitro for 36 hours followed by the flow cytometric analysis T and B cell/APC cell activation that occurs after T cells become activated and interact with B cells/APCs.

Spleen cells were cultured with anti TCR mAb, ConA, PHA or in media only with control Fc or LDCAM/Fc for 36 hours. CD19+ B cell and CD3+ T cell activation was followed by examining cell surface expression of CD25, CD69, CD54, CD45Rb, CD44, CD28, CD23, CD86 and CD152 using two-color staining and flow cytometric analysis.

The results demonstrated that after activation with PHA or ConA the expression of CD69, CD54, and CD25 increases several fold on T cells and B cells in the culture. Compared to a control Fc which has little effect on these increases, LDCAM significantly reduced expression (almost to the same levels as non-activated T cells) of CD69, (CD54 and CD25 that are induced on both cells types in this culture system via activation with ConA. The ConA activates the T cells which express activation molecules (e.g. CD40L) on their surface. The activation molecules bind to receptors on the surface of B cells and activate the B cells to express various activation-related proteins on their cell surface. The inhibition PHA activated T and B cells occurred to a more moderate extent to that observed after activation with ConA.

In addition, LDCAM decreased the levels of CD45RB expressed on both CD3+ and CD3− in spleen cells cultured with ConA. This effect on decreasing CD45RB levels was more pronounced when LDCAM was cultured with spleen cells stimulated with TCR mAb and was not observed when PHA was used as a stimulus or when the cells were cultured in medium alone.

Using TCR mAb to stimulate the cultured spleen cells in the presence of a control Fc or LDCAM/Fc showed that the levels of CD69, CD25, and CD25 induced on T cells and B cells by this stimulus were not effected by LDCAM. However, LDCAM increased the expression of CD28 on both CD3+ T cells and non-T cells. In one experiment the increase was 5-10 fold and in the other experiments the increase was 50%. This was also observed in one experiment when ConA was used as a stimulus in addition to TCR mAb. LDCAM caused moderate decreases in the intensity of CD45RB expression on B cells (50% decrease) and T cells(20-30% decrease) after activation with TCR mAb.

Interestingly, LDCAM does not effect CD45RB expression on spleen cells when they are cultured in the absence of polyclonal T cell stimuli. CD45RB expression in rodents has been reported to decrease as T cells progress from naive to memory cells. Also different subpopulations of CD4+ T cells express high or low levels of CD45RB and mediate distinct immune functions in vivo.

The above discussed results suggest that under certain immune stimulation conditions, particularly stimulations by ConA and PHA, LDCAM inhibits T cell activation at the cellular level in mixed cell assays and inhibits T cell proliferation induced by these mitogens at least partially by decreasing IL-2 and IFN-gamma production.

While LDCAM modestly down-regulates IFN gamma production induced by TCR mAb-induced activation, it has little effect on IL-2 production in this system and does not effect proliferation of murine T cells induced by immobilized TCR mAb. LDCAM does cause an increase in the TCR mAb activated T-cell and B-cell expression of CD28 and a decrease in CD45RB expression. Based on these data, LDCAM or its binding partner on T cells can regulate (increase, decrease or redirect) T cell effector-dependent immune responses in vivo including but not limited to anti-tumor immune responses, DTH responses, and T-cell dependent anti-infectious disease immune responses.

The above results suggest that LDCAM is useful in modulating T cell activation pathways and can be used to treat autoimmune diseases and inflammation.

Example 16

LDCAM.Fc Binds to Murine NK Cells and Causes NK Cell Expansion

The following describes experiments that demonstrate that LDCAM binds to the surface of splenic NK cells constituitively and that activation of these cells with IL-15 increased the levels of LDCAM binding. The experiments also describes administering LDCAM:Fc to CB-17 SCID mice and the effects of the administration on NK cell expansion and activation in the spleen.

Twelve age-matched female CB-17/SCID mice were divided into 4 groups, with 3 animals per group. On day 0, day 1 and day 2, group I, group II, group III and group IV were administered the following proteins IP: group I mice received 10 µg of human IgG; group II mice received 10 µg of human IL-15; group III mice received 10 µg of human LDCAM:Fc (lot# 7488-16 from Immunex); and, group IV received 10 µg each of human LDCAM:Fc and human IL-15.

On day 3 (the $4^{th}$ day of the experiment), the mice were euthanized and their spleens were removed. Each spleen was enumerated separately and then pooled together for flow cytometric analysis. The number of NK cells in the spleen of each treated group was determined by flow cytometry using the DX-5 antibody as a pan-murine NK cell marker. In addition, other measures of NK cell activation including CD69 and CD54 expression were evaluated.

The results for the experiment are shown in Table VI. Administration of LDCAM:Fc alone (Group III) increased the total recovered spleen cell number by about 5-fold over the human IgG control group (Group I). Administration of human IL-15 alone, (Group II) increased the total recovered spleen cell number by about 9-fold over the control group (Group I). Combination treatment with IL-15 and LDCAM increased the spleen cell number additively.

The number of NK cells recovered from the spleens correlated with the total cell recovery in the spleen. More particularly, LDCAM induced about a 5-fold increase in recovered NK cells; IL-15 caused about a 9-fold increase in recovered NK cells; and, the combination of LDCAM and IL-15 induced about a 13-fold increase in the number of NK cells recovered from the spleens of treated mice. LDCAM also increased the number of NK cells in the spleen that expressed CD69 and CD54. This increase was due to overall NK cell expansion rather than specific increases in the expression of CD69 or CD54 on NK cells in vivo following LDCAM:Fc administration.

TABLE VI

| SCID Mice Group | spleen cell counts × $10^6$ | Number of Mice | % DX-5+ cells (NK) | # of NK cells recovered × $10^6$ |
| --- | --- | --- | --- | --- |
| Group I (human IgG control) | 2.3 | 3 | 67.8 | 1.6 |
| Group II (IL15 positive control) | 17.8 | 3 | 81.7 | 14.5 |
| Group III (LDCAM:Fc) | 10.25 | 3 | 51.2 | 5.3 |
| LDCAM:Fc and IL15 | 24.8 | 3 | 72.6 | 18.0 |

Example 17

Identification of Unique Flt3-Ligand-Derived Dendritic Cell Population

A rare population of cells (0.2% PBMC) in the blood of Flt3-ligand-treated humans has been identified that can prime naïve CD4+ and CD8+ allo-reactive T cells, which is one of the functional characteristic of dendritic cells (DC or DCs). Phase I clinical trials were conducted on healthy human volunteers and received a daily subcutaneous injection of 10 mg/kg/day Flt3-ligand (FL) for 10 days. Injection of Flt3-ligand was shown to greatly increase the number of circulating CD123++ pDC, CD1c+ DC as well as monocytes. In the course of this clinical study, a rare population of CD162++ cells expressing the Blood Dendritic Cell Antigen-3 (BDCA3) were identified. BDCA3+ DC represent 0.06% of total PBMCs in normal donors. The frequency of BDCA3+ DC increases 4 to 8 fold after Flt3-ligand injection. The nature of the antigen recognized by the anti-BDCA3 antibody was unknown, but seemed to be up-regulated by IL-3 stimulation, thus reinforcing the notion that CD15s− CD162++ DC might represent a more "mature" form of peripheral blood DC. As shown in FIG. 1, these cells display some myeloid characteristics and were identified in that they do not express sialyl-lewis-X (CD15s) and express bright levels of CD162 (PSGL1). Sialyl-lewis-X is a complex sugar expressed on the vast majority of blood DC. The presence of sialyl-lewis-X (CD15s) on surface proteins plays a role in DC transmigration through the vascular endothelium. The lack of CD15s expression on DC suggests that these cells might not be able to leave the blood stream through transmigration. Further phenotypic characterization of these cells revealed a myeloid-related phenotype (CD11c+, CD13++, CD33$^{dim}$). Interestingly, unlike other myeloid cells, CD15s−CD162++ blood DC do not express Fc-receptors nor CD11b. Expression of Fc-receptor is down modulated upon maturation and marks the transition from a antigen capture (immature) stage to an antigen-presentation (mature) stage. Thus, CD15s−CD162++ DC might be more mature than the other blood DC subsets.

To further characterize the DC population in an effort to identify cell surface molecules unique to the DC population, phage display whole cell panning and global gene profiling were employed. Global gene array analysis revealed that BDCA3+ DC are likely to be the human counterparts of mouse CD8a+ DC. As shown in FIG. 2, a number of different genes are preferentially expressed in both mouse CD8a+ and human BDCA3+ DC. Of those genes, only BDCA3+ DC and mouse CD8a+ DC express LDCAM (also referred to as Igsf4). These results show that BDCA3+ cells are better defined as Igsf4 expressing DC. These antigen presenting cells (APC) are likely the human counterpart of murine CD8a+ DC, a specialized population of DC involved in antigen cross-presentation/cross-tolerance. Cross-presentation/tolerance is a cellular mechanism that plays a determining role in many autoimmune diseases, inflammation processes, as well as in transplantation. Targeting BDCA3+ DC (using various forms of antibodies, peptibodies, soluble proteins, such as LDCAM and/or CRTAM) may be important in many therapeutic areas (as described above).

Figure 3:
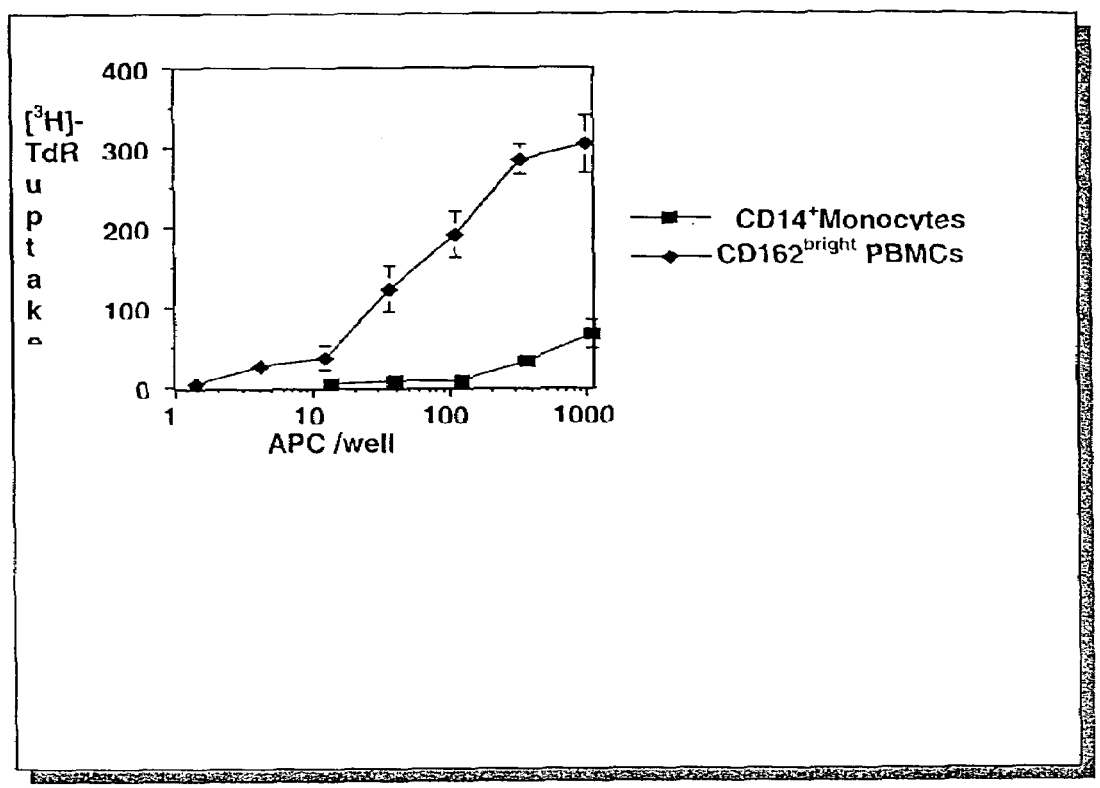
FIG. 3 is a graph showing that human BDCA3+ dendritic cells are potent allo-stimulators.

To determine the allo-activity of the DC population, CD162++ and CD14+ cells were purified from the blood of Flt3-ligand-treated healthy human volunteers and cultured for four days in the presence of 10$^5$ allogeneic T-lymphocytes. Tritiated thymidine was added for the 16 last hours of culture. Results are representative of three independent experiments (FIG. 3). These results show that LDCAM-positive DCs are potent allo-stimulators.

Example 18

LDCAM-Specific Antibody (1F12)

These studies show that LDCAM-specific scfv binders were isolated using a whole cell panning phage display approach; that anti-LDCAM scfv-expressing phages were successfully converted into a scfv-Fc fusion protein (referred to herein interchangeably as a "maxibody") without major alteration in their binding specificity; and that the anti-LDCAM scfv-Fc fusion proteins were successfully used in immunoprecipitation, immunohistochemistry and functional assays. Human BDCA3+ blood dendritic cells were targeted in the context of whole PBMCs using a scfv-phage library. Some of the phages recovered from this panning approach specifically bound BDCA3+ DC. Briefly, PBMC from Flt3-ligand-treated healthy human volunteers were labeled with phage and fluorochrome-conjugated anti-phage antibody. Scfv filamentous phages were incubated with PBMC from Flt3-ligand-treated healthy volunteers. Non-binders were eliminated by extensive washes. PBMCs were labeled with anti-BDCA3 antibody and purified by flow cytometry. Phage were eluted from the surface of BDCA3+ DC by acidic shock. BDCA3+ DC binders were amplified in *E-coli*. First round BDCA3+ DC-binding phage were used in a second round of selection.

Figure 4:
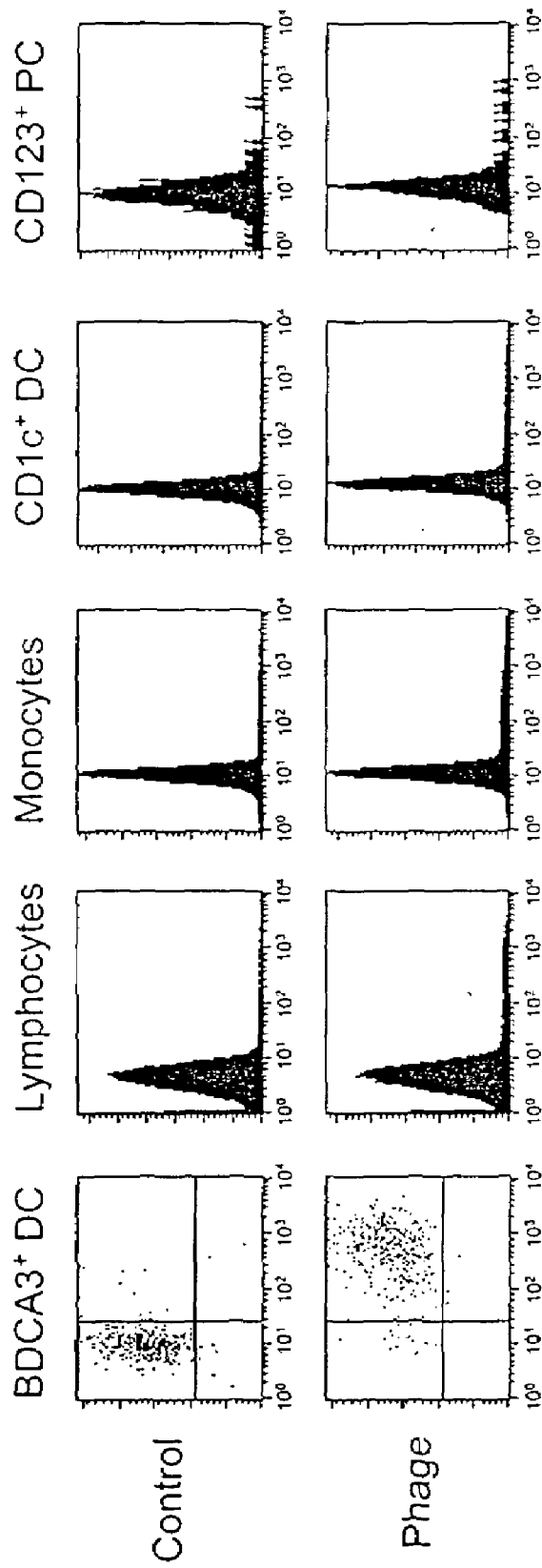
FIG. 4 is a series of FACS scans showing that the scfv-expressing phage 1F12 specifically binds to human BDCA3+ dendritic cells.

1F12 was shown to specifically bind to BDCA3+ DC. Antibodies against CD1c, CD123, CD14 and BDCA3 were then added. The results in FIG. 4 show that phage 1F12 (bottom row) labels specifically BDCA3+ DC. The upper row shows background labeling without filamentous phage. 1F12 is one of the 4% of the phages derived from the whole cell panning phage display approach that is cross-species reactive, i.e. to mouse and human. 1F12 scfv has been shown to bind BDCA3+ DC by flow cytometry, histology and immuno-precipitation. In mice, 1F12 scfv has been shown to specifically bind to a discrete subset of splenic DC (CD8a+ DC) which are believed to play a critical role in the activation of cytotoxic T-lymphocytes, as described in Example 17.

Figure 5:
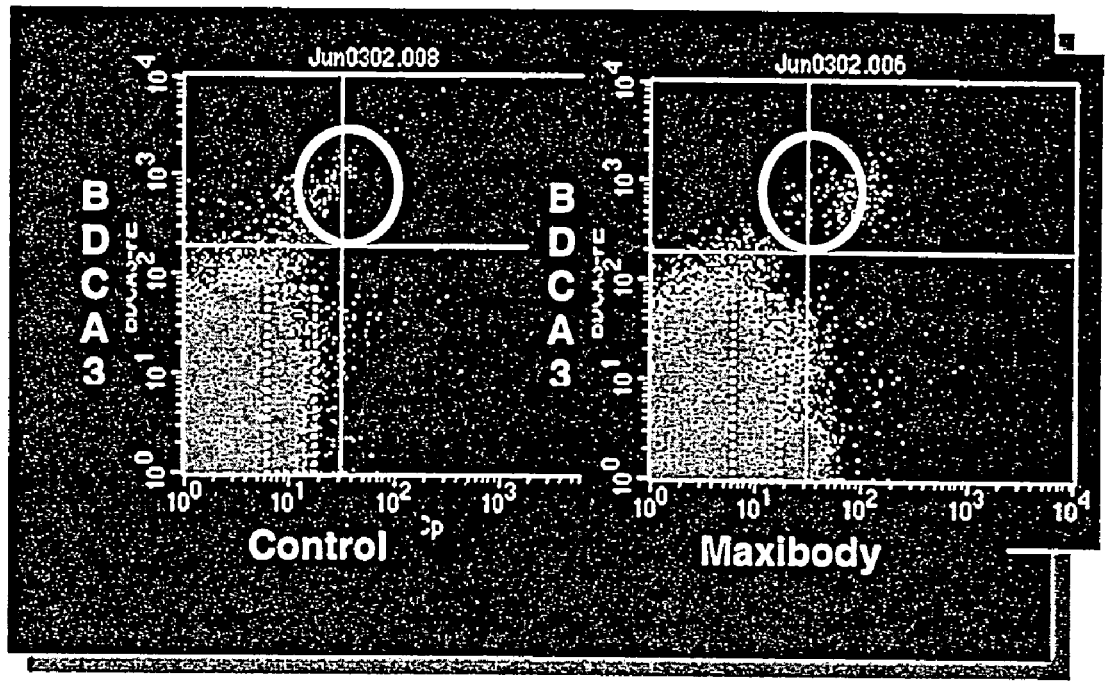
FIG. 5 is a FACS scan illustrating that the 1F12 scfv-Fc fusion protein ("maxibody") retained global specificity to LDCAM after conversion from a scfv-phage to a scfv-Fc fusion protein.

One specific scfv-phage (1F12) was converted into a scfv-Fc fusion protein. By fusing the scfv to the Fc domain of human IgG1 using techniques well known in the art. The conversion of the scfv to the scfv-Fc fusion protein did not adversely affect the specificity of the scfv binding region. (As shown in FIG. 5—note that the 1F12 scfv-Fc fusion protein was biotinylated for FACS analysis). The sequence for the variable heavy chain region is provided in SEQ ID NO: 12 and variable light chain region for 1F12 is provided in SEQ ID NO: 13.

Figure 7:
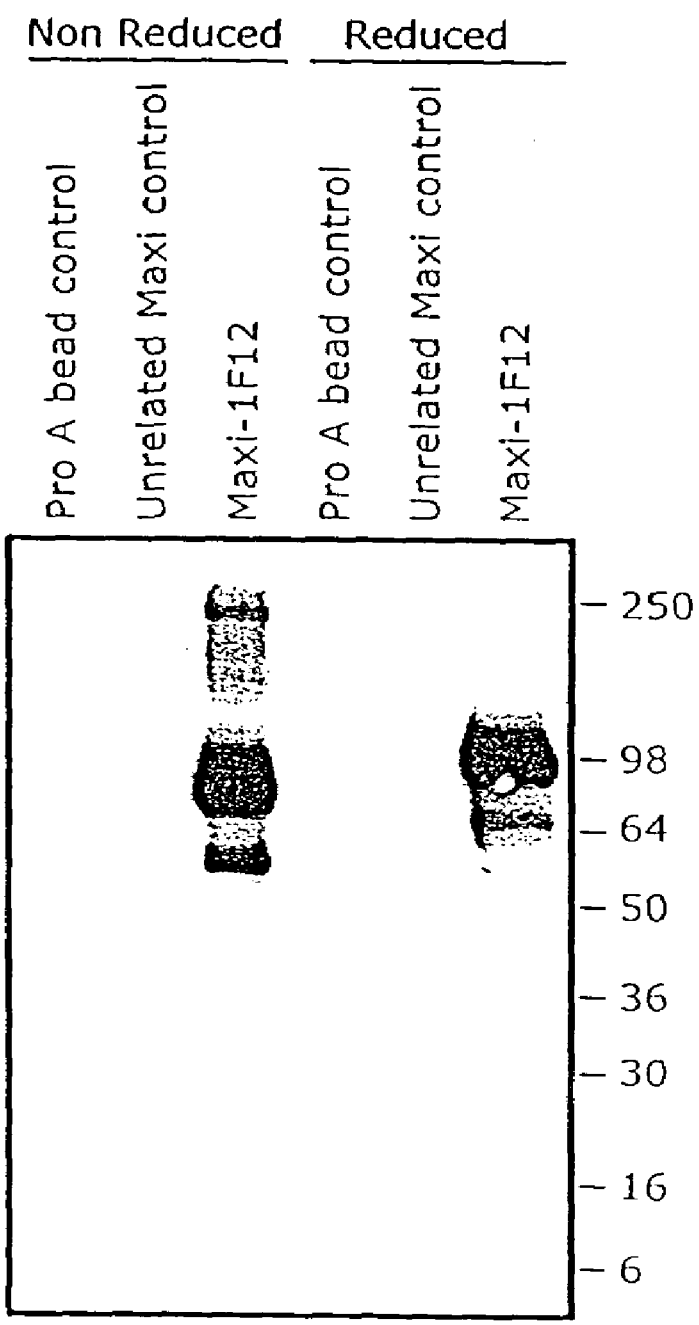
FIG. 7 is an image of an immunoprecipitation gel showing that the 1F12 scfv-Fc immunoprecipitated a 100 KDa glycoprotein from bone-marrow derived mouse dendritic cells, which was subsequently shown to be LDCAM by mass spectrometry.

1F12 has been shown to specifically bind LDCAM (also known in the art as Igsf4, TSLC1, SynCAM and Nectin-like-2). The scfv-Fc was introduced into a mammalian expression vector and produced in COS cells. The 1F12 scfv-Fc was shown to immunoprecipitate a 100 KDa glycoprotein from bone-marrow derived mouse DC (see FIG. 7). The 100 KDa protein was confirmed to be LDCAM by mass spectrometry.

The LDCAM-Fc fusion protein described in Example 9 was used in a dot-blot abinding assay to definitively show that 1F12-Fc specifically binds to LDCAM. Briefly, 2 ul of a 1 mg/ml solution of LDCAM-Fc or RANK-Fc (an unrelated Fc-control) was spotted onto a nitrocellulose filter and allowed to dry. After blocking for 1 hour with a milk/BSA/

Figure 8:
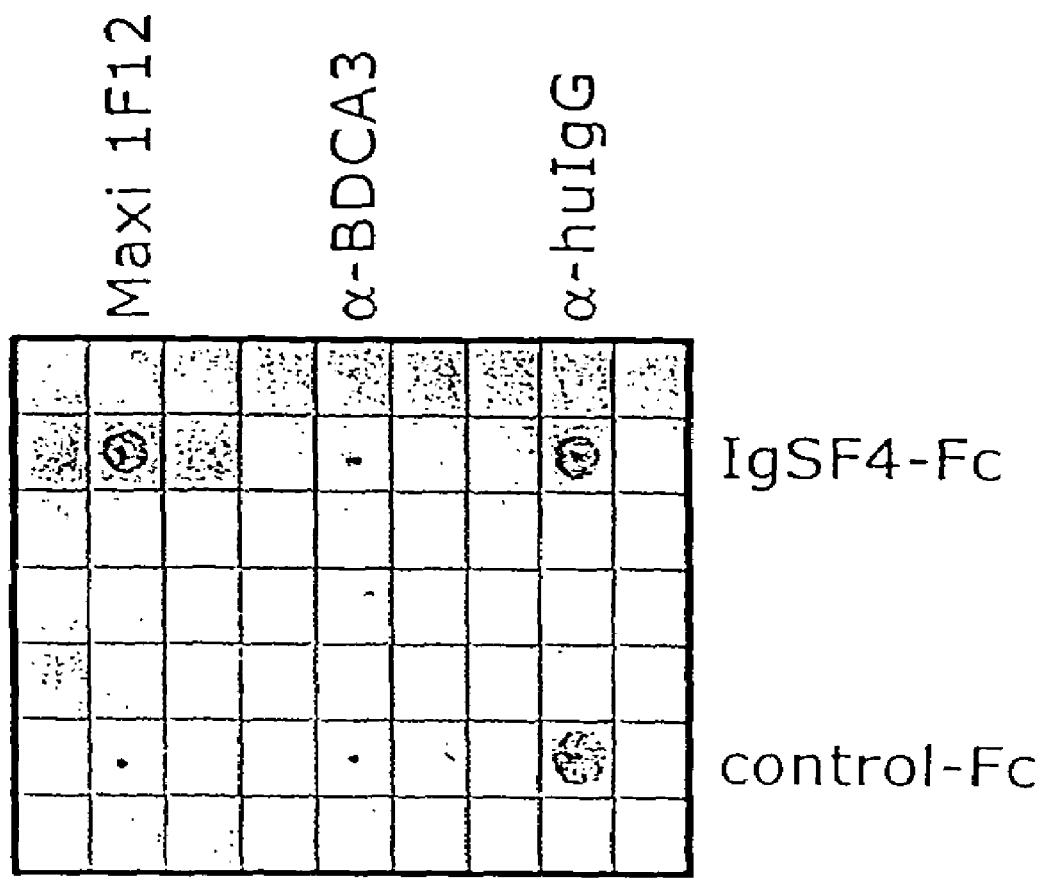
FIG. 8 is a immuno dot-blot showing the 1F12-scfv-Fc antibody specifically bound to recombinant LDCAM-Fc but not to unrelated RANK-Fc. These results show that the 1F12 scfv-Fc fusion protein specifically binds to LDCAM.

PBS, the following reagents were spotted onto the membrane: 100 ng of anti-BDCA3-biotin mAb, 100 ng of 1F12 scfv-Fc antibody or anti-human IgG-biotin (mouse Fab'2 anti-human IgG-biotin from Jackson Labs, Bar Harbor, Me.). After adding strep-HRP, labeling was revealed by TMB peroxydase substrate (Kirkegaard Perry Laboratories, Gaithersburg, Md.). As shown in FIG. 8, the 1F12-scfv-Fc antibody specifically bound to recombinant LDCAM-Fc but not to unrelated RANK-Fc. Mouse and human LDCAM are almost identical, having 98% identity at the protein level, which explains the cross-species reativity of the 1F12 antibody. The mAb against BDCA3 does not bind significantly to LDCAM-Fc, thus suggesting that the BDCA3 antigen is different from LDCAM.

These results show that the 1F12 scfv-Fc antibody (or fusion protein) specifically binds to LDCAM.

Example 19

LDCAM Inhibits T-Cell Activation

These studies show that LDCAM inhibits T-cell activation. Mouse (Blk-6) CD4+ and CD8+ were simultaneously exposed to plate-bound LDCAM-FC and one of the following T-cell activation stimuli: anti-CD3 mAb, conA, PHA or conA+IL-2. Culture supernatants were assayed for INF-gamma production by the T-cells, which is a marker of T-cell activation. Briefly, spleens were harvested from B6D2F1, mashed, the red blood cells lysed and the cells counted. The CD8+ and CD4+ cells were purified using Miltenyi Biotech anti-CD8 (cat #130-049-401) and anti-CD4 (cat #130-049-201) MAC™ beads following the manufacturer's suggested protocol. 48-well plates were coated with either LDCAM-Fc (5 ug/ml) or negative control P7.5 FC (5 ug/ml) Fc molecules for 2 hrs at 37 degrees C. and washed 2 times. A well containing no Fc protein was also included. Approprate wells were coated with anti-CD3 mAb for 2 hrs at 37 degrees C. and washed 2 times. Cells were plated at 1.25× $10^6$/ml in 1 ml of media (40% IMDM+40% Clicks+10% fetal bovine serum+sodium pyruvate+non-essential amino acids+2Me+PSG). Mitogens were added: conA (1 ug/ml), IL-2 (200 Units/ml) or PHA (1%) to appropriate wells. Supernatants were pulled on days 1 and 5 and assayed for IFN-gamma using a commercial IFN-gamma elisa kit.

Figure 9:
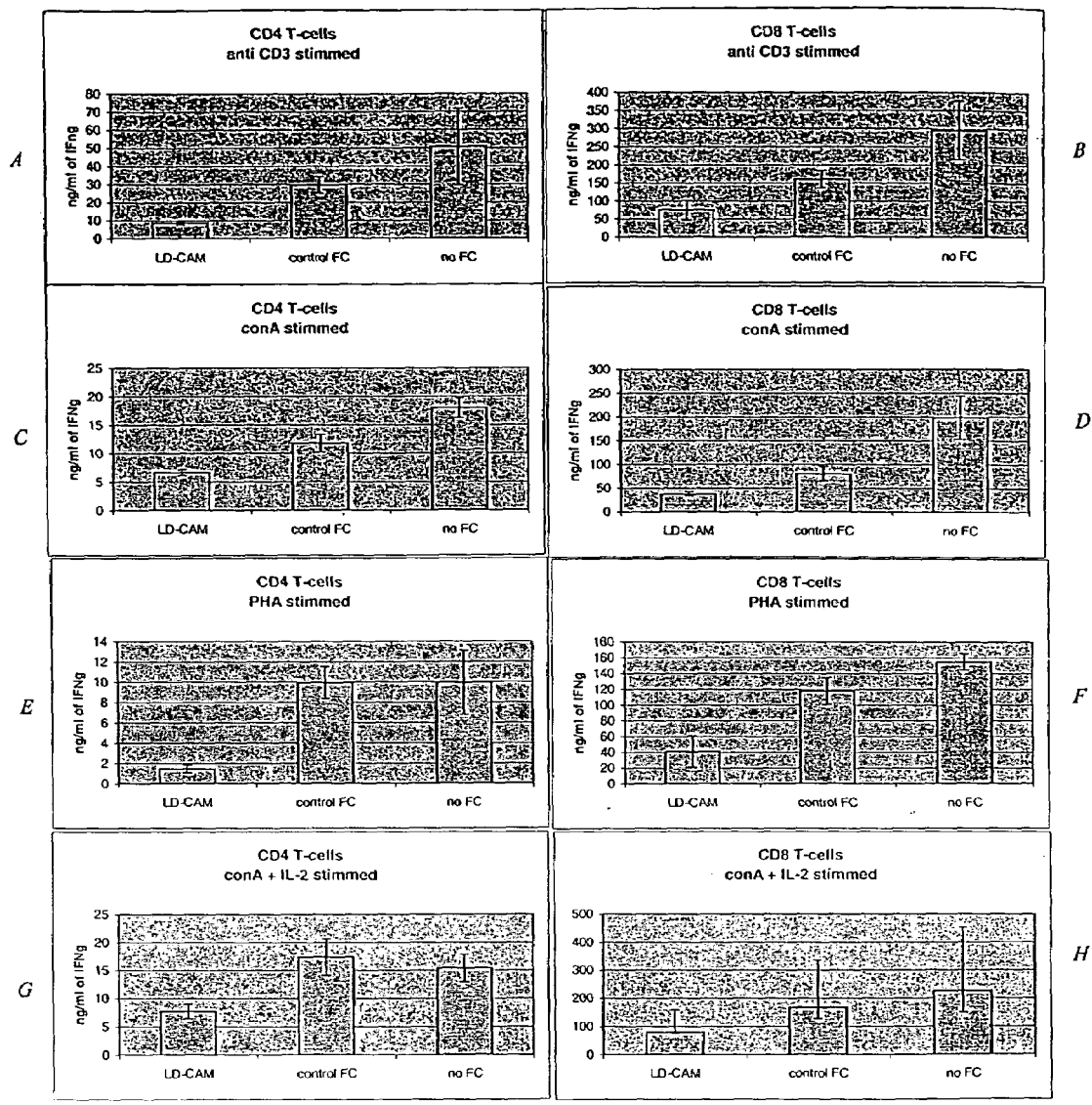
FIG. 9 shows that CD4+ T-cells were anergized by LDCAM to activation by anti-CD3 mAb and conA (FIGS. 9A and 9C, respectively).

FIG. 9 shows that CD4+ T-cells were anergized by LDCAM to activation by anti-CD3 mAb and conA (FIGS. 9A and 9C, respectively). FIGS. 9B, 9D, 9F and 9H show that CD8+ T-cells were were anergized by LDCAM to activation by anti-CD3 mAb, conA, PHA and conA+IL-2, respectively. These studies show that LDCAM is interacting with a molecule expressed on the surface of activated T-cells in a contact-dependent nature that prevents or dampens the activation of T-cells by a variety of stimuli. Theses studies show that LDCAM is a regulatory agent in inflammatory pathways. Therefore, LDCAM has therapeutic application as a pharmaceutical composition for preventing the activation of T-cells and for the treatment of disease involving T-cell activation, such as in autoimmune disease, inflammation, transplantation, cancer, infection and the like. Furthermore, agonists and antagonists of LDCAM, as defined above, may be therapeutic compositions for the treatment of the diseases described herein.

Example 19

CRTAM is a Cognate of LDCAM

These studies show that CRTAM is a cognate or binding partner of LDCAM.

Figure 10:
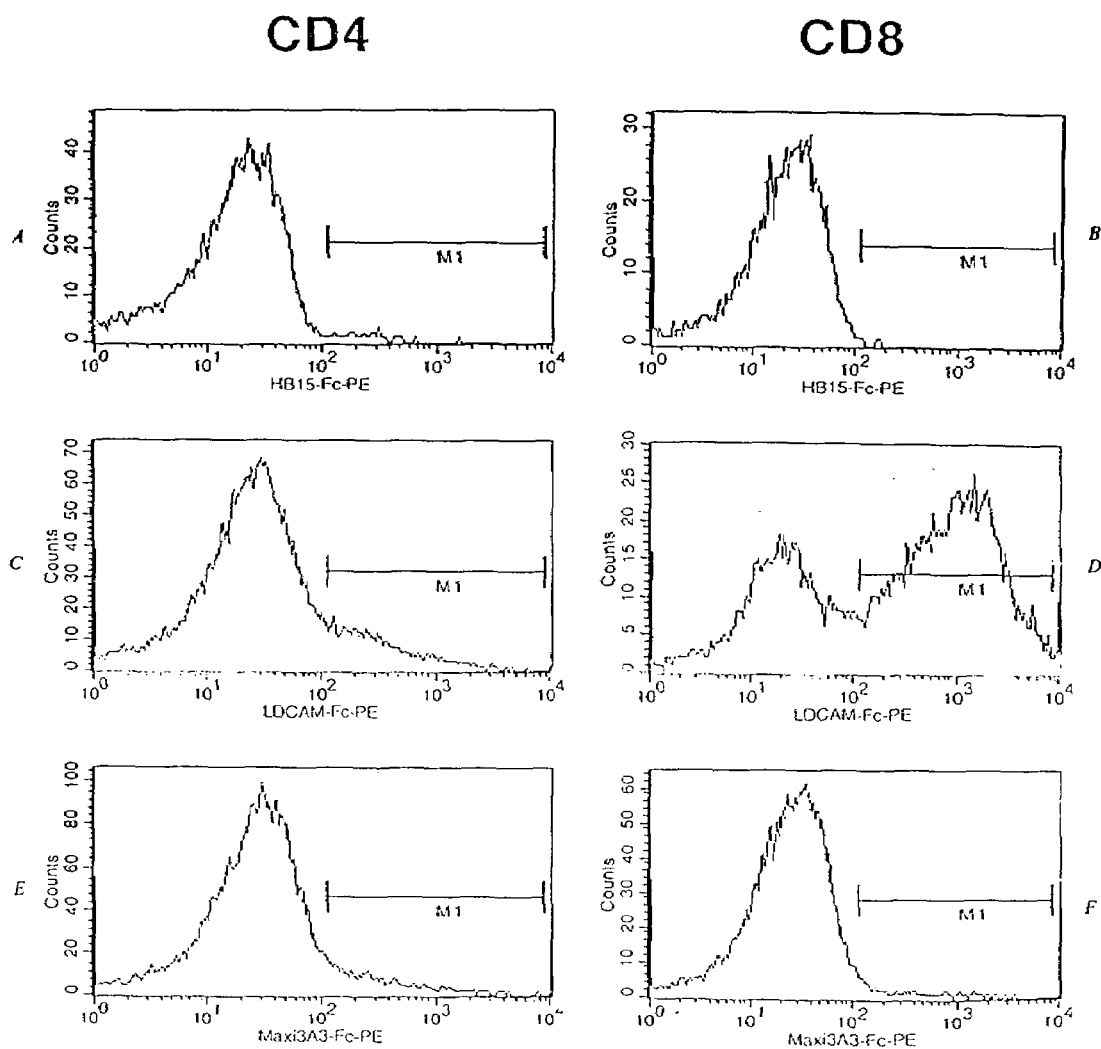
FIG. 10 are a series of FACS scans showing that LDCAM-Fc bound to CD8+ T-cells and to a lesser extent to CD4+ T-cells (FIGS. 10D and 10C, respectively), whereas, the 1F12 scfv-Fc antibody (i.e., the anti-LDCAM antibody) did not (FIGS. 10A and 10B are isotype controls). These studies show that LDCAM is interacting with a molecule expressed on the surface of activated T-cells in a contact-dependent nature that prevents or dampens the activation of T-cells by a variety of stimuli. Theses studies show that LDCAM is a regulatory agent in inflammatory pathways.
Figure 11:
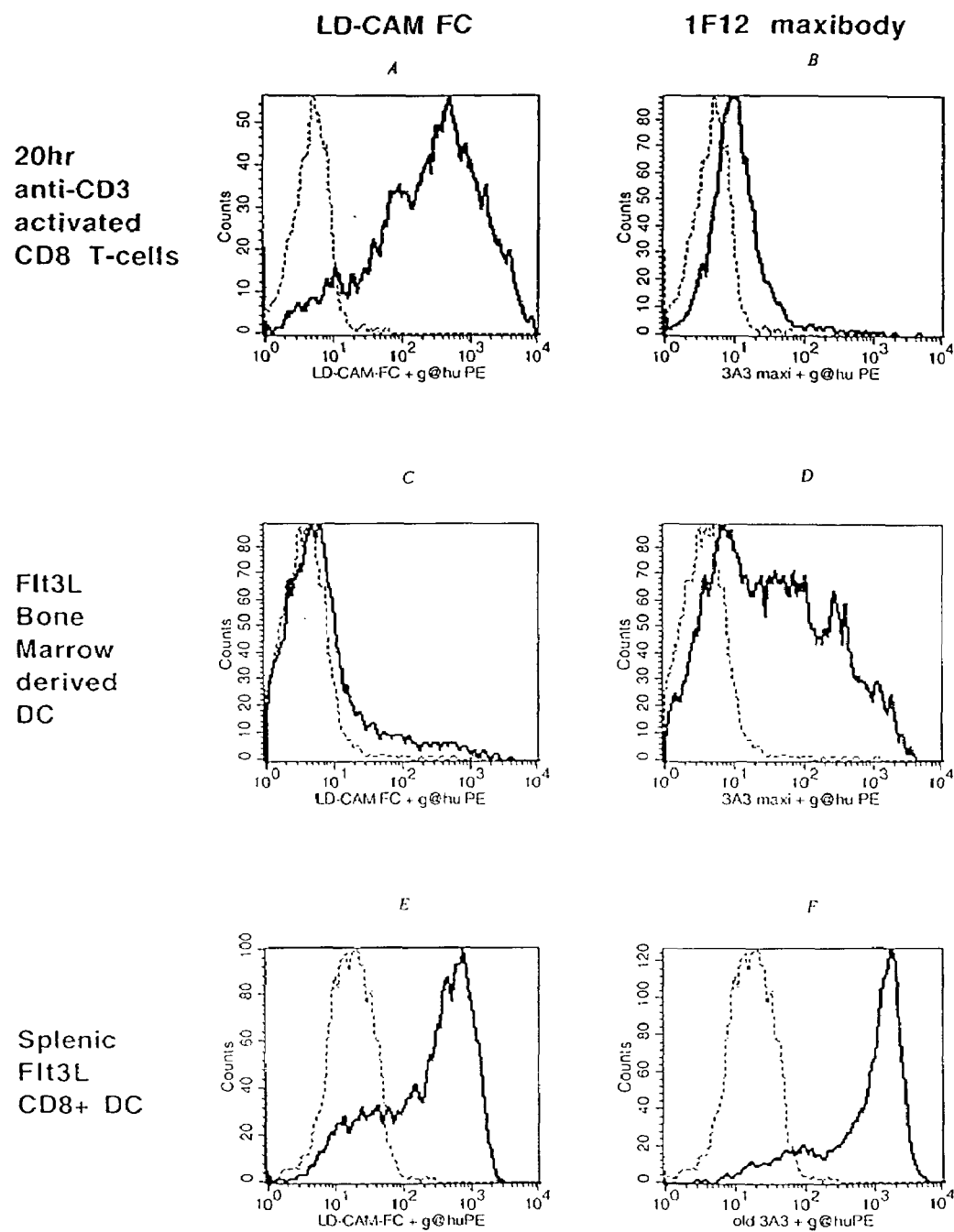
FIG. 11 are a series of FACS scans showing that anti-CD3-activated CD8+ T-cells binds LDCAM-Fc at high levels (FIG. 11A) and only marginal binding by the 1F12 scfv-Fc antibody (FIG. 11B). In contrast, LDCAM-Fc showed marginal binding of LDCAM-Fc (FIG. C) and high binding of the 1F12 scfv-Fc fusion protein (FIG. 11D). CD8+ splenic cells from Flt3-ligand-trreated mice showed heterogeneous binding of both LDCAM-Fc and 1F12 scfv-Fc (FIGS. 11E and 11F, respectively).

FACS analysis showed that LDCAM-Fc bound to CD8+ T-cells and to a lesser extent to CD4+ T-cells (FIGS. 10D and 10C, respectively), whereas, the 1F12 scfv-Fc antibody (i.e., the anti-LDCAM antibody) did not (FIGS. 10A and 10B are isotype controls). Additional FACS analysis shows that anti-CD3-activated CD8+ T-cells binds LDCAM-Fc at high levels (FIG. 11A) and only marginal binding by the 1F12 scfv-Fc antibody (FIG. 11B). In contrast, LDCAM-Fc showed marginal binding of LDCAM-Fc (Figure C) and high binding of the 1F12 scfv-Fc fusion protein (FIG. 11D). CD8+ splenic cells from Flt3-ligand-trreated mice showed heterogeneous binding of both LDCAM-Fc and 1F12 scfv-Fc (FIGS. 11E and 11F, respectively). Taken together, these studies show that LDCAM binds to activated Cytotoxic T-lymphocytes (CTL). In contrast, the 1F12 scfv-Fc fusion protein fails to label those cells. These results demonstrate that an alternative LDCAM counter-structure or cognate is present on the surface of activated CTL.

Figure 12:
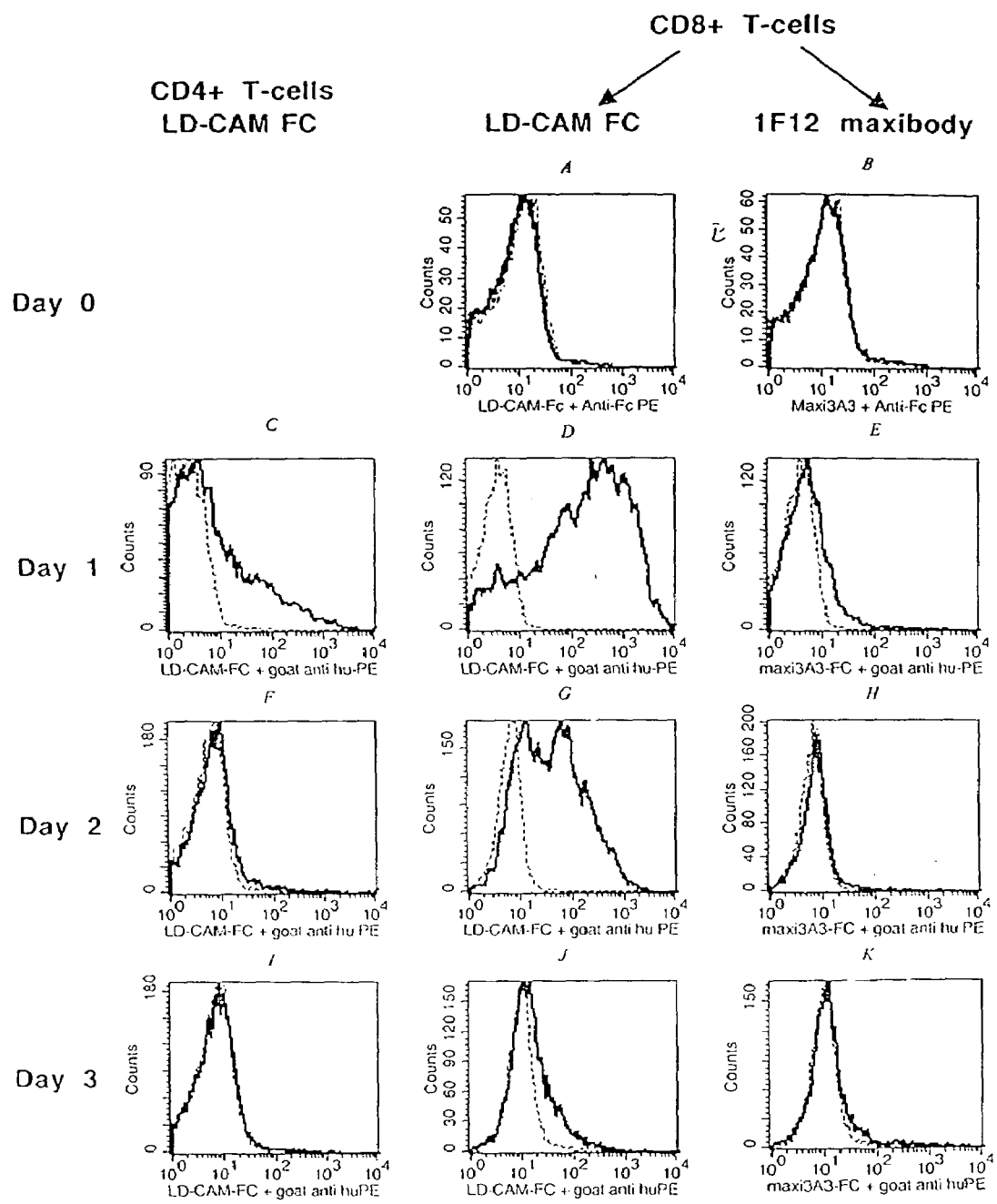
FIG. 12 are a series of FACS scans showing that the cell surface expression of the LDCAM counter-structure (CRTAM) is temporally expressed on the cell surface of activated CD4+ and CD8+ T-cells. FACS analysis showed that cell surface expression of the LDCAM-Fc binding to its cognate on CD4+ T-cells dimished after approximately 24 hours (FIGS. 12C, 12F and 12I). Interestingly, CD8+ T-cells showed a strong increase in the cell surface expression of CRTAM 24 hours after activation (FIG. 12D) and a progressive waning of cell surface expression at 48 and 72 hours post activation (FIGS. 12G and 12J, respectively). The expression of LDCAM on the cell surface of the activated CD4+ and CD8+ T-cells was minimal and unchanged over time (FIGS. 12B, 12E, 12H and 12K).

The cell surface expression of the LDCAM counter-structure was shown to be temporally expressed on the cell surface of activated CD4+ and CD8+ T-cells. FACS analysis showed that cell surface expression of the LDCAM-Fc binding to its cognate on CD4+ T-cells dimished after approximately 24 hours (FIGS. 12C, 12F and 12I). Interestingly, CD8+ T-cells showed a strong increase in the cell surface expression of the LDCAM cognate 24 hours after activation (FIG. 12D) and a progressive waning of cell surface expression at 48 and 72 hours post activation (FIGS. 12G and 12J, respectively). The expression of LDCAM on the cell surface of the activated CD4+ and CD8+ T-cells was minimal and unchanged over time (FIGS. 12B, 12E, 12H and 12K).

The cognate of LDCAM was determined to be CRTAM by immunoprecipitating the binding pairs and performing mass spectrometry analysis on the isolated bands. 1F12 scfv-Fc and LDCAM-Fc immunoprecipitated proteins of close but distinct molecular weights. Activated mouse CTL or mouse bone marrow-derived DC were surface biotinylated and lysed with detergent. The cellular lysates were pre-cleared with a protein-A bead matrix. 1F12 scfv-Fc was added to the mouse bone marrow-derived DC cellular lysate and LDCAM-Fc was added to the activated CTL cellular lysate were then used to immunoprecipitate their respective target. Protein-A bead matrix was added to pull out the LDCAM-Fc and the 1F12 scfv-Fc complexes from the lysates. The apparent MW of the precipitated proteins were compared on a reducing gel shown in FIG. 13. FIG. 13A is the band immunoprecipitated by LDCAM-Fc from activated CTL. FIG. 13B is the band immunoprecipitated by 1F12 scfv-Fc from the bone marrow-derived DC. Similar results were obtained with splenic CD8+ DC.

The band from FIG. 13A was excised and analyzed by mass spectrometry. Those results are presented below and confirm that CRTAM is the cognate of LDCAM Settings Used
peptide MW:
charge-state:
peptide error: 0.75 u
fragment error: 0.75 u
peak width: 1.0 u
e-value cutoff: 1.0E−15
recalibrate: no
N-terminal pyroglu considered: yes
Met oxidation considered (2 max): yes
Fixed cysteine: carbamidomethyl (160.031)
Variable cys mass (2 max):
Databases searched: nr_aa, patent_aa,
ms_garbage_aa, celera_human_aa,
celera_mouse_aa

|   | | b | $b^{2+}$ | b - H2O | y | $y^{2+}$ | |
|---|---|---|---|---|---|---|---|
| E | 0 | — | — | — | — | — | 13 |
| S | 1 | 130.05 | 65.53 | 112.04 | 1411.67 | 706.34 | 12 |
| E | 2 | 217.08 | 109.04 | 199.07 | 1324.64 | 662.82 | 11 |
| I | 3 | 346.13 | 173.56 | 328.11 | 1195.60 | 598.30 | 10 |
| S | 4 | 459.21 | 230.10 | 441.19 | 1082.51 | 541.76 | 9 |
| E | 5 | 546.24 | 273.62 | 528.23 | 995.48 | 498.24 | 8 |
| Q | 6 | 675.28 | 338.14 | 657.27 | 866.44 | 433.72 | 7 |
| A | 7 | 803.34 | 402.17 | 785.33 | 738.38 | 369.69 | 6 |
| L | 8 | 874.38 | 437.69 | 856.36 | 667.34 | 334.17 | 5 |
| E | 9 | 987.46 | 494.23 | 969.45 | 554.26 | 277.63 | 4 |
| S | 10 | 1116.51 | 558.75 | 1098.49 | 425.21 | 213.11 | 3 |
| Y | 11 | 1203.54 | 602.27 | 1185.52 | 338.18 | 169.59 | 2 |
| R | 12 | 1366.60 | 683.80 | 1348.59 | 175.12 | 88.06 | 1 |

| MAPLINK | E-VALUE | CHRG. | BEGIN-END | SEQUENCE | SEARCH DB | PROTEIN DESCRIPTION |
|---|---|---|---|---|---|---|
| MAP(01) | 8.1E−26 | +2 | 319-331 | ESEISEQALESYR | nr_aa | ref|NP_062338.1 cytotoxic and regulatory T cell molecule; class I-restricted T cell-associated molecule [*Mus musculus*] gi|3930161|gb|AAC80266.1| class I MHC-restricted T cell associated molecule [*Mus musculus*] |
| MAP(01) | 8.1E−26 | +2 | 319-331 | ESEISEQALESYR | patent_aa | gsp|AAW04405 Mouse CRTAM. |
| MAP(01) | 8.1E−26 | +2 | 145-157 | ESEISEQALESYR | nr_aa | dbj|BAB24204.2 unnamed protein product [*Mus musculus*] |
| MAP(01) | 8.1E−26 | +2 | 331-343 | ESEISEQALESYR | nr_aa | ref|XP_236103.1 similar to cytotoxic and regulatory T cell molecule; class I-restricted T cell-associated molecule [*Mus musculus*] [*Rattus norvegicus*] |
| MAP(01) | 8.1E−26 | +2 | 319-331 | ESEISEQALESYR | patent_aa | gb|AAC10711.1 Sequence 4 from patent U.S. Pat. No. 5686257 |
| MAP(01) | 8.1E−26 | +2 | 319-331 | ESEISEQALESYR | celera_mouse_aa | cra|MCP17461.1/len = 388/protein_uid = 197000028318745/ga_name = GA_x6K02T2PVTD/ ga_uid = 232000009795437/transcript_name = mCT4204.1/transcript_uid = 110000066470850/ cg_name = mCG5069.1/ start_codon = 0/class = Otto |

Figure 14:
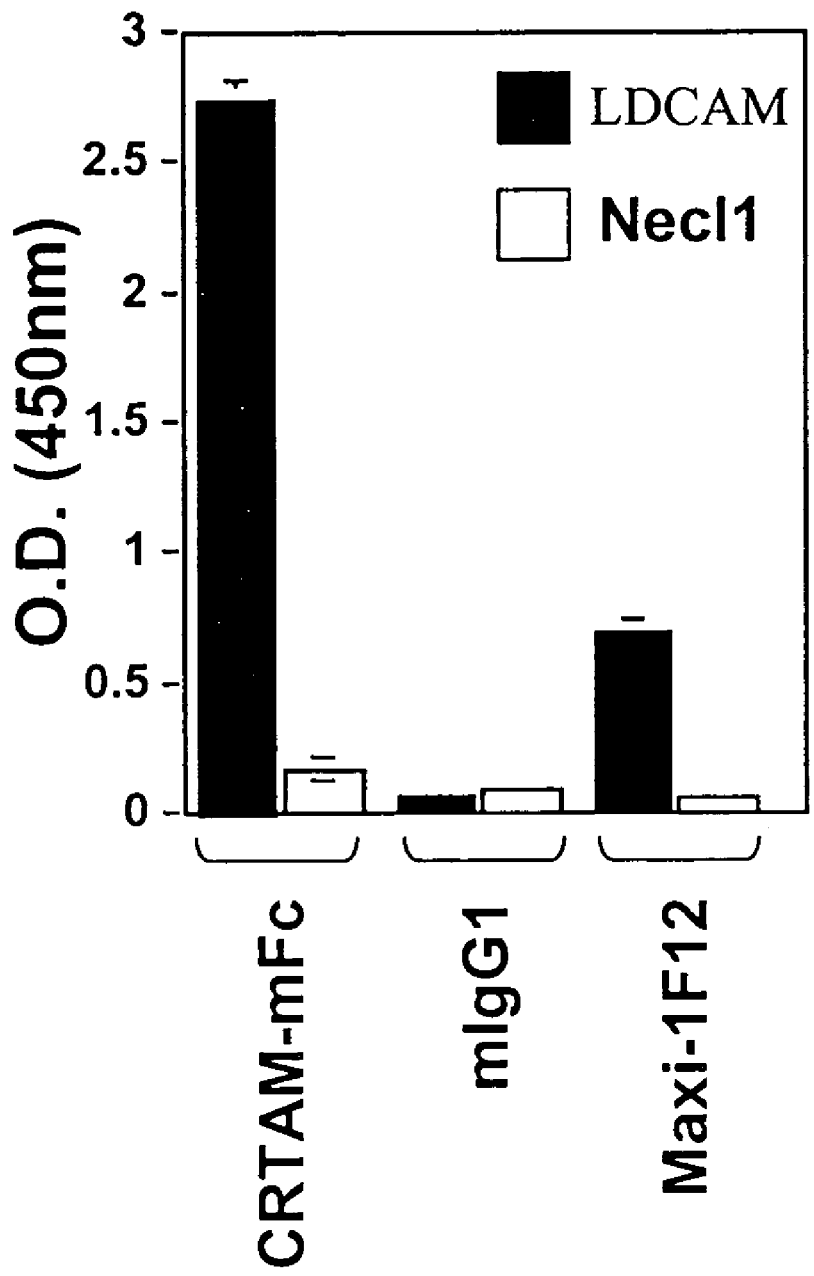
FIG. 14 is a graph showing ELISA data proving that LDCAM specifically binds to CRTAM.
Figures 15A, 15B:
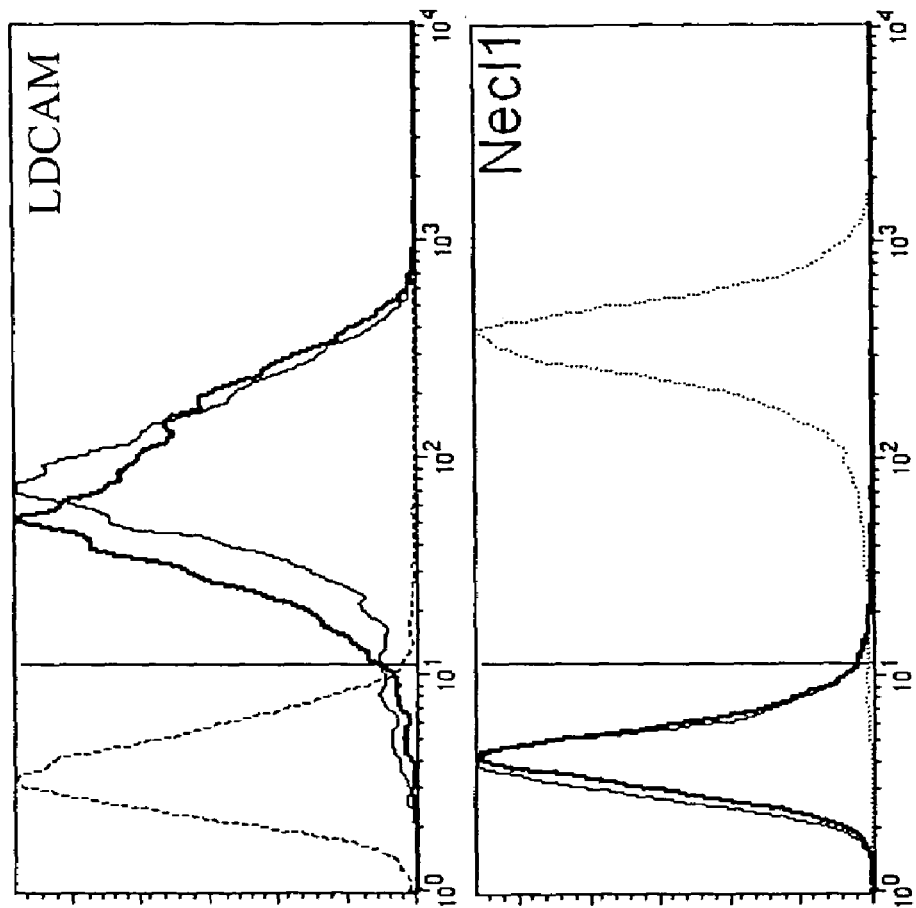
FIG. 15A shows that the CRTAM-Fc binds to the cells transduced to express LDCAM (bold line), but not to cells transduced to express Necl1 (FIG. 15B).

In an ELISA format, FIG. 14 shows that LDCAM specifically bound to CRTAM-Fc, but not to Necl1 protein or an IgG control. In a seperate set of experiments, the mouse thymoma cell line EL4 (The American Type Culture Collection, ATCC TIB-39) were transduced with a lentiviral vectors encoding for human LDCAM (FIG. 15A) or human Necl1 (FIG. 15B). Transduced cells were then enriched by magnetic cell sorting using the 1F12 maxibody or an anti-Necl1 monoclonal antibody, respectively. Enriched transduced cells were probed with huCRTAM-Fc (thick line), 1F12 scfv-Fc (thin line) or anti-Necl1 antibody (dashed line). Vertical lines represent the limit for non-specific binding as measured by unrelated Fc-isotype matched antibodies.

Figure 16:
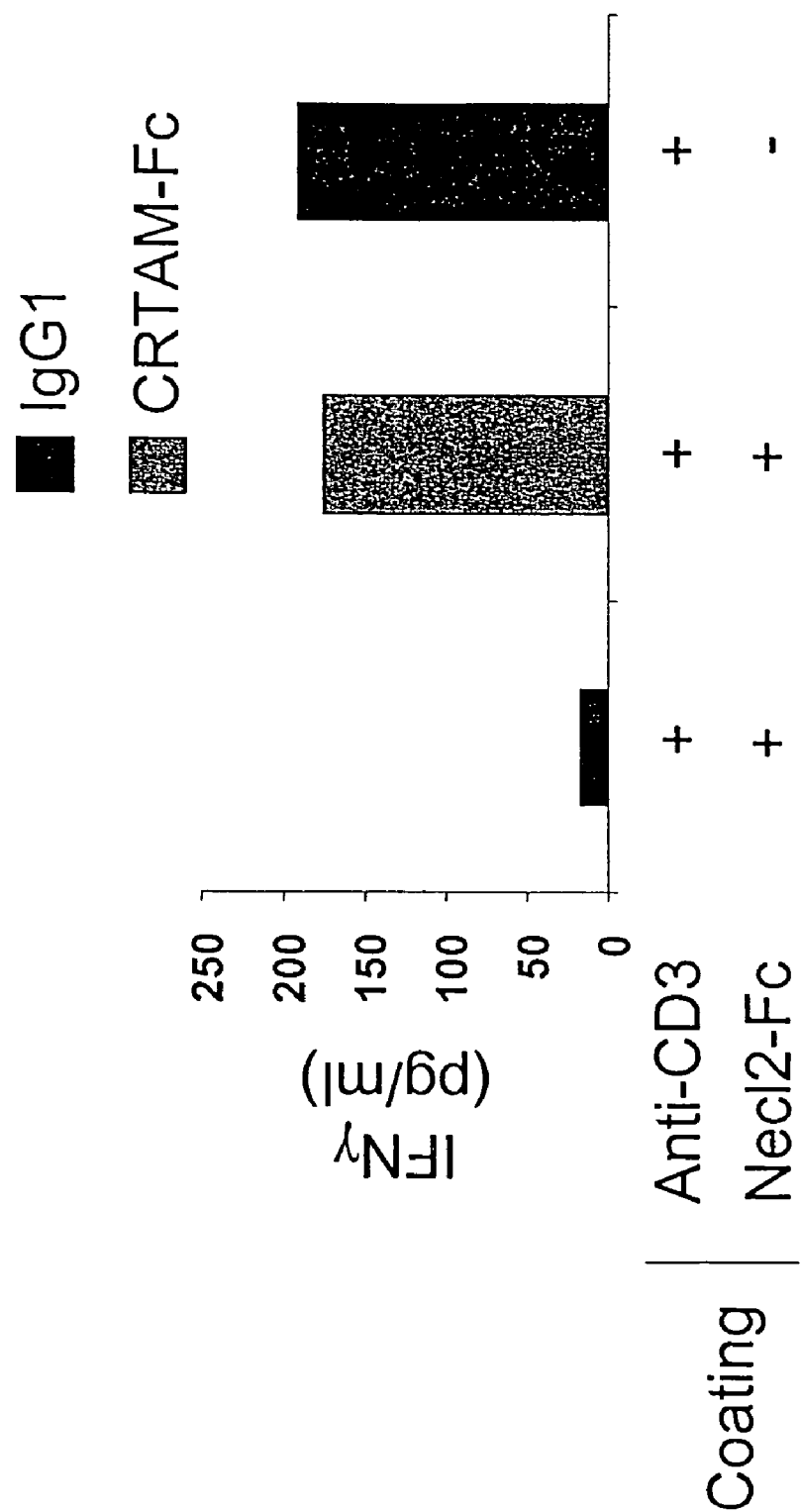
FIG. 16 demonstrates that crosslinking CRTAM with LDCAM-Fc down-regulates cytokine secretion (IFNγ) by in vitro activated mouse CD8+ T-lymphocytes.

It was shown that crosslinking CRTAM down-regulates cytokine secretion (IFNγ) by in vitro activated mouse CD8+ T-lymphocytes (FIG. 16). A standard ELISA plate is coated with either anti-CD3 monolconal antibody and/or LDCAM-Fc protein. Activated CD8+ T-cells were isolated using standard procedures and were added to the well(s) in the presence of either an IgG1 isotype control or soluble CRTAM-Fc. A dramatic decrease in IFNγ secretion by the T-cells was seen when the cells were crosslinked by the LDCAM-Fc bound to the plate. Conversely, an increase in IFNγ secretion by the T-cells was seen when CRTAM-Fc was added to the assay as a competitor between the LDCAM-Fc bound to the plate and the CRTAM expressed on the cells. These studies further demonstrate that the biological consequence of LDCAM binding and crosslinking CRTAM is to reduce T-cell activation, proliferation, and release of proinflammatory cytokines. As such, a LDCAM agonist, such as but not limited to a LDCAM-Fc fusion protein or multimerized form of LDCAM, as well as an anti-CRTAM antibody capable of crosslinking CRTAM on the surface of cells would be useful in reducing T-cell activation, proliferation, and release of proinflammatory cytokines.

These studies show that LDCAM is interacting with CRTAM expressed on the surface of activated T-cells in a contact-dependent nature. In vitro studies described in Example 18 clearly demonstrate that the interaction of LDCAM and CRTAM prevents or dampens the activation of T-cells by a variety of stimuli. Theses studies show that LDCAM and its cognate CRTAM are involved in inflammatory pathways. Therefore, LDCAM has therapeutic application as a pharmaceutical composition for preventing the activation of T-cells and for the treatment of disease involving T-cell activation, such as in autoimmune disease, inflammation, transplantation, cancer, infection and the like. Furthermore, agonists and antagonists of the LDCAM/CRTAM interaction, as defined throughout the specification, may have therapeutic value as therapeutic compositions for the treatment of the diseases described herein.

What is claimed is:

1. An isolated LDCAM-specific antibody, comprising the variable heavy chain of SEQ ID NO:12 and the variable light chain of SEQ ID NO:13.

2. A composition, comprising the antibody of claim 1 and a physiologically acceptable carrier, diluent or excipient.

3. The antibody of claim 1, further comprising an Fc domain.

4. The antibody of claim 3, wherein the Fc domain is an IgG Fc domain.

5. The antibody of claim 3, wherein the Fc domain is an IgA Fc domain.

6. The antibody of claim 3, wherein the Fc domain is an IgE Fc domain.

7. The antibody of claim 4, wherein the IgG Fc domain is an IgG1 Fc domain.

8. The antibody of claim 7, wherein the IgG1 Fc domain is a human IgG1 Fc domain.

9. The antibody of claim 4, wherein the IgG Fc domain is an IgG2 Fc domain.

10. The antibody of claim 9, wherein the IgG2 Fc domain is a human IgG2 Fc domain.

11. The antibody of claim 4, wherein the Fc domain is an IgG3 Fc domain.

12. The antibody of claim 11, wherein the IgG3 Fc domain is a human IgG3 Fc domain.

* * * * *